United States Patent
Fujii et al.

(10) Patent No.: US 8,592,379 B2
(45) Date of Patent: Nov. 26, 2013

(54) METASTIN DERIVATIVE AND USE THEREOF

(75) Inventors: Nobutaka Fujii, Kyoto (JP); Shinya Oishi, Kyoto (JP); Kenji Tomita, Kyoto (JP)

(73) Assignees: Kyoto University, Kyoto-Shi (JP); Takeda Pharmaceutical Company Limited, Osaka-Shi (JP)

( * ) Notice: Subject to any disclaimer, the term of this patent is extended or adjusted under 35 U.S.C. 154(b) by 305 days.

(21) Appl. No.: 12/990,161

(22) PCT Filed: Apr. 28, 2009

(86) PCT No.: PCT/JP2009/058409
§ 371 (c)(1),
(2), (4) Date: Oct. 28, 2010

(87) PCT Pub. No.: WO2009/139298
PCT Pub. Date: Nov. 19, 2009

(65) Prior Publication Data
US 2011/0039786 A1    Feb. 17, 2011

(30) Foreign Application Priority Data
Apr. 30, 2008  (JP) .................... 2008-119235

(51) Int. Cl.
| | | |
|---|---|---|
| A61K 38/06 | (2006.01) |
| A61K 38/07 | (2006.01) |
| A61K 38/00 | (2006.01) |
| A61P 25/28 | (2006.01) |
| A61P 35/00 | (2006.01) |
| C07K 5/00 | (2006.01) |
| C07K 7/00 | (2006.01) |
| C07K 16/00 | (2006.01) |
| C07K 17/00 | (2006.01) |

(52) U.S. Cl.
USPC ......... 514/21.9; 514/17.8; 514/19.3; 530/331

(58) Field of Classification Search
None
See application file for complete search history.

(56) References Cited

U.S. PATENT DOCUMENTS

| | | | |
|---|---|---|---|
| 6,800,611 B2 * | 10/2004 | Fujii et al. ...................... 514/1.3 |
| 8,361,968 B2 * | 1/2013 | Kitada et al. .................. 514/19.8 |
| 8,404,643 B2 * | 3/2013 | Asami et al. .................. 514/19.5 |
| 2004/0142875 A1 | 7/2004 | Fujii et al. ........................ 514/17 |
| 2006/0241051 A1 * | 10/2006 | Kitada et al. ..................... 514/15 |
| 2008/0312155 A1 * | 12/2008 | Kitada et al. ..................... 514/15 |
| 2009/0093615 A1 * | 4/2009 | Asami et al. .................... 530/328 |
| 2009/0105152 A1 * | 4/2009 | Asami et al. ..................... 514/14 |
| 2009/0215700 A1 * | 8/2009 | Asami et al. ..................... 514/15 |
| 2009/0298765 A1 * | 12/2009 | Kitada et al. ..................... 514/12 |
| 2009/0318365 A1 * | 12/2009 | Kitada et al. ..................... 514/15 |
| 2011/0059888 A1 * | 3/2011 | Asami et al. .................... 514/6.8 |
| 2011/0118172 A1 * | 5/2011 | Asami et al. .................... 514/1.3 |
| 2011/0212890 A1 * | 9/2011 | Asami ............................ 514/6.8 |
| 2011/0312898 A1 * | 12/2011 | Matsui ......................... 514/19.3 |
| 2012/0015868 A1 * | 1/2012 | Kitada et al. .................... 514/1.9 |

FOREIGN PATENT DOCUMENTS

| | | | |
|---|---|---|---|
| EP | 1 577 323 A1 | | 9/2005 |
| WO | WO9000399 | * | 1/1990 |
| WO | WO-2006/001499 A2 | | 1/2006 |
| WO | 2007/125619 A1 | | 11/2007 |
| WO | 2008/050897 A1 | | 5/2008 |

OTHER PUBLICATIONS

Tomita K, et al. Structure-Activity Relationship Study and NMR Analysis of Fluorobenzoyl Pentapeptide GPR54 Agonists., Biopolymers (2008) 90; p. 503-511.
Maeda, K. et al, Metastin/Kisspeptin and control of estrous cycle in rats, Rev. Endocr. Metab. Disord. (2007)8; p. 21-29.
Supplementary European Search Report for European patent Application No. 09 74 6505.
Tomita et al., "Fmoc-based solid-phase synthesis of GPR54-agonistic pentapeptide derivatives containing alkene- and fluoroalkene-dipeptide isosteres", Biopolymers, 2007, vol. 88, No. 2, p. 272-278.
Tomita et al., "Cis-amide Tokatai to shiteno Z-gata Alkene Oyobi E-gata Fluoroalkene Dipeptide Isoster no Gosei to Oyo", Abstracts of Annual Meeting of Pharmaceutical Society of Japan, Mar. 5, 2008, vol. 128th, No. 2, p. 95.
Tomita et al., "SAR and QSAR studies on the N-terminally acylated pentapeptide agonists for GPR54", J. Med. Chem., 2007, vol. 50, No. 14, p. 3222-3228.
Tomita et al., "Structure-activity relationship study on small peptidic GPR54 agonists", Bioorg. Med. chem., 2006, vol. 14, No. 22, p. 7595-7603.
Niida et al., "Design and synthesis of downsized metastin (45-54) analogs with maintenance of high GPR54 agonistic activity", Bioorg. Med. Chem. Lett., 2006, vol. 16, No. 1, p. 134-137.
Tomita et al., "Development of novel G-protein-coupled receptor 54 agonists with resistance to degradation by matrix metalloproteinase", J. Med. Chem., Dec. 11, 2008, vol. 51, No. 23, p. 7645-7649.
Tomita et al., "Dipeptide Isoster no Bunkigata Gosei ni yoru Koso Taisei GPR54 Agonist no Shoshutsu", Abstracts Symposium on Progress in Organic Reactions and Syntheses, Oct. 17, 2008, vol. 34th, pp. 144-145.
Oishi et al., "Alkene-gata Dipeptide Isoster no Goseiho no Kaihatsu to Seiri Kassei Peptide no Kozo Kassei Sokan Kenkyu eno Oyo", Journal of Synthetic Organic Chemistry, Japan, Sep. 1, 2008, vol. 66, No. 9, pp. 846-857.
Tomita et al., Abstracts of Annual Meeting of Pharmaceutical Society of Japan, vol. 128, No. 2, p. 95 (English Translation), 2008.
Tomita et al., Abstracts Symposium on Progress in Organic Reactions and Syntheses, Oct. 17, 2008, vol. 34, pp. 144-145 (English Translation).

\* cited by examiner

*Primary Examiner* — Marcela M Cordero Garcia
(74) *Attorney, Agent, or Firm* — Edwards Wildman Palmer LLP; David G. Conlin; Lisa Swiszcz

(57) ABSTRACT

The present invention provides a metastin derivative represented by the formula (I):

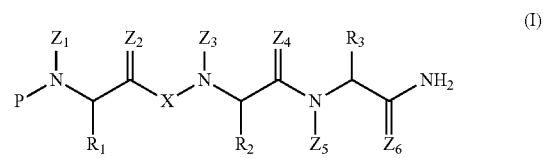

wherein each symbol is as defined in the specification, or a salt thereof, or a pharmaceutical composition containing it. The metastin derivative or a salt thereof is superior in blood stability, and has a cancer metastasis suppressive action or cancer growth suppressive action.

5 Claims, No Drawings

SEQUENCE LISTING

<160> NUMBER OF SEQ ID NOS: 67

<210> SEQ ID NO 1
<211> LENGTH: 4
<212> TYPE: PRT
<213> ORGANISM: Homo sapiens

<400> SEQUENCE: 1

Asn Trp Asn Ser
1

<210> SEQ ID NO 2
<211> LENGTH: 5
<212> TYPE: PRT
<213> ORGANISM: Homo sapiens

<400> SEQUENCE: 2

Tyr Asn Trp Asn Ser
1               5

<210> SEQ ID NO 3
<211> LENGTH: 6
<212> TYPE: PRT
<213> ORGANISM: Homo sapiens

```
<400> SEQUENCE: 3

Asn Tyr Asn Trp Asn Ser
1               5

<210> SEQ ID NO 4
<211> LENGTH: 7
<212> TYPE: PRT
<213> ORGANISM: Homo sapiens

<400> SEQUENCE: 4

Pro Asn Tyr Asn Trp Asn Ser
1               5

<210> SEQ ID NO 5
<211> LENGTH: 8
<212> TYPE: PRT
<213> ORGANISM: Homo sapiens

<400> SEQUENCE: 5

Leu Pro Asn Tyr Asn Trp Asn Ser
1               5

<210> SEQ ID NO 6
<211> LENGTH: 9
<212> TYPE: PRT
<213> ORGANISM: Homo sapiens

<400> SEQUENCE: 6

Asp Leu Pro Asn Tyr Asn Trp Asn Ser
1               5

<210> SEQ ID NO 7
<211> LENGTH: 10
<212> TYPE: PRT
<213> ORGANISM: Homo sapiens

<400> SEQUENCE: 7

Lys Asp Leu Pro Asn Tyr Asn Trp Asn Ser
1               5                   10

<210> SEQ ID NO 8
<211> LENGTH: 11
<212> TYPE: PRT
<213> ORGANISM: Homo sapiens

<400> SEQUENCE: 8

Glu Lys Asp Leu Pro Asn Tyr Asn Trp Asn Ser
1               5                   10

<210> SEQ ID NO 9
<211> LENGTH: 12
<212> TYPE: PRT
<213> ORGANISM: Homo sapiens

<400> SEQUENCE: 9

Arg Glu Lys Asp Leu Pro Asn Tyr Asn Trp Asn Ser
1               5                   10

<210> SEQ ID NO 10
<211> LENGTH: 13
<212> TYPE: PRT
<213> ORGANISM: Homo sapiens

<400> SEQUENCE: 10

Gln Arg Glu Lys Asp Leu Pro Asn Tyr Asn Trp Asn Ser
```

```
1               5                  10
```

<210> SEQ ID NO 11
<211> LENGTH: 14
<212> TYPE: PRT
<213> ORGANISM: Homo sapiens

<400> SEQUENCE: 11

```
Val Gln Arg Glu Lys Asp Leu Pro Asn Tyr Asn Trp Asn Ser
1               5                  10
```

<210> SEQ ID NO 12
<211> LENGTH: 15
<212> TYPE: PRT
<213> ORGANISM: Homo sapiens

<400> SEQUENCE: 12

```
Leu Val Gln Arg Glu Lys Asp Leu Pro Asn Tyr Asn Trp Asn Ser
1               5                  10                  15
```

<210> SEQ ID NO 13
<211> LENGTH: 16
<212> TYPE: PRT
<213> ORGANISM: Homo sapiens

<400> SEQUENCE: 13

```
Val Leu Val Gln Arg Glu Lys Asp Leu Pro Asn Tyr Asn Trp Asn Ser
1               5                  10                  15
```

<210> SEQ ID NO 14
<211> LENGTH: 17
<212> TYPE: PRT
<213> ORGANISM: Homo sapiens

<400> SEQUENCE: 14

```
Ala Val Leu Val Gln Arg Glu Lys Asp Leu Pro Asn Tyr Asn Trp Asn
1               5                  10                  15

Ser
```

<210> SEQ ID NO 15
<211> LENGTH: 18
<212> TYPE: PRT
<213> ORGANISM: Homo sapiens

<400> SEQUENCE: 15

```
Gly Ala Val Leu Val Gln Arg Glu Lys Asp Leu Pro Asn Tyr Asn Trp
1               5                  10                  15

Asn Ser
```

<210> SEQ ID NO 16
<211> LENGTH: 19
<212> TYPE: PRT
<213> ORGANISM: Homo sapiens

<400> SEQUENCE: 16

```
Gln Gly Ala Val Leu Val Gln Arg Glu Lys Asp Leu Pro Asn Tyr Asn
1               5                  10                  15

Trp Asn Ser
```

<210> SEQ ID NO 17
<211> LENGTH: 20
<212> TYPE: PRT
<213> ORGANISM: Homo sapiens -continued

```
<400> SEQUENCE: 17

Pro Gln Gly Ala Val Leu Val Gln Arg Glu Lys Asp Leu Pro Asn Tyr
1               5                   10                  15

Asn Trp Asn Ser
            20

<210> SEQ ID NO 18
<211> LENGTH: 21
<212> TYPE: PRT
<213> ORGANISM: Homo sapiens

<400> SEQUENCE: 18

Ala Pro Gln Gly Ala Val Leu Val Gln Arg Glu Lys Asp Leu Pro Asn
1               5                   10                  15

Tyr Asn Trp Asn Ser
            20

<210> SEQ ID NO 19
<211> LENGTH: 22
<212> TYPE: PRT
<213> ORGANISM: Homo sapiens

<400> SEQUENCE: 19

Pro Ala Pro Gln Gly Ala Val Leu Val Gln Arg Glu Lys Asp Leu Pro
1               5                   10                  15

Asn Tyr Asn Trp Asn Ser
            20

<210> SEQ ID NO 20
<211> LENGTH: 23
<212> TYPE: PRT
<213> ORGANISM: Homo sapiens

<400> SEQUENCE: 20

Ile Pro Ala Pro Gln Gly Ala Val Leu Val Gln Arg Glu Lys Asp Leu
1               5                   10                  15

Pro Asn Tyr Asn Trp Asn Ser
            20

<210> SEQ ID NO 21
<211> LENGTH: 24
<212> TYPE: PRT
<213> ORGANISM: Homo sapiens

<400> SEQUENCE: 21

Gln Ile Pro Ala Pro Gln Gly Ala Val Leu Val Gln Arg Glu Lys Asp
1               5                   10                  15

Leu Pro Asn Tyr Asn Trp Asn Ser
            20

<210> SEQ ID NO 22
<211> LENGTH: 25
<212> TYPE: PRT
<213> ORGANISM: Homo sapiens

<400> SEQUENCE: 22

Arg Gln Ile Pro Ala Pro Gln Gly Ala Val Leu Val Gln Arg Glu Lys
1               5                   10                  15

Asp Leu Pro Asn Tyr Asn Trp Asn Ser
            20                  25

<210> SEQ ID NO 23
```

```
<211> LENGTH: 26
<212> TYPE: PRT
<213> ORGANISM: Homo sapiens

<400> SEQUENCE: 23

Ser Arg Gln Ile Pro Ala Pro Gln Gly Ala Val Leu Val Gln Arg Glu
1               5                   10                  15

Lys Asp Leu Pro Asn Tyr Asn Trp Asn Ser
            20                  25

<210> SEQ ID NO 24
<211> LENGTH: 27
<212> TYPE: PRT
<213> ORGANISM: Homo sapiens

<400> SEQUENCE: 24

His Ser Arg Gln Ile Pro Ala Pro Gln Gly Ala Val Leu Val Gln Arg
1               5                   10                  15

Glu Lys Asp Leu Pro Asn Tyr Asn Trp Asn Ser
            20                  25

<210> SEQ ID NO 25
<211> LENGTH: 28
<212> TYPE: PRT
<213> ORGANISM: Homo sapiens

<400> SEQUENCE: 25

Pro His Ser Arg Gln Ile Pro Ala Pro Gln Gly Ala Val Leu Val Gln
1               5                   10                  15

Arg Glu Lys Asp Leu Pro Asn Tyr Asn Trp Asn Ser
            20                  25

<210> SEQ ID NO 26
<211> LENGTH: 29
<212> TYPE: PRT
<213> ORGANISM: Homo sapiens

<400> SEQUENCE: 26

Ala Pro His Ser Arg Gln Ile Pro Ala Pro Gln Gly Ala Val Leu Val
1               5                   10                  15

Gln Arg Glu Lys Asp Leu Pro Asn Tyr Asn Trp Asn Ser
            20                  25

<210> SEQ ID NO 27
<211> LENGTH: 30
<212> TYPE: PRT
<213> ORGANISM: Homo sapiens

<400> SEQUENCE: 27

Ser Ala Pro His Ser Arg Gln Ile Pro Ala Pro Gln Gly Ala Val Leu
1               5                   10                  15

Val Gln Arg Glu Lys Asp Leu Pro Asn Tyr Asn Trp Asn Ser
            20                  25                  30

<210> SEQ ID NO 28
<211> LENGTH: 31
<212> TYPE: PRT
<213> ORGANISM: Homo sapiens

<400> SEQUENCE: 28

Leu Ser Ala Pro His Ser Arg Gln Ile Pro Ala Pro Gln Gly Ala Val
1               5                   10                  15

Leu Val Gln Arg Glu Lys Asp Leu Pro Asn Tyr Asn Trp Asn Ser
```

-continued

```
<210> SEQ ID NO 29
<211> LENGTH: 32
<212> TYPE: PRT
<213> ORGANISM: Homo sapiens

<400> SEQUENCE: 29

Gly Leu Ser Ala Pro His Ser Arg Gln Ile Pro Ala Pro Gln Gly Ala
1               5                   10                  15

Val Leu Val Gln Arg Glu Lys Asp Leu Pro Asn Tyr Asn Trp Asn Ser
            20                  25                  30

<210> SEQ ID NO 30
<211> LENGTH: 33
<212> TYPE: PRT
<213> ORGANISM: Homo sapiens

<400> SEQUENCE: 30

Pro Gly Leu Ser Ala Pro His Ser Arg Gln Ile Pro Ala Pro Gln Gly
1               5                   10                  15

Ala Val Leu Val Gln Arg Glu Lys Asp Leu Pro Asn Tyr Asn Trp Asn
            20                  25                  30

Ser

<210> SEQ ID NO 31
<211> LENGTH: 34
<212> TYPE: PRT
<213> ORGANISM: Homo sapiens

<400> SEQUENCE: 31

Gln Pro Gly Leu Ser Ala Pro His Ser Arg Gln Ile Pro Ala Pro Gln
1               5                   10                  15

Gly Ala Val Leu Val Gln Arg Glu Lys Asp Leu Pro Asn Tyr Asn Trp
            20                  25                  30

Asn Ser

<210> SEQ ID NO 32
<211> LENGTH: 35
<212> TYPE: PRT
<213> ORGANISM: Homo sapiens

<400> SEQUENCE: 32

Gln Gln Pro Gly Leu Ser Ala Pro His Ser Arg Gln Ile Pro Ala Pro
1               5                   10                  15

Gln Gly Ala Val Leu Val Gln Arg Glu Lys Asp Leu Pro Asn Tyr Asn
            20                  25                  30

Trp Asn Ser
        35

<210> SEQ ID NO 33
<211> LENGTH: 36
<212> TYPE: PRT
<213> ORGANISM: Homo sapiens

<400> SEQUENCE: 33

Arg Gln Gln Pro Gly Leu Ser Ala Pro His Ser Arg Gln Ile Pro Ala
1               5                   10                  15

Pro Gln Gly Ala Val Leu Val Gln Arg Glu Lys Asp Leu Pro Asn Tyr
            20                  25                  30

Asn Trp Asn Ser
```

```
<210> SEQ ID NO 34
<211> LENGTH: 37
<212> TYPE: PRT
<213> ORGANISM: Homo sapiens

<400> SEQUENCE: 34

Ser Arg Gln Gln Pro Gly Leu Ser Ala Pro His Ser Arg Gln Ile Pro
1               5                   10                  15

Ala Pro Gln Gly Ala Val Leu Val Gln Arg Glu Lys Asp Leu Pro Asn
            20                  25                  30

Tyr Asn Trp Asn Ser
        35

<210> SEQ ID NO 35
<211> LENGTH: 38
<212> TYPE: PRT
<213> ORGANISM: Homo sapiens

<400> SEQUENCE: 35

Gly Ser Arg Gln Gln Pro Gly Leu Ser Ala Pro His Ser Arg Gln Ile
1               5                   10                  15

Pro Ala Pro Gln Gly Ala Val Leu Val Gln Arg Glu Lys Asp Leu Pro
            20                  25                  30

Asn Tyr Asn Trp Asn Ser
        35

<210> SEQ ID NO 36
<211> LENGTH: 39
<212> TYPE: PRT
<213> ORGANISM: Homo sapiens

<400> SEQUENCE: 36

Ser Gly Ser Arg Gln Gln Pro Gly Leu Ser Ala Pro His Ser Arg Gln
1               5                   10                  15

Ile Pro Ala Pro Gln Gly Ala Val Leu Val Gln Arg Glu Lys Asp Leu
            20                  25                  30

Pro Asn Tyr Asn Trp Asn Ser
        35

<210> SEQ ID NO 37
<211> LENGTH: 40
<212> TYPE: PRT
<213> ORGANISM: Homo sapiens

<400> SEQUENCE: 37

Ser Ser Gly Ser Arg Gln Gln Pro Gly Leu Ser Ala Pro His Ser Arg
1               5                   10                  15

Gln Ile Pro Ala Pro Gln Gly Ala Val Leu Val Gln Arg Glu Lys Asp
            20                  25                  30

Leu Pro Asn Tyr Asn Trp Asn Ser
        35                  40

<210> SEQ ID NO 38
<211> LENGTH: 41
<212> TYPE: PRT
<213> ORGANISM: Homo sapiens

<400> SEQUENCE: 38

Glu Ser Ser Gly Ser Arg Gln Gln Pro Gly Leu Ser Ala Pro His Ser
1               5                   10                  15
```

Arg Gln Ile Pro Ala Pro Gln Gly Ala Val Leu Val Gln Arg Glu Lys
            20                  25                  30

Asp Leu Pro Asn Tyr Asn Trp Asn Ser
        35                  40

<210> SEQ ID NO 39
<211> LENGTH: 42
<212> TYPE: PRT
<213> ORGANISM: Homo sapiens

<400> SEQUENCE: 39

Pro Glu Ser Ser Gly Ser Arg Gln Gln Pro Gly Leu Ser Ala Pro His
1               5                   10                  15

Ser Arg Gln Ile Pro Ala Pro Gln Gly Ala Val Leu Val Gln Arg Glu
            20                  25                  30

Lys Asp Leu Pro Asn Tyr Asn Trp Asn Ser
        35                  40

<210> SEQ ID NO 40
<211> LENGTH: 43
<212> TYPE: PRT
<213> ORGANISM: Homo sapiens

<400> SEQUENCE: 40

Pro Pro Glu Ser Ser Gly Ser Arg Gln Gln Pro Gly Leu Ser Ala Pro
1               5                   10                  15

His Ser Arg Gln Ile Pro Ala Pro Gln Gly Ala Val Leu Val Gln Arg
            20                  25                  30

Glu Lys Asp Leu Pro Asn Tyr Asn Trp Asn Ser
        35                  40

<210> SEQ ID NO 41
<211> LENGTH: 44
<212> TYPE: PRT
<213> ORGANISM: Homo sapiens

<400> SEQUENCE: 41

Pro Pro Pro Glu Ser Ser Gly Ser Arg Gln Gln Pro Gly Leu Ser Ala
1               5                   10                  15

Pro His Ser Arg Gln Ile Pro Ala Pro Gln Gly Ala Val Leu Val Gln
            20                  25                  30

Arg Glu Lys Asp Leu Pro Asn Tyr Asn Trp Asn Ser
        35                  40

<210> SEQ ID NO 42
<211> LENGTH: 45
<212> TYPE: PRT
<213> ORGANISM: Homo sapiens

<400> SEQUENCE: 42

Ser Pro Pro Pro Glu Ser Ser Gly Ser Arg Gln Gln Pro Gly Leu Ser
1               5                   10                  15

Ala Pro His Ser Arg Gln Ile Pro Ala Pro Gln Gly Ala Val Leu Val
            20                  25                  30

Gln Arg Glu Lys Asp Leu Pro Asn Tyr Asn Trp Asn Ser
        35                  40                  45

<210> SEQ ID NO 43
<211> LENGTH: 46
<212> TYPE: PRT
<213> ORGANISM: Homo sapiens -continued

<400> SEQUENCE: 43

Leu Ser Pro Pro Pro Glu Ser Ser Gly Ser Arg Gln Gln Pro Gly Leu
1               5                   10                  15

Ser Ala Pro His Ser Arg Gln Ile Pro Ala Pro Gln Gly Ala Val Leu
            20                  25                  30

Val Gln Arg Glu Lys Asp Leu Pro Asn Tyr Asn Trp Asn Ser
        35                  40                  45

<210> SEQ ID NO 44
<211> LENGTH: 47
<212> TYPE: PRT
<213> ORGANISM: Homo sapiens

<400> SEQUENCE: 44

Ser Leu Ser Pro Pro Pro Glu Ser Ser Gly Ser Arg Gln Gln Pro Gly
1               5                   10                  15

Leu Ser Ala Pro His Ser Arg Gln Ile Pro Ala Pro Gln Gly Ala Val
            20                  25                  30

Leu Val Gln Arg Glu Lys Asp Leu Pro Asn Tyr Asn Trp Asn Ser
        35                  40                  45

<210> SEQ ID NO 45
<211> LENGTH: 48
<212> TYPE: PRT
<213> ORGANISM: Homo sapiens

<400> SEQUENCE: 45

Thr Ser Leu Ser Pro Pro Pro Glu Ser Ser Gly Ser Arg Gln Gln Pro
1               5                   10                  15

Gly Leu Ser Ala Pro His Ser Arg Gln Ile Pro Ala Pro Gln Gly Ala
            20                  25                  30

Val Leu Val Gln Arg Glu Lys Asp Leu Pro Asn Tyr Asn Trp Asn Ser
        35                  40                  45

<210> SEQ ID NO 46
<211> LENGTH: 49
<212> TYPE: PRT
<213> ORGANISM: Homo sapiens

<400> SEQUENCE: 46

Gly Thr Ser Leu Ser Pro Pro Pro Glu Ser Ser Gly Ser Arg Gln Gln
1               5                   10                  15

Pro Gly Leu Ser Ala Pro His Ser Arg Gln Ile Pro Ala Pro Gln Gly
            20                  25                  30

Ala Val Leu Val Gln Arg Glu Lys Asp Leu Pro Asn Tyr Asn Trp Asn
        35                  40                  45

Ser

<210> SEQ ID NO 47
<211> LENGTH: 5
<212> TYPE: PRT
<213> ORGANISM: Artificial
<220> FEATURE:
<223> OTHER INFORMATION: Peptide corresponding to P moiety of formula
      (I) compound

<400> SEQUENCE: 47

Tyr Asn Trp Asn Ser
1               5

```
<210> SEQ ID NO 48
<211> LENGTH: 5
<212> TYPE: PRT
<213> ORGANISM: Artificial
<220> FEATURE:
<223> OTHER INFORMATION: Peptide corresponding to P moiety of formula
      (I) compound

<400> SEQUENCE: 48

Tyr Lys Trp Asn Ser
1               5

<210> SEQ ID NO 49
<211> LENGTH: 5
<212> TYPE: PRT
<213> ORGANISM: Artificial
<220> FEATURE:
<223> OTHER INFORMATION: Peptide corresponding to P moiety of formula
      (I) compound

<400> SEQUENCE: 49

Tyr Asp Trp Asn Ser
1               5

<210> SEQ ID NO 50
<211> LENGTH: 5
<212> TYPE: PRT
<213> ORGANISM: Artificial
<220> FEATURE:
<223> OTHER INFORMATION: Peptide corresponding to P moiety of formula
      (I) compound

<400> SEQUENCE: 50

Tyr Tyr Trp Asn Ser
1               5

<210> SEQ ID NO 51
<211> LENGTH: 5
<212> TYPE: PRT
<213> ORGANISM: Artificial
<220> FEATURE:
<223> OTHER INFORMATION: Peptide corresponding to P moiety of formula
      (I) compound

<400> SEQUENCE: 51

Tyr Leu Trp Asn Ser
1               5

<210> SEQ ID NO 52
<211> LENGTH: 5
<212> TYPE: PRT
<213> ORGANISM: Artificial
<220> FEATURE:
<223> OTHER INFORMATION: Peptide corresponding to P moiety of formula
      (I) compound

<400> SEQUENCE: 52

Tyr Asn Ala Asn Ser
1               5

<210> SEQ ID NO 53
<211> LENGTH: 5
<212> TYPE: PRT
<213> ORGANISM: Artificial
<220> FEATURE:
<223> OTHER INFORMATION: Peptide corresponding to P moiety of formula
      (I) compound

<400> SEQUENCE: 53
```

```
Tyr Asn Leu Asn Ser
1               5

<210> SEQ ID NO 54
<211> LENGTH: 5
<212> TYPE: PRT
<213> ORGANISM: Artificial
<220> FEATURE:
<223> OTHER INFORMATION: Peptide corresponding to P moiety of formula
      (I) compound

<400> SEQUENCE: 54

Tyr Asn Ser Asn Ser
1               5

<210> SEQ ID NO 55
<211> LENGTH: 5
<212> TYPE: PRT
<213> ORGANISM: Artificial
<220> FEATURE:
<223> OTHER INFORMATION: Peptide corresponding to P moiety of formula
      (I) compound

<400> SEQUENCE: 55

Tyr Asn Asp Asn Ser
1               5

<210> SEQ ID NO 56
<211> LENGTH: 5
<212> TYPE: PRT
<213> ORGANISM: Artificial
<220> FEATURE:
<223> OTHER INFORMATION: Peptide corresponding to P moiety of formula
      (I) compound

<400> SEQUENCE: 56

Tyr Asn Lys Asn Ser
1               5

<210> SEQ ID NO 57
<211> LENGTH: 5
<212> TYPE: PRT
<213> ORGANISM: Artificial
<220> FEATURE:
<223> OTHER INFORMATION: Peptide corresponding to P moiety of formula
      (I) compound

<400> SEQUENCE: 57

Ala Asn Trp Asn Ser
1               5

<210> SEQ ID NO 58
<211> LENGTH: 5
<212> TYPE: PRT
<213> ORGANISM: Artificial
<220> FEATURE:
<223> OTHER INFORMATION: Peptide corresponding to P moiety of formula
      (I) compound

<400> SEQUENCE: 58

Leu Asn Trp Asn Ser
1               5

<210> SEQ ID NO 59
<211> LENGTH: 5
<212> TYPE: PRT
<213> ORGANISM: Artificial
<220> FEATURE:
<223> OTHER INFORMATION: Peptide corresponding to P moiety of formula
```

```
                                -continued
          (I) compound

<400> SEQUENCE: 59

Ser Asn Trp Asn Ser
1               5

<210> SEQ ID NO 60
<211> LENGTH: 5
<212> TYPE: PRT
<213> ORGANISM: Artificial
<220> FEATURE:
<223> OTHER INFORMATION: Peptide corresponding to P moiety of formula
      (I) compound

<400> SEQUENCE: 60

Asp Asn Trp Asn Ser
1               5

<210> SEQ ID NO 61
<211> LENGTH: 5
<212> TYPE: PRT
<213> ORGANISM: Artificial
<220> FEATURE:
<223> OTHER INFORMATION: Peptide corresponding to P moiety of formula
      (I) compound

<400> SEQUENCE: 61

Lys Asn Trp Asn Ser
1               5

<210> SEQ ID NO 62
<211> LENGTH: 5
<212> TYPE: PRT
<213> ORGANISM: Artificial
<220> FEATURE:
<223> OTHER INFORMATION: Peptide corresponding to P moiety of formula
      (I) compound
<220> FEATURE:
<221> NAME/KEY: SITE
<222> LOCATION: (3)..(3)
<223> OTHER INFORMATION: Xaa stands for N(in)-formyltriptophan.

<400> SEQUENCE: 62

Tyr Asn Xaa Asn Ser
1               5

<210> SEQ ID NO 63
<211> LENGTH: 5
<212> TYPE: PRT
<213> ORGANISM: Artificial
<220> FEATURE:
<223> OTHER INFORMATION: Peptide corresponding to P moiety of formula
      (I) compound
<220> FEATURE:
<221> NAME/KEY: SITE
<222> LOCATION: (1)..(2)
<223> OTHER INFORMATION: Amide bond between Tyr and Asn is substituted
      with -CH2NH- bond.

<400> SEQUENCE: 63

Tyr Asn Trp Asn Ser
1               5

<210> SEQ ID NO 64
<211> LENGTH: 4
<212> TYPE: PRT
<213> ORGANISM: Artificial
<220> FEATURE:
<223> OTHER INFORMATION: Peptide corresponding to P moiety of formula
      (I) compound
```

```
<220> FEATURE:
<221> NAME/KEY: SITE
<222> LOCATION: (1)..(1)
<223> OTHER INFORMATION: Asn protected by Fmoc

<400> SEQUENCE: 64

Xaa Trp Asn Ser
1

<210> SEQ ID NO 65
<211> LENGTH: 5
<212> TYPE: PRT
<213> ORGANISM: Homo sapiens

<400> SEQUENCE: 65

Phe Gly Leu Arg Trp
1               5

<210> SEQ ID NO 66
<211> LENGTH: 5
<212> TYPE: PRT
<213> ORGANISM: Artificial
<220> FEATURE:
<223> OTHER INFORMATION: Peptide moiety of compound 1
<220> FEATURE:
<221> NAME/KEY: SITE
<222> LOCATION: (1)..(1)
<223> OTHER INFORMATION: Phe has 4-fluorobenzoyl group.
<220> FEATURE:
<221> NAME/KEY: SITE
<222> LOCATION: (5)..(5)
<223> OTHER INFORMATION: Typ has NH2 group.

<400> SEQUENCE: 66

Phe Gly Leu Arg Trp
1               5

<210> SEQ ID NO 67
<211> LENGTH: 54
<212> TYPE: PRT
<213> ORGANISM: Homo sapiens

<400> SEQUENCE: 67

Gly Thr Ser Leu Ser Pro Pro Pro Glu Ser Ser Gly Ser Arg Gln Gln
1               5                   10                  15

Pro Gly Leu Ser Ala Pro His Ser Arg Gln Ile Pro Ala Pro Gln Gly
            20                  25                  30

Ala Val Leu Val Gln Arg Glu Lys Asp Leu Pro Asn Tyr Asn Trp Asn
        35                  40                  45

Ser Phe Gly Leu Arg Phe
    50
```

METASTIN DERIVATIVE AND USE THEREOF

CROSS-REFERENCE TO RELATED APPLICATIONS

This application is the U.S. national phase application, pursuant to 35 U.S.C. §371, of PCT International Application No. PCT/JP2009/058409, filed Apr. 28, 2009, which claims the benefit of Japanese Application No. 119235/2008, filed Apr. 30, 2008, the contents of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Apr. 22, 2013, is named 87431_46590-Sequence-Listing_ST25.txt and is 25,560 bytes in size.

TECHNICAL FIELD

The present invention relates to a metastin derivative and use thereof.

BACKGROUND OF THE INVENTION

Many hormones and neurotransmitters control functions of the body through specific receptors present in the cellular membrane. Many of these receptors perform intracellular signal transduction by activation of coupled guanine nucleotide-binding proteins (hereinafter to be abbreviated as G protein). Moreover, since these receptors have a common structure having a 7-transmembrane domain, they are generically referred to as G protein-coupled receptors or 7-transmembrane receptors.

As one of these G protein-coupled receptor proteins, a human receptor protein encoded by GPR54 gene is known [non-patent document 1].

In addition, as a bioactive peptide functionable as a ligand for the above-mentioned GPR54, metastin (aka kisspeptin) is known [non-patent document 2].

Cancer metastasis is a key factor that determines the life expectancy of patients. Metastin acting as a GPR54 agonist is known to suppress metastasis of lung transitional GPR54-expressing melanoma [non-patent document 2].

Likewise, it has been clarified that metastin also suppresses metastasis of GPR54-expressing pancreatic cancer cells [non-patent document 3]. On the other hand, it has recently been clarified one after another that release of sex hormone such as gonadotropin and the like when agonist acts on intracerebral GPR54 [non-patent document 4], and loss of function of GPR54 causes deficiency of sexual function [non-patent document 5]. As mentioned above, the metastin/GPR54 system is a highly attractive drug discovery target for both the suppression of cancer metastasis and sexual functional diseases.

The present inventors have found that a pentapeptide derivative having a bis-2-picolylamino group or a guanide group as a basic functional group at the N-terminal is a GPR54 agonist [non-patent document 6]. In addition, they have found that a ligand having a 4-fluorobenzoyl group at the N-terminal shows the highest bioactivity from among the compounds reported to show an agonist activity, and obtained information relating to the structure and activity thereof by conducting studies of the quantitative structure-activity relationship [non-patent document 7]. Furthermore, they have found that pentapeptide modified to have, at the N-terminal, (i) an aryl group or an aryl group having electron-withdrawing properties as a whole, (ii) a substituted or unsubstituted aromatic heterocyclic group containing at least one kind of hetero atom selected from the group consisting of a nitrogen atom, an oxygen atom and a sulfur atom, or (iii) an aryl group substituted by 1 to 3 electron-donating groups selected from the group consisting of a lower alkoxy group, a hydroxy lower alkyl group, an amino lower alkyl group, a lower alkanoylamino lower alkyl group, a hydroxy-substituted phenylcarbonyloxy group, an amino group and a hydroxyl group has superior GPR54 agonist activity [patent document 1].

On the other hand, metastin-related peptide has been reported to show decomposition of a peptide bond between Gly-Leu dipeptides on the C-terminal by plural matrix metalloproteinases (MMP), and a combined use with an MMP inhibitor or use of a metastin derivative free of decomposition by MMP is suggested to be necessary in consideration of the clinical application of metastin-related peptide [non-patent document 8].

PRIOR ART DOCUMENTS

Patent Document patent document 1: WO 2007/125619

Non-Patent Documents non-patent document 1: FEBS Letters, vol. 446, page 103-107 (1999)
non-patent document 2: Nature, vol. 411, page 613-617 (2001)
non-patent document 3: Biochemical and Biophysical Research Communications, vol. 315, page 85-92 (2004)
non-patent document 4: Trends in Endocrinology and Metabolism, vol. 16, page 249-250 (2005)
non-patent document 5: The New England Journal of Medicine, vol. 349, page 1614-1627 (2003)
non-patent document 6: Bioorganic and Medicinal Chemistry Letters, vol. 16, page 134-137 (2006)
non-patent document 7: Journal of Medicinal Chemistry, vol. 50, page 3222-3228 (2007)
non-patent document 8: Oncogene, vol. 22, page 4617-4626 (2003)

SUMMARY OF THE INVENTION

Problems to be Solved by the Invention

The present invention mainly aims to provide a compound (metastin derivative) having superior GPR54 agonist activity, which resists decomposition in the serum, and a pharmaceutical composition containing the compound.

Means of Solving the Problems

The present inventors have conducted intensive studies in view of the aforementioned problems and succeeded in obtaining a metastin derivative which maintains superior GPR54 agonist activity and resists decomposition in the serum, by substituting the moieties assumed to trigger decomposition in the serum with various peptide mimetics, and further found use thereof, which resulted in the completion of the present invention.

Accordingly, the present invention provides the following compound and use of a pharmaceutical composition containing the compound.

[1] A metastin derivative (I) represented by the formula (I)

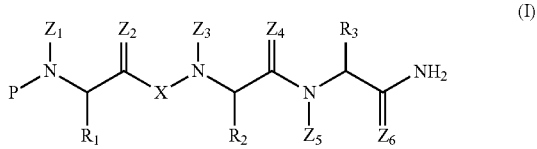

wherein $Z_1$, $Z_3$ and $Z_5$ are the same or different and each is a hydrogen atom or $C_{1-3}$ alkyl, $Z_2$, $Z_4$ and $Z_6$ are the same or different and each is a hydrogen atom, O or S, $R_1$ is $C_{1-4}$ alkyl optionally substituted by substituent(s) selected from the group consisting of (1) an optionally substituted $C_{6-12}$ aromatic hydrocarbon group, (2) an optionally substituted 5- to 14-membered aromatic heterocyclic group consisting of 1 to 7 carbon atoms and a hetero atom selected from the group consisting of a nitrogen atom, an oxygen atom and a sulfur atom, (3) an optionally substituted $C_{8-14}$ aromatic fused ring group, (4) an optionally substituted 5- to 14-membered aromatic fused heterocyclic group consisting of 3 to 11 carbon atoms and a hetero atom selected from the group consisting of a nitrogen atom, an oxygen atom and a sulfur atom, (5) an optionally substituted nonaromatic cyclic hydrocarbon group having a carbon number of not more than 7, and (6) an optionally substituted nonaromatic heterocyclic group having a carbon number of not more than 7, $R_2$ is (1) $C_{1-8}$ alkyl having an optionally substituted basic group, and optionally further having other substituent(s), (2) aralkyl having an optionally substituted basic group, and optionally further having other substituent(s), (3) $C_{1-4}$ alkyl having a nonaromatic cyclic hydrocarbon group having an optionally substituted basic group and a carbon number of not more than 7, and optionally further having other substituent(s), or (4) $C_{1-4}$ alkyl having a nonaromatic heterocyclic group having an optionally substituted basic group and a carbon number of not more than 7, and optionally further having other substituent(s), $R_3$ is $C_{1-4}$ alkyl optionally substituted by substituent(s) selected from the group consisting of (1) an optionally substituted $C_{6-12}$ aromatic hydrocarbon group, (2) an optionally substituted 5- to 14-membered aromatic heterocyclic group consisting of 1 to 7 carbon atoms and a hetero atom selected from the group consisting of a nitrogen atom, an oxygen atom and a sulfur atom, (3) an optionally substituted $C_{8-14}$ aromatic fused ring group, (4) an optionally substituted 5- to 14-membered aromatic fused heterocyclic group consisting of 3 to 11 carbon atoms and a hetero atom selected from the group consisting of a nitrogen atom, an oxygen atom and a sulfur atom, (5) an optionally substituted nonaromatic cyclic hydrocarbon group having a carbon number of not more than 7, and (6) an optionally substituted nonaromatic heterocyclic group having a carbon number of not more than 7, X is a group represented by the formula (II)

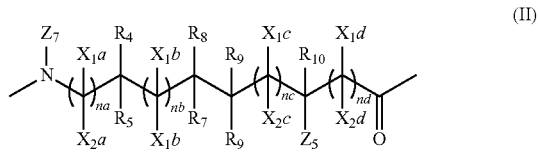

wherein na-nd are the same or different and each is an integer of 0-2 (wherein the total of na, nb, nc and nd is 0-2), $X_1a$-$X_1d$ and $X_2a$-$X_2d$ are the same or different and each is a hydrogen atom, hydroxy, a halogen atom or an optionally substituted lower alkyl group, $Z_7$ is a hydrogen atom or an optionally substituted hydrocarbon group, $R_4$-$R_{11}$ are the same or different and each is a hydrogen atom, hydroxy, a halogen atom, or optionally substituted lower alkyl, $R_7$ and $R_8$ in combination optionally form a bond, and $R_9$ and $R_{10}$ in combination optionally form a bond, P is (1) a hydrogen atom, (2) any amino acid residues bound to each other contiguously or non-contiguously from the C-terminal side of the 1st-49th amino acid sequence of the amino acid sequence shown by SEQ ID NO: 67, (3) a group represented by the formula

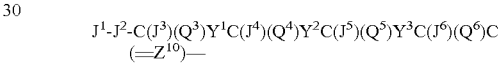

wherein $J^1$ is (a) a hydrogen atom or (b) (i) $C_{1-15}$ acyl, (ii) $C_{1-15}$ alkyl, (iii) $C_{6-14}$ aryl, (iv) carbamoyl, (v) carboxyl, (vi) sulfino, (vii) amidino or (viii) glyoxyloyl, each of which is optionally substituted by substituent(s) containing a ring group optionally having substituent(s), $J^2$ is (i) NH optionally substituted by $C_{1-6}$ alkyl, (ii) $CH_2$ optionally substituted by $C_{1-6}$ alkyl, (iii) O or (iv) S, $J^3$-$J^6$ are each a hydrogen atom or $C_{1-3}$ alkyl, $Q^3$-$Q^6$ are each $C_{1-4}$ alkyl optionally having substituent(s) selected from the group consisting of (i) an optionally substituted $C_{6-12}$ aromatic hydrocarbon group, (ii) an optionally substituted 5- to 14-membered aromatic heterocyclic group consisting of 1 to 7 carbon atoms and a hetero atom selected from the group consisting of a nitrogen atom, an oxygen atom and a sulfur atom, (iii) an optionally substituted $C_{8-14}$ aromatic fused ring group, (iv) an optionally substituted 5- to 14-membered aromatic fused heterocyclic group consisting of 3 to 11 carbon atoms and a hetero atom selected from the group consisting of a nitrogen atom, an oxygen atom and a sulfur atom, (v) an optionally substituted nonaromatic cyclic hydrocarbon group having a carbon number of not more than 7, (vi) an optionally substituted nonaromatic heterocyclic group having a carbon number of not more than 7, (vii) optionally substituted amino, (viii) optionally substituted guanidino, (ix) optionally substituted hydroxy, (x) optionally substituted carboxyl, (xi) optionally substituted carbamoyl, and (xii) optionally substituted sulfhydryl or a hydrogen atom, $J^3$ and $Q^3$, $J^4$ and $Q^4$, $J^5$ and $Q^5$, or $J^6$ and $Q^6$ may be bonded, or $J^2$ and $Q^3$, $Y^1$ and $Q^4$, $Y^2$ and $Q^5$, or $Y^3$ and $Q^6$ may be bonded to form a ring, $Y^1$-$Y^3$ are each a group represented by —CON($J^{13}$)-, —CSN($J^{13}$)-, —C($J^{14}$)N($J^{13}$) or —N($J^{13}$)CO— ($J^{13}$ and $J^{14}$ are each a hydrogen atom or $C_{1-3}$ alkyl), $Z^{10}$ is a hydrogen atom, O or S, (4) a group represented by the formula

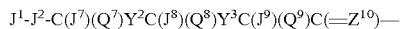

wherein $J^1$ and $J^2$ are each as defined above,
$J^7$-$J^9$ are as defined for $J^3$,
$Q^7$-$Q^9$ are as defined for $Q^3$,
$Y^2$ and $Y^3$ are as defined above,
$Z^{10}$ is as defined above,
$J^7$ and $Q^7$, $J^8$ and $Q^8$, or $J^9$ and $Q^9$ may be bonded, or $J^2$ and $Q^7$, $Y^2$ and $Q^8$, or $Y^3$ and $Q^9$ may be bonded to form a ring, (5) a group represented by the formula

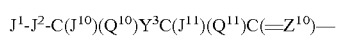

wherein $J^1$ and $J^2$ are as defined above,
$J^{10}$ and $J^{11}$ are as defined for $J^3$,
$Q^{10}$ and $Q^{11}$ are as defined for $Q^3$,
$Y^3$ is as defined above,
$Z^{10}$ is as defined above,
$J^{10}$ and $Q^{10}$, or $J^{11}$ and $Q^{11}$ may be bonded, or $J^2$ and $Q^{10}$, or $Y^3$ and $Q^{11}$ may be bonded to form a ring, (6) a group represented by the formula $J^1$-$J^2$-C($J^{12}$)($Q^{12}$)C(=$Z^{10}$)— wherein $J^1$ and $J^2$ are as defined above,
$J^{12}$ is as defined for $J^3$,
$Q^{12}$ is as defined for $Q^3$,
$Z^{10}$ is as defined above,
$J^{12}$ and $Q^{12}$ may be bonded, or $J^2$ and $Q^{12}$ may be bonded to form a ring, or (7) a group represented by the formula $J^1$- ($J^1$ is as defined above), or a salt thereof.

[2] The metastin derivative (I) according to [1], which is
(i) 4-fluorobenzoyl-Phe-X-Arg-Trp-NH$_2$(SEQ ID NO: 68),
(ii) D-Tyr-Asn-Trp-Asn-Ser-Phe-X-Arg-Trp-NH$_2$,
(iii) 3-(3-indolyl)propionyl-Asn-Ser-Phe-X-Arg-Trp-NH$_2$ (SEQ ID NO: 69),
(iv) 3-phenylpropionyl-Asn-Ser-Phe-X-Arg-Trp-NH$_2$(SEQ ID NO: 70),
(v) 2-(indol-3-yl)ethylcarbamoyl-Asn-Ser-Phe-X-Arg-Trp-NH$_2$(SEQ ID NO: 71),
(vi) D-Tyr-Asn-Pya(4)-Asn-Ser-Phe-X-Arg-Trp-NH$_2$,
(vii) TyrΨ(CH$_2$NH)Asn-D-Trp-Asn-Ser-Phe-X-Arg-Trp-NH$_2$,
(viii) D-Tyr-D-Asn-Pya(4)-Asn-Ser-Phe-X-Arg-Trp-NH$_2$,
(ix) D-Tyr-D-Pya(4)-Asn-Ser-Phe-X-Arg-Trp-NH$_2$,
(x) 3-pyridylpropionyl-Asn-Ser-Phe-X-Arg-Trp-NH$_2$(SEQ ID NO: 72),
(xi) 4-imidazoleacetyl-Asn-Ser-Phe-X-Arg-Trp-NH$_2$(SEQ ID NO: 73),
(xii) 4-nitrobenzoyl-Phe-X-Arg-Trp-NH$_2$(SEQ ID NO: 74),
(xiii) 4-(aminomethyl)benzoyl-Phe-X-Arg-Trp-NH$_2$(SEQ ID NO: 75),
(xiv) pyridine-2-carbonyl-Phe-X-Arg-Trp-NH$_2$(SEQ ID NO: 76),
(xv) benzoyl-Phe-X-Arg-Trp-NH$_2$(SEQ ID NO: 77),
(xvi) 4-(bis-picolylaminomethyl)benzoyl-Phe-X-Arg-Trp-NH$_2$(SEQ ID NO: 78), or
(xvii) 4-(guanidinomethyl)benzoyl-Phe-X-Arg-Trp-NH$_2$ (SEQ ID NO: 79),
or a salt thereof.

[3] The metastin derivative (I) according to [1], wherein X is the formula (III)

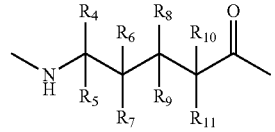

wherein $R_4$-$R_{11}$ are the same or different and each is a hydrogen atom, hydroxy, a halogen atom or optionally substituted lower alkyl, $R_7$ and $R_8$ in combination optionally form a bond, and $R_9$ and $R_{10}$ in combination optionally form a bond, or a salt thereof.

[4] The metastin derivative (I) according to [1], wherein X is selected from the group consisting of (IV)

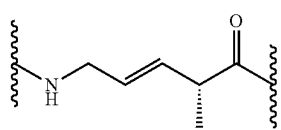

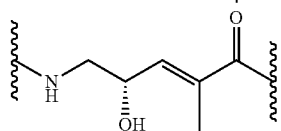

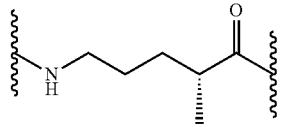

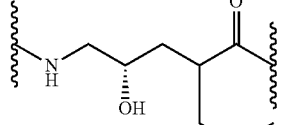

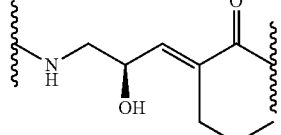

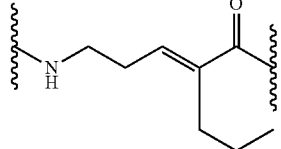

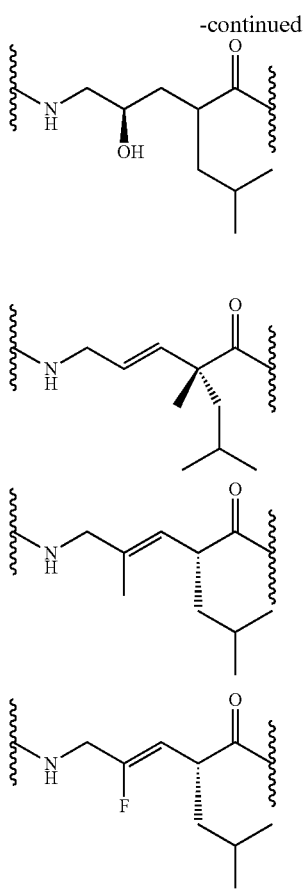

(group (IV)), or a salt thereof.

[5] A prodrug of the metastin derivative (I) according to [1] or a salt thereof.

[6] A pharmaceutical composition comprising the metastin derivative (I) according to [1] or a salt thereof or a prodrug thereof.

[7] The pharmaceutical composition according to [6], which is a cancer metastasis suppressant, an agent for the prophylaxis or treatment of cancer, or a cancer growth suppressant.

[8] The pharmaceutical composition according to [6], which is a pancreatic function regulator, an agent for the prophylaxis or treatment of acute or chronic pancreatitis or pancreatic cancer, a placental function regulator, an agent for the prophylaxis or treatment of villous cancer, hydatidiform mole, invasive mole, miscarriage, fetus underdevelopment, glucose metabolism disorder, abnormal lipid metabolism or induction of childbirth, a gonadal function improver, an agent for the prophylaxis or treatment of hormone-dependent cancer, infertility, endometriosis or hysteromyoma, inducing or stimulating ovulation, gonadotropic hormone secretagogue or sex hormone secretagogue, and an agent for the prophylaxis or treatment of Alzheimer's disease or mild cognitive impairment.

[9] A method of suppressing cancer metastasis, a method for the prophylaxis or treatment of cancer, or a method of suppressing cancer growth, comprising administering an effective amount of the metastin derivative (I) according to [1] or a salt thereof as an active ingredient to a subject of administration.

[10] A method of regulating pancreatic function, a method for the prophylaxis or treatment of acute or chronic pancreatitis or pancreatic cancer, a method of regulating placental function, a method for the prophylaxis or treatment of villous cancer, hydatidiform mole, invasive mole, miscarriage, fetus underdevelopment, glucose metabolism disorder, abnormal lipid metabolism or induction of childbirth, a method of improving gonadal function, a method for the prophylaxis or treatment of hormone-dependent cancer, infertility, endometriosis or hysteromyoma, a method of inducing or stimulating ovulation, a method of enhancing secretion of gonadotropic hormone or sex hormone, or a method for the prophylaxis or treatment of Alzheimer's disease or mild cognitive impairment, comprising administering an effective amount of the metastin derivative (I) according to [1] or a salt thereof as an active ingredient to a subject of administration.

Effect of the Invention

According to the present invention, a compound having a superior GPR54 agonist activity, which resists easy decomposition in the serum, and a pharmaceutical composition containing the compound can be provided.

The peptide descried in the present specification has an N-terminal (amino terminal) on the left end and a C-terminal (carboxyl terminal) on the right end, according to the conventional methods of peptide marking.

1. Compound Having GPR54 Agonist Activity

The compound of the present invention is represented by the following formula (I).

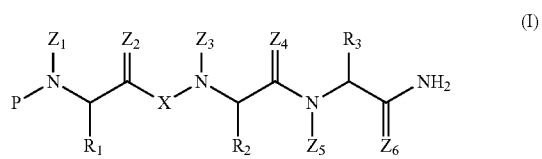

As for $Z_1$-$Z_6$ $Z_1$, $Z_3$ and $Z_5$ are the same or different and each is a hydrogen atom or $C_{1-3}$ alkyl, and $Z_2$, $Z_4$ and $Z_6$ are the same or different and each is a hydrogen atom, O or S. As the "$C_{1-3}$ alkyl", methyl, ethyl, propyl or isopropyl is used. As a combination of $Z_1$-$Z_6$, preferred is when $Z_1$ is a hydrogen atom, $Z_3$ is a hydrogen atom, $Z_5$ is a hydrogen atom or $C_{1-3}$ alkyl, and $Z_2$, $Z_4$ and $Z_6$ are each O or S. As a more preferable combination of $Z_1$-$Z_6$, preferred are when (a) $Z_1$ is a hydrogen atom, $Z_3$ is a hydrogen atom, $Z_5$ is a hydrogen atom, $Z_2$ is O, $Z_4$ is O, and $Z_6$ is O, (b) $Z_1$ is a hydrogen atom, $Z_3$ is a hydrogen atom, $Z_5$ is a hydrogen atom, $Z_2$ is O, $Z_4$ is O, and $Z_6$ is S, (c) $Z_1$ is a hydrogen atom, $Z_3$ is a hydrogen atom, $Z_5$ is methyl, $Z_2$ is O, $Z_4$ is O, $Z_6$ is O, and the like. Of these, cases (a) and (b) are preferable.

$Z_2$ being a hydrogen atom intends

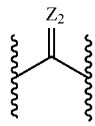

is —$CH_2$—. Likewise, $Z_4$ being a hydrogen atom intends

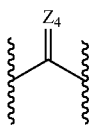

is —$CH_2$—, and $Z_6$ being a hydrogen atom intends

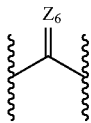

is —$CH_2$—.

As for $R_1$ $R_1$ is $C_{1-4}$ alkyl optionally substituted by substituent(s) selected from the group consisting of (1) an optionally substituted $C_{6-12}$ aromatic hydrocarbon group, (2) an optionally substituted 5- to 14-membered aromatic heterocyclic group consisting of 1 to 7 carbon atoms and a hetero atom selected from the group consisting of a nitrogen atom, an oxygen atom and a sulfur atom, (3) an optionally substituted $C_{8-14}$ aromatic fused ring group, (4) an optionally substituted 5- to 14-membered aromatic fused heterocyclic group consisting of 3 to 11 carbon atoms and a hetero atom selected from the group consisting of a nitrogen atom, an oxygen atom and a sulfur atom, (5) an optionally substituted nonaromatic cyclic hydrocarbon group having a carbon number of not more than 7, and (6) an optionally substituted nonaromatic heterocyclic group having a carbon number of not more than 7.

As the "$C_{1-4}$ alkyl", for example, methyl, ethyl, propyl, isopropyl, butyl, isobutyl, sec-butyl, tert-butyl and the like are used.

As the "$C_{6-12}$ aromatic hydrocarbon group", for example, a monocyclic $C_{6-12}$ aromatic hydrocarbon group such as phenyl, cyclooctatetraenyl etc., and the like are used.

As the "5- to 14-membered aromatic heterocyclic group consisting of 1 to 7 carbon atoms and a hetero atom selected from the group consisting of a nitrogen atom, an oxygen atom and a sulfur atom", for example, a 5- to 14-membered, preferably 5- to 10-membered, more preferably 5- or 6-membered, monocyclic aromatic heterocyclic group containing, besides 1 to 7 carbon atoms, one or two kinds of 1 to 4 hetero atoms selected from a nitrogen atom, a sulfur atom and an oxygen atom is used. Specifically, for example, thienyl (e.g., 2-thienyl, 3-thienyl), furyl (e.g., 2-furyl, 3-furyl), pyridyl (e.g., 2-pyridyl, 3-pyridyl, 4-pyridyl), thiazolyl (e.g., 2-thiazolyl, 4-thiazolyl, 5-thiazolyl), oxazolyl (e.g., 2-oxazolyl, 4-oxazolyl), pyrazinyl, pyrimidinyl (e.g., 2-pyrimidinyl, 4-pyrimidinyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), pyridazinyl (e.g., 3-pyridazinyl, 4-pyridazinyl), isothiazolyl (e.g., 3-isothiazolyl), isoxazolyl (e.g., 3-isoxazolyl) and the like are used.

As the "$C_{8-14}$ aromatic fused ring group", for example, naphthyl (e.g., 1-naphthyl, 2-naphthyl), anthryl (e.g., 2-anthryl, 9-anthryl) and the like are used.

As the "5- to 14-membered aromatic fused heterocyclic group consisting of 3 to 11 carbon atoms, and a hetero atom selected from the group consisting of a nitrogen atom, an oxygen atom and a sulfur atom", for example, a 5- to 14-membered (preferably 5- to 10-membered) bicyclic or tricyclic aromatic heterocyclic group containing, besides 3 to 11 carbon atoms, one or two kinds of 1 to 4 hetero atoms selected from a nitrogen atom, a sulfur atom and an oxygen atom, or a monovalent group obtained by removing any one hydrogen atom from a 5- to 14-membered (preferably 5- to 10-membered) 7- to 10-membered aromatic crosslinked heterocycle containing, besides carbon atoms, one or two kinds of 1 to 4 hetero atoms selected from a nitrogen atom, a sulfur atom and an oxygen atom is used. Specifically, for example, quinolyl (e.g., 2-quinolyl, 3-quinolyl, 4-quinolyl, 5-quinolyl, 8-quinolyl), isoquinolyl (e.g., 1-isoquinolyl, 3-isoquinolyl, 4-isoquinolyl, 5-isoquinolyl), indolyl (e.g., 1-indolyl, 2-indolyl, 3-indolyl), 2-benzothiazolyl, benzo[b]thienyl, (e.g., 2-benzo[b]thienyl, 3-benzo[b]thienyl), benzo[b]furanyl (e.g., 2-benzo[b]furanyl, 3-benzo[b]furanyl) and the like are used.

As the "nonaromatic cyclic hydrocarbon group having a carbon number of not more than 7", for example, a $C_{3-7}$ cycloalkyl group such as cyclopropyl, cyclobutyl, cyclopentyl, cyclohexyl etc., and the like are used.

As the "nonaromatic heterocyclic group having a carbon number of not more than 7", a 5- to 10-membered nonaromatic heterocyclic group containing, besides 1 to 7 carbon atoms, one or two kinds of 1 to 4 hetero atoms selected from a nitrogen atom, a sulfur atom and an oxygen atom such as pyrrolidinyl (e.g., 1-pyrrolidinyl, 2-pyrrolidinyl, 3-pyrrolidinyl), oxazolidinyl (e.g., 2-oxazolidinyl), imidazolinyl (e.g., 1-imidazolinyl, 2-imidazolinyl, 4-imidazolinyl), piperidinyl (e.g., 1-piperidinyl, 2-piperidinyl, 3-piperidinyl, 4-piperidinyl), piperazinyl (e.g., 1-piperazinyl, 2-piperazinyl), morpholino, thiomorpholino etc., and the like are used.

As the substituents of the "$C_{6-12}$ aromatic hydrocarbon group", "5- to 14-membered aromatic heterocyclic group consisting of 1 to 7 carbon atoms and a hetero atom selected from the group consisting of a nitrogen atom, an oxygen atom and a sulfur atom", "$C_{8-14}$ aromatic fused ring group", "5- to 14-membered aromatic fused heterocyclic group consisting of 3 to 11 carbon atoms and a hetero atom selected from the group consisting of a nitrogen atom, an oxygen atom and a sulfur atom", "nonaromatic cyclic hydrocarbon group having a carbon number of not more than 7" and "nonaromatic heterocyclic group having a carbon number of not more than 7", for example, a substituent selected from (1) oxo, (2) a halogen atom (e.g., fluorine, chlorine, bromine, iodine etc.), (3) $C_{1-3}$ alkylenedioxy (e.g., methylenedioxy, ethylenedioxy etc.), (4) nitro, (5) cyano, (6) optionally substituted $C_{1-6}$ alkyl, (7) optionally substituted $C_{2-6}$ alkenyl, (8) optionally substituted $C_{2-6}$ alkynyl, (9) optionally substituted $C_{3-8}$ cycloalkyl,

(10) optionally substituted $C_{6-14}$ aryl,

(11) optionally substituted $C_{7-16}$ aralkyl,

(12) optionally substituted $C_{1-6}$ alkoxy,

(13) hydroxy,

(14) optionally substituted $C_{6-14}$ aryloxy,

(15) optionally substituted $C_{7-16}$ aralkyloxy,

(16) mercapto,

(17) optionally substituted $C_{1-6}$ alkylthio,

(18) optionally substituted $C_{6-14}$ arylthio,
(19) optionally substituted $C_{7-16}$ aralkylthio,
(20) optionally substituted amino [amino, optionally substituted mono- or di-$C_{1-6}$ alkyl-amino (e.g., methylamino, dimethylamino, ethylamino, diethylamino, propylamino, isopropylamino etc.), optionally substituted mono- or di-$C_{2-6}$ alkenyl-amino (e.g., vinylamino, propenylamino, isopropenylamino), optionally substituted $C_{2-6}$ alkynyl-amino (e.g., 2-butyn-1-yl-amino, 4-pentyn-1-yl-amino, 5-hexin-1-yl-amino), optionally substituted mono- or di-$C_{3-8}$ cycloalkyl-amino (e.g., cyclopropylamino, cyclohexylamino), optionally substituted $C_{6-14}$ aryl-amino (e.g., phenylamino, diphenylamino, naphthylamino), optionally substituted $C_{1-6}$ alkoxy-amino (e.g., methoxyamino, ethoxyamino, propoxyamino, isopropoxyamino), formylamino, optionally substituted $C_{1-6}$ alkyl-carbonylamino (e.g., acetylamino, propionylamino, pivaloylamino etc.), optionally substituted $C_{3-8}$ cycloalkyl-carbonylamino (e.g., cyclopropylcarbonylamino, cyclopentylcarbonylamino, cyclohexylcarbonylamino etc.), optionally substituted $C_{6-14}$ aryl-carbonylamino (e.g., benzoylamino, naphthoylamino etc.), optionally substituted $C_{1-6}$ alkoxy-carbonylamino (e.g., methoxycarbonylamino, ethoxycarbonylamino, propoxycarbonylamino, butoxycarbonylamino etc.), optionally substituted $C_{1-6}$ alkylsulfonylamino (e.g., methylsulfonylamino, ethylsulfonylamino etc.), optionally substituted $C_{6-14}$ arylsulfonylamino (e.g., phenylsulfonylamino, 2-naphthylsulfonylamino, 1-naphthylsulfonylamino etc.)],
(21) formyl,
(22) carboxy,
(23) optionally substituted $C_{1-6}$ alkyl-carbonyl (e.g., acetyl, propionyl, pivaloyl etc.),
(24) optionally substituted $C_{3-8}$ cycloalkyl-carbonyl (e.g., cyclopropylcarbonyl, cyclopentylcarbonyl, cyclohexylcarbonyl, 1-methyl-cyclohexyl-carbonyl etc.),
(25) optionally substituted $C_{6-14}$ aryl-carbonyl (e.g., benzoyl, 1-naphthoyl, 2-naphthoyl etc.),
(26) optionally substituted $C_{7-16}$ aralkyl-carbonyl (e.g., phenylacetyl, 3-phenylpropionyl etc.),
(27) optionally substituted 5- to 7-membered heterocyclylcarbonyl containing, besides carbon atom, one or two kinds of 1 to 4 hetero atoms selected from a nitrogen atom, a sulfur atom and an oxygen atom (e.g., nicotinoyl, isonicotinoyl, thenoyl, furoyl, morpholinocarbonyl, thiomorpholinocarbonyl, piperazin-1-ylcarbonyl, pyrrolidin-1-ylcarbonyl etc.),
(28) optionally esterified carboxyl,
(29) optionally substituted carbamoyl,
(30) optionally substituted $C_{1-6}$ alkylsulfonyl (e.g., methylsulfonyl, ethylsulfonyl etc.),
(31) optionally substituted $C_{1-6}$ alkylsulfinyl (e.g., methylsulfinyl, ethylsulfinyl etc.),
(32) optionally substituted $C_{6-14}$ arylsulfonyl (e.g., phenylsulfonyl, 1-naphthylsulfonyl, 2-naphthylsulfonyl etc.),
(33) optionally substituted $C_{6-14}$ arylsulfinyl (e.g., phenylsulfinyl, 1-naphthylsulfinyl, 2-naphthylsulfinyl etc.),
(34) optionally substituted $C_{1-6}$ alkyl-carbonyloxy (e.g., acetoxy, propionyloxy etc.),
(35) optionally substituted $C_{6-14}$ aryl-carbonyloxy (e.g., benzoyloxy, naphthylcarbonyloxy etc.),
(36) optionally substituted $C_{1-6}$ alkoxy-carbonyloxy (e.g., methoxycarbonyloxy, ethoxycarbonyloxy, propoxycarbonyloxy, butoxycarbonyloxy etc.),
(37) optionally substituted mono-$C_{1-6}$ alkylcarbamoyloxy (e.g., methylcarbamoyloxy, ethylcarbamoyloxy etc.),
(38) optionally substituted di-$C_{1-6}$ alkylcarbamoyloxy (e.g., dimethylcarbamoyloxy, diethylcarbamoyloxy etc.),
(39) optionally substituted mono- or di-$C_{6-14}$ arylcarbamoyloxy (e.g., phenylcarbamoyloxy, naphthylcarbamoyloxy etc.),
(40) an optionally substituted heterocyclic group,
(41) sulfo,
(42) sulfamoyl,
(43) sulfinamoyl,
(44) sulfenamoyl, and
(45) a group wherein two or more (e.g., 2-3) from these substituents are bonded (to be also referred to as substituent group A in the present specification. Unless otherwise specified, the definition of each group in the present specification is as defined for each substituent in substituent group A (those mentioned above and below) is used. While the number of the substituents is not particularly limited, 1 to 5, preferably 1 to 3, substituents may be present at substitutable positions. When the numbers of the substituents is two or more, the substituents may be the same or different.

As the "optionally esterified carboxyl" in substituent group A, for example, optionally substituted $C_{1-6}$ alkoxy-carbonyl (e.g., methoxycarbonyl, ethoxycarbonyl, propoxycarbonyl, tert-butoxycarbonyl etc.), optionally substituted $C_{6-14}$ aryloxy-carbonyl (e.g., phenoxycarbonyl etc.), optionally substituted $C_{7-16}$ aralkyloxy-carbonyl (e.g., benzyloxycarbonyl, phenethyloxycarbonyl etc.) and the like are used.

As "$C_{1-6}$ alkyl" of the "optionally substituted $C_{1-6}$ alkyl" in substituent group A, for example, methyl, ethyl, propyl, isopropyl, butyl, isobutyl, sec-butyl, tert-butyl, pentyl, isopentyl, neopentyl, hexyl and the like are used.

As "$C_{2-6}$ alkenyl" of the "optionally substituted $C_{2-6}$ alkenyl" in substituent group A, for example, vinyl, propenyl, isopropenyl, 2-buten-1-yl, 4-penten-1-yl, 5-hexen-1-yl and the like are used.

As "$C_{2-6}$ alkynyl" of the "optionally substituted $C_{2-6}$ alkynyl" in substituent group A, for example, 2-butyn-1-yl, 4-pentyn-1-yl, 5-hexin-1-yl and the like are used.

As "$C_{3-8}$ cycloalkyl" of the "optionally substituted $C_{3-8}$ cycloalkyl" in substituent group A, for example, cyclopropyl, cyclobutyl, cyclopentyl, cyclohexyl and the like are used.

As "$C_{6-14}$ aryl" of the "optionally substituted $C_{6-14}$ aryl" in substituent group A, for example, phenyl, 1-naphthyl, 2-naphthyl, 2-biphenylyl, 3-biphenylyl, 4-biphenylyl, 2-anthryl and the like are used.

As "$C_{7-16}$ aralkyl" of the "optionally substituted $C_{7-16}$ aralkyl" in substituent group A, for example, benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, 4-biphenylylmethyl) and the like are used.

As "$C_{1-6}$ alkoxy" of the "optionally substituted $C_{1-6}$ alkoxy" in substituent group A, for example, methoxy, ethoxy, propoxy, isopropoxy, butoxy, isobutoxy, sec-butoxy, pentyloxy, hexyloxy and the like are used.

As "$C_{6-14}$ aryloxy" of the "optionally substituted $C_{6-14}$ aryloxy" in substituent group A, for example, phenyloxy, 1-naphthyloxy, 2-naphthyloxy and the like are used.

As "$C_{7-16}$ aralkyloxy" of the "optionally substituted $C_{7-16}$ aralkyloxy" in substituent group A, for example, benzyloxy, phenethyloxy and the like are used.

As "$C_{1-6}$ alkylthio" of the "optionally substituted $C_{1-6}$ alkylthio" in substituent group A, for example, methylthio, ethylthio, propylthio, isopropylthio, butylthio, sec-butylthio, tert-butylthio and the like are used.

As "$C_{6-14}$ arylthio" of the "optionally substituted $C_{6-14}$ arylthio" in substituent group A, for example, phenylthio, 1-naphthylthio, 2-naphthylthio and the like are used.

As "$C_{7-16}$ aralkylthio" of the "optionally substituted $C_{7-16}$ aralkylthio" in substituent group A, for example, benzylthio, phenethylthio and the like are used.

As the substituent of the "$C_{1-6}$ alkoxy-carbonyl", "$C_{1-6}$ alkyl group", "$C_{2-6}$ alkenyl", "$C_{2-6}$ alkynyl", "$C_{1-6}$ alkoxy", "$C_{1-6}$ alkylthio", "$C_{1-6}$ alkyl-amino", "$C_{2-6}$ alkenyl-amino", "$C_{2-6}$ alkynyl-amino", "$C_{1-6}$ alkoxy-amino", "$C_{1-6}$ alkyl-carbonyl", "$C_{1-6}$ alkylsulfonyl", "$C_{1-6}$ alkylsulfinyl", "$C_{1-6}$ alkyl-carbonylamino", "$C_{1-6}$ alkoxy-carbonylamino", "$C_{1-6}$ alkylsulfonylamino", "$C_{1-6}$ alkyl-carbonyloxy", "$C_{1-6}$ alkoxy-carbonyloxy", "mono-$C_{1-6}$ alkylcarbamoyloxy" and "di-$C_{1-6}$ alkylcarbamoyloxy" in substituent group A, for example, 1 to 5 substituents selected from a halogen atom (e.g., a fluorine atom, a chlorine atom, a bromine atom, an iodine atom), carboxy, hydroxy, amino, mono- or di-$C_{1-6}$ alkylamino, mono- or di-$C_{6-14}$ arylamino, $C_{3-8}$ cycloalkyl, $C_{1-6}$ alkoxy, $C_{1-6}$ alkoxy-carbonyl, $C_{1-6}$ alkylthio, $C_{1-6}$ alkylsulfinyl, $C_{1-6}$ alkylsulfonyl, the above-mentioned optionally esterified carboxyl, carbamoyl, thiocarbamoyl, mono-$C_{1-6}$ alkylcarbamoyl (e.g., methylcarbamoyl, ethylcarbamoyl etc.), di-$C_{1-6}$ alkylcarbamoyl (e.g., dimethylcarbamoyl, diethylcarbamoyl, ethylmethylcarbamoyl etc.), mono- or di-$C_{6-14}$ arylcarbamoyl (e.g., phenylcarbamoyl, 1-naphthylcarbamoyl, 2-naphthylcarbamoyl etc.), mono- or di-5- to 7-membered heterocyclylcarbamoyl containing, besides carbon atom, one or two kinds of 1 to 4 hetero atoms selected from a nitrogen atom, a sulfur atom and an oxygen atom (e.g., 2-pyridylcarbamoyl, 3-pyridylcarbamoyl, 4-pyridylcarbamoyl, 2-thienylcarbamoyl, 3-thienylcarbamoyl etc.) and the like are used.

As the "$C_{6-14}$ aryloxy-carbonyl", "$C_{7-16}$ aralkyloxy-carbonyl", "$C_{3-8}$ cycloalkyl", "$C_{6-14}$ aryl", "$C_{7-16}$ aralkyl", "$C_{6-14}$ aryloxy", "$C_{7-16}$ aralkyloxy", "$C_{6-14}$ arylthio", "$C_{7-16}$ aralkylthio", "$C_{3-8}$ cycloalkyl-amino", "$C_{6-14}$ aryl-amino", "$C_{3-8}$ cycloalkyl-carbonyl", "$C_{6-14}$ aryl-carbonyl", "$C_{7-16}$ aralkyl-carbonyl", "5- to 7-membered heterocyclylcarbonyl containing, besides carbon atom, one or two kinds of 1 to 4 hetero atoms selected from a nitrogen atom, a sulfur atom and an oxygen atom", "$C_{6-14}$ arylsulfonyl", "$C_{6-14}$ arylsulfinyl", "$C_{3-8}$ cycloalkyl-carbonylamino", "$C_{6-14}$ aryl-carbonylamino", "$C_{6-14}$ arylsulfonylamino", "$C_{6-14}$ aryl-carbonyloxy", "mono- or di-$C_{6-14}$ arylcarbamoyloxy" in substituent group A, for example, 1 to 5 substituents selected from a halogen atom, hydroxy, carboxy, nitro, cyano, the above-mentioned optionally substituted $C_{1-6}$ alkyl, the above-mentioned optionally substituted $C_{2-6}$ alkenyl, the above-mentioned optionally substituted $C_{2-6}$ alkynyl, the above-mentioned optionally substituted $C_{3-8}$ cycloalkyl, the above-mentioned optionally substituted $C_{1-6}$ alkoxy, the above-mentioned optionally substituted $C_{1-6}$ alkylthio, the above-mentioned optionally substituted $C_{1-6}$ alkylsulfinyl, the above-mentioned optionally substituted $C_{1-6}$ alkylsulfonyl, the above-mentioned optionally esterified carboxyl, carbamoyl, thiocarbamoyl, mono-$C_{1-6}$ alkylcarbamoyl, di-$C_{1-6}$ alkylcarbamoyl, mono- or di-$C_{6-14}$ arylcarbamoyl, mono- or di-5- to 7-membered heterocyclylcarbamoyl containing, besides carbon atom, one or two kinds of 1 to 4 hetero atoms selected from a nitrogen atom, a sulfur atom and an oxygen atom, and the like are used.

As the "optionally substituted heterocyclic group" in substituent group A, for example, a 5- to 14-membered (monocyclic, bicyclic or tricyclic) heterocyclic group containing, besides carbon atom, one or two kinds of 1 to 4 hetero atoms selected from a nitrogen atom, a sulfur atom and an oxygen atom, preferably (i) a 5- to 14-membered (preferably 5- to 10-membered) aromatic heterocyclic group, (ii) a 5- to 10-membered nonaromatic heterocyclic group or (iii) a monovalent group obtained by removing any one hydrogen atom from a 7- to 10-membered bridged-hetero ring, and the like, which are optionally substituted by a halogen atom, hydroxy, carboxy, nitro, cyano, the above-mentioned optionally substituted $C_{1-6}$ alkyl, the above-mentioned optionally substituted $C_{2-6}$ alkenyl, the above-mentioned optionally substituted $C_{2-6}$ alkynyl, the above-mentioned optionally substituted $C_{3-8}$ cycloalkyl, the above-mentioned optionally substituted $C_{6-14}$ aryl, the above-mentioned optionally substituted $C_{1-6}$ alkoxy, the above-mentioned optionally substituted $C_{1-6}$ alkylthio, the above-mentioned optionally substituted $C_{6-14}$ arylthio, the above-mentioned optionally substituted $C_{7-16}$ aralkylthio, the above-mentioned optionally substituted $C_{1-6}$ alkylsulfinyl, the above-mentioned optionally substituted $C_{6-14}$ arylsulfinyl, the above-mentioned optionally substituted $C_{1-6}$ alkylsulfonyl, the above-mentioned optionally substituted $C_{6-14}$ arylsulfonyl, the above-mentioned optionally esterified carboxyl, carbamoyl, thiocarbamoyl, mono-$C_{1-6}$ alkylcarbamoyl, di-lower alkylcarbamoyl, mono- or di-$C_{6-14}$ arylcarbamoyl, mono- or di-5- to 7-membered heterocyclic carbamoyl containing, besides carbon atom, one or two kinds of 1 to 4 hetero atoms selected from a nitrogen atom, a sulfur atom and an oxygen atom etc., are used. Of these, a 5-membered aromatic heterocyclic group is preferably used. Specifically, for example, an aromatic heterocyclic group such as thienyl (e.g., 2-thienyl, 3-thienyl), furyl (e.g., 2-furyl, 3-furyl), pyridyl (e.g., 2-pyridyl, 3-pyridyl, 4-pyridyl), thiazolyl (e.g., 2-thiazolyl, 4-thiazolyl, 5-thiazolyl), oxazolyl (e.g., 2-oxazolyl, 4-oxazolyl), quinolyl (e.g., 2-quinolyl, 3-quinolyl, 4-quinolyl, 5-quinolyl, 8-quinolyl), isoquinolyl (e.g., 1-isoquinolyl, 3-isoquinolyl, 4-isoquinolyl, 5-isoquinolyl), pyrazinyl, pyrimidinyl (e.g., 2-pyrimidinyl, 4-pyrimidinyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), pyridazinyl (e.g., 3-pyridazinyl, 4-pyridazinyl), isothiazolyl (e.g., 3-isothiazolyl), isoxazolyl (e.g., 3-isoxazolyl), indolyl (e.g., 1-indolyl, 2-indolyl, 3-indolyl), 2-benzothiazolyl, benzo[b]thienyl, (e.g., 2-benzo[b]thienyl, 3-benzo[b]thienyl), benzo[b]furanyl (e.g., 2-benzo[b]furanyl, 3-benzo[b]furanyl) and the like, for example, a nonaromatic heterocyclic group such as pyrrolidinyl (e.g., 1-pyrrolidinyl, 2-pyrrolidinyl, 3-pyrrolidinyl), oxazolidinyl (e.g., 2-oxazolidinyl), imidazolinyl (e.g., 1-imidazolinyl, 2-imidazolinyl, 4-imidazolinyl), piperidinyl (e.g., 1-piperidinyl, 2-piperidinyl, 3-piperidinyl, 4-piperidinyl), piperazinyl (e.g., 1-piperazinyl, 2-piperazinyl), morpholino, thiomorpholino etc., and the like are used.

As the "optionally substituted carbamoyl" in substituent group A, carbamoyl optionally substituted by the above-mentioned optionally substituted $C_{1-6}$ alkyl, optionally substituted $C_{2-6}$ alkenyl, optionally substituted $C_{2-6}$ alkynyl, optionally substituted $C_{3-8}$ cycloalkyl, optionally substituted $C_{6-14}$ aryl, an optionally substituted heterocyclic group and the like are used. Specifically, for example, carbamoyl, thiocarbamoyl, mono-$C_{1-6}$ alkylcarbamoyl (e.g., methylcarbamoyl, ethylcarbamoyl etc.), di-$C_{1-6}$ alkylcarbamoyl (e.g., dimethylcarbamoyl, diethylcarbamoyl, ethylmethylcarbamoyl etc.), $C_{1-6}$ alkyl ($C_{1-6}$ alkoxy)carbamoyl (e.g., methyl(methoxy)carbamoyl, ethyl(methoxy)carbamoyl), mono- or di-$C_{6-14}$ arylcarbamoyl (e.g., phenylcarbamoyl, 1-naphthylcarbamoyl, 2-naphthylcarbamoyl etc.), mono- or di-5- to 7-membered heterocyclic carbamoyl containing, besides carbon atom, one or two kinds of 1 to 4 hetero atoms selected from a nitrogen atom, a sulfur atom and an oxygen atom (e.g., 2-pyridylcarbamoyl, 3-pyridylcarbamoyl, 4-pyridylcarbamoyl, 2-thienylcarbamoyl, 3-thienylcarbamoyl etc.), 5- to 7-membered cyclic carbamoyl (e.g., 1-pyrrolidinylcarbonyl, 1-piperidinylcarbonyl, hexamethyleneiminocarbonyl) and the like are used.

As the "optionally substituted amino" in substituent group A, amino optionally substituted by 1 or 2 groups selected from the above-mentioned optionally substituted $C_{1-6}$ alkyl, the above-mentioned optionally substituted $C_{2-6}$ alkenyl, the above-mentioned optionally substituted $C_{2-6}$ alkynyl, the above-mentioned optionally substituted $C_{3-8}$ cycloalkyl, the above-mentioned optionally substituted $C_{6-14}$ aryl, the above-mentioned optionally substituted $C_{1-6}$ alkoxy, formyl, the above-mentioned optionally substituted $C_{1-6}$ alkyl-carbonyl, the above-mentioned optionally substituted $C_{3-8}$ cycloalkyl-carbonyl, the above-mentioned optionally substituted $C_{6-14}$ aryl-carbonyl, the above-mentioned optionally substituted $C_{1-6}$ alkoxy-carbonyl, the above-mentioned optionally substituted $C_{1-6}$ alkylsulfonyl, optionally substituted $C_{6-14}$ arylsulfonyl) and the like are used.

More preferably, as the substituent of the "$C_{6-12}$ aromatic hydrocarbon group", "5- to 14-membered aromatic heterocyclic group consisting of 1 to 7 carbon atoms and a hetero atom selected from the group consisting of a nitrogen atom, an oxygen atom and a sulfur atom", "$C_{8-14}$ aromatic fused ring group", "5- to 14-membered aromatic fused heterocyclic group consisting of 3 to 11 carbon atoms and a hetero atom selected from the group consisting of a nitrogen atom, an oxygen atom and a sulfur atom", "nonaromatic cyclic hydrocarbon group having a carbon number of not more than 7" and "nonaromatic heterocyclic group having a carbon number of not more than 7", a halogen atom, hydroxy, $C_{1-6}$ alkoxy, optionally halogenated $C_{1-6}$ alkyl, optionally halogenated $C_{1-6}$ alkoxy, amino, nitro, cyano and the like are preferable.

As $R_1$,
(1) "$C_{1-4}$ alkyl having an optionally substituted $C_{6-12}$ aromatic hydrocarbon group" such as benzyl, 2-fluorobenzyl, 3-fluorobenzyl, 4-fluorobenzyl, 4-chlorobenzyl, 3,4-difluorobenzyl, 3,4-dichlorobenzyl, pentafluorobenzyl, 4-hydroxybenzyl, 4-methoxybenzyl, 4-trifluoromethylbenzyl, 4-aminobenzyl, 4-nitrobenzyl, 4-cyanobenzyl, phenethyl and the like,
(2) "$C_{1-4}$ alkyl having an optionally substituted 5- to 14-membered aromatic heterocyclic group consisting of 1 to 7 carbon atoms and a hetero atom selected from the group consisting of a nitrogen atom, an oxygen atom and a sulfur atom" such as 2-pyridylmethyl, 3-pyridylmethyl, 4-pyridylmethyl, 2-thienylmethyl, 3-thienylmethyl, 4-thiazolylmethyl and the like,
(3) "$C_{1-4}$ alkyl having an optionally substituted $C_{8-14}$ aromatic fused ring group" such as 1-naphthylmethyl, 2-naphthylmethyl, inden-2-ylmethyl and the like,
(4) "$C_{1-4}$ alkyl having an optionally substituted 5- to 14-membered aromatic fused heterocyclic group consisting of 3 to 11 carbon atoms, and a hetero atom selected from the group consisting of a nitrogen atom, an oxygen atom and a sulfur atom" such as 3-indolemethyl, 1-formylindol-3-ylmethyl, 3-benzo[b]thienylmethyl, 2-quinolylmethyl and the like,
(5) "$C_{1-4}$ alkyl having an optionally substituted nonaromatic cyclic hydrocarbon group having a carbon number of not more than 7" such as cyclohexylmethyl, cyclopentylmethyl, indan-2-ylmethyl and the like,
(6) "$C_{1-4}$ alkyl having an optionally substituted nonaromatic heterocyclic group having a carbon number of not more than 7" such as 4-piperidinylmethyl, tetrahydrofurfuryl, tetrahydrofuran-2-yl, tetrahydropyran-3-yl, indolin-3-yl etc., and the like are used. Of these, cyclohexylmethyl, benzyl, 4-fluorobenzyl, 4-hydroxybenzyl, pentafluorobenzyl, 2-pyridylmethyl, 4-pyridylmethyl, 1-naphthylmethyl, 2-naphthylmethyl and the like are preferable, and benzyl, 4-fluorobenzyl, cyclohexylmethyl and the like are particularly preferable.

As for $R_2$
$R_2$ is
(1) $C_{1-8}$ alkyl having an optionally substituted basic group, and optionally further having other substituent(s),
(2) aralkyl having an optionally substituted basic group, and optionally further having other substituent(s),
(3) $C_{1-4}$ alkyl having a nonaromatic cyclic hydrocarbon group having a carbon number of not more than 7 and an optionally substituted basic group and, and optionally further having other substituent(s), or
(4) $C_{1-4}$ alkyl having a nonaromatic heterocyclic group having a carbon number of not more than 7 and an optionally substituted basic group, and optionally further having other substituent(s).

As the "optionally substituted basic group", for example, (1) guanidino optionally having 1 or 2 $C_{1-6}$ alkyl, $C_{1-6}$ acyl (e.g., methyl, ethyl, propyl, isopropyl, butyl, acetyl, propionyl etc.) and the like, (2) amino optionally having 1 to 3 $C_{1-6}$ alkyl, $C_{1-6}$ acyl (e.g., methyl, ethyl, propyl, isopropyl, butyl, acetyl, propionyl etc.) and the like, (3) $C_{1-6}$ alkylcarbonyl-amino (e.g., acetamide) optionally substituted by guanidino optionally having 1 or 2 $C_{1-6}$ alkyl, $C_{1-6}$ acyl (e.g., methyl, ethyl, propyl, isopropyl, butyl, acetyl, propionyl etc.) and the like, (4) $C_{1-6}$ alkylcarbonyl-amino (e.g., acetamide) optionally substituted by amino optionally having 1 to 3 $C_{1-6}$ alkyl, $C_{1-6}$ acyl (e.g., methyl, ethyl, propyl, isopropyl, butyl, acetyl, propionyl etc.) and the like, and the like are used. Of these, guanidino, N-methylguanidino, N,N-dimethylguanidino, N,N'-dimethylguanidino, N-ethylguanidino, N-acetylguanidino, amino, N-methylamino, N,N-dimethylamino, aminoacetamide, guanidinoacetamide, amidino and the like are preferable.

As the "other substituent" other than the "optionally substituted basic group", a substituent selected from substituent group A is used.

As the "$C_{1-8}$ alkyl", for example, methyl, ethyl, propyl, isopropyl, butyl, isobutyl, sec-butyl, tert-butyl, pentyl, isopentyl, neopentyl, hexyl, heptyl, octyl and the like are used.

As the "aralkyl", for example, $C_{7-16}$ aralkyl such as benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, 4-biphenylylmethyl etc., and the like are used.

As the "nonaromatic cyclic hydrocarbon group having a carbon number of not more than 7", for example, $C_{3-7}$ cycloalkyl such as cyclopropyl, cyclobutyl, cyclopentyl, cyclohexyl etc., and the like are used.

As the "nonaromatic heterocyclic group having a carbon number of not more than 7", for example, a 5- to 10-membered nonaromatic heterocyclic group containing, besides 1 to 7 carbon atoms, one or two kinds of 1 to 4 hetero atoms selected from a nitrogen atom, a sulfur atom and an oxygen atom, and the like are used. Specifically, for example, pyrrolidinyl (e.g., 1-pyrrolidinyl, 2-pyrrolidinyl, 3-pyrrolidinyl), oxazolidinyl (e.g., 2-oxazolidinyl), imidazolinyl (e.g., 1-imidazolinyl, 2-imidazolinyl, 4-imidazolinyl), piperidinyl (e.g., 1-piperidinyl, 2-piperidinyl, 3-piperidinyl, 4-piperidinyl), piperazinyl (e.g., 1-piperazinyl, 2-piperazinyl), morpholino, thiomorpholino and the like are used.

As the "$C_{1-4}$ alkyl", for example, methyl, ethyl, propyl, isopropyl, butyl, isobutyl, sec-butyl, tert-butyl and the like are used.

As $R_2$, for example, (1) 3-guanidinopropyl, 3-(N-methylguanidino)propyl, 3-(N,N-dimethylguanidino)propyl, 3-(N,N'-dimethylguanidino)propyl, 3-(N-ethylguanidino)

propyl, 3-(N-propylguanidino)propyl, 3-(N-acetylguanidino)propyl, 4-guanidinobutyl, 4-(N-methylguanidino)butyl, 2-guanidinoethyl, 2-(N-methylguanidino)ethyl, 4-aminobutyl, 4-(N-methylamino)butyl, 4-(N,N-dimethylamino)butyl, 3-aminopropyl, 2-aminoethyl, aminomethyl, aminoacetamidomethyl, guanidinoacetamidomethyl, 2-(guanidinocarbonyl)ethyl, (2) 4-guanidinobenzyl, 4-aminobenzyl, (3) 4-guanidinocyclohexylmethyl, 4-aminocyclohexylmethyl, (4) 1-amidinopiperidin-4-ylmethyl and the like are used. Of these, 3-guanidinopropyl, 3-(N-methylguanidino)propyl, 3-(N,N-dimethylguanidino)propyl, 3-(N,N'-dimethylguanidino)propyl, 3-(N-ethylguanidino)propyl, 3-(N-propylguanidino)propyl, 3-(N-acetylguanidino)propyl, 4-guanidinobutyl, 4-(N-methylguanidino)butyl, 2-guanidinoethyl, 2-(N-methylguanidino)ethyl, 4-aminobutyl, 4-(N-methylamino)butyl, 4-(N,N-dimethylamino)butyl, 3-aminopropyl, 2-aminoethyl, aminoacetamidomethyl, guanidinoacetamidomethyl, 4-aminobenzyl and the like preferably, particularly, 3-guanidinopropyl, 3-(N-methylguanidino)propyl, 3-(N,N-dimethylguanidino)propyl, 3-(N,N'-dimethylguanidino)propyl, 3-(N-ethylguanidino)propyl, 3-(N-acetylguanidino)propyl, 4-guanidinobutyl, 4-(N-methylguanidino)butyl, 2-guanidinoethyl, 4-aminobutyl and the like are preferable.

As for $R_3$ $R_3$ is $C_{1-4}$ alkyl optionally substituted by substituent(s) selected from the group consisting of
(1) an optionally substituted $C_{6-12}$ aromatic hydrocarbon group,
(2) an optionally substituted 5- to 14-membered aromatic heterocyclic group consisting of 1 to 7 carbon atoms and a hetero atom selected from the group consisting of a nitrogen atom, an oxygen atom and a sulfur atom,
(3) an optionally substituted $C_{8-14}$ aromatic fused ring group,
(4) an optionally substituted 5- to 14-membered aromatic fused heterocyclic group consisting of 3 to 11 carbon atoms and a hetero atom selected from the group consisting of a nitrogen atom, an oxygen atom and a sulfur atom,
(5) an optionally substituted nonaromatic cyclic hydrocarbon group having a carbon number of not more than 7, and
(6) an optionally substituted nonaromatic heterocyclic group having a carbon number of not more than 7.

Of these, $C_{1-4}$ alkyl substituted by substituent(s) selected from the group consisting of
(1) an optionally substituted $C_{6-12}$ aromatic hydrocarbon group,
(2) an optionally substituted 5- to 14-membered aromatic heterocyclic group consisting of 1 to 7 carbon atoms and a hetero atom selected from the group consisting of a nitrogen atom, an oxygen atom and a sulfur atom,
(3) an optionally substituted $C_{8-14}$ aromatic fused ring group,
(4) an optionally substituted 5- to 14-membered aromatic fused heterocyclic group consisting of 3 to 11 carbon atoms and a hetero atom selected from the group consisting of a nitrogen atom, an oxygen atom and a sulfur atom,
(5) an optionally substituted nonaromatic cyclic hydrocarbon group having a carbon number of not more than 7, and
(6) an optionally substituted nonaromatic heterocyclic group having a carbon number of not more than 7, is preferable.

As the "$C_{1-4}$ alkyl", for example, methyl, ethyl, propyl, isopropyl, butyl, isobutyl, sec-butyl, tert-butyl and the like are used.

As the "$C_{6-12}$ aromatic hydrocarbon group", for example, a monocyclic $C_{6-12}$ aromatic hydrocarbon group such as phenyl, cyclooctatetraenyl etc., and the like are used.

As the "5- to 14-membered aromatic heterocyclic group consisting of 1 to 7 carbon atoms and a hetero atom selected from the group consisting of a nitrogen atom, an oxygen atom and a sulfur atom", for example, a 5- to 14-membered, preferably 5- to 10-membered, more preferably 5- or 6-membered, monocyclic aromatic heterocyclic group containing, besides 1 to 7 carbon atoms, one or two kinds of 1 to 4 hetero atoms selected from a nitrogen atom, a sulfur atom and an oxygen atom is used. Specifically, for example, thienyl (e.g., 2-thienyl, 3-thienyl), furyl (e.g., 2-furyl, 3-furyl), pyridyl (e.g., 2-pyridyl, 3-pyridyl, 4-pyridyl), thiazolyl (e.g., 2-thiazolyl, 4-thiazolyl, 5-thiazolyl), oxazolyl (e.g., 2-oxazolyl, 4-oxazolyl), pyrazinyl, pyrimidinyl (e.g., 2-pyrimidinyl, 4-pyrimidinyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), pyridazinyl (e.g., 3-pyridazinyl, 4-pyridazinyl), isothiazolyl (e.g., 3-isothiazolyl), isoxazolyl (e.g., 3-isoxazolyl) and the like are used.

As the "$C_{8-14}$ aromatic fused ring group", for example, naphthyl (e.g., 1-naphthyl, 2-naphthyl), anthryl (e.g., 2-anthryl, 9-anthryl) and the like are used.

As the "5- to 14-membered aromatic fused heterocyclic group consisting of 3 to 11 carbon atoms and a hetero atom selected from the group consisting of a nitrogen atom, an oxygen atom and a sulfur atom", for example, a 5- to 14-membered (preferably 5- to 10-membered) bicyclic or tricyclic aromatic heterocyclic group containing, besides 3 to 11 carbon atoms, one or two kinds of 1 to 4 hetero atoms selected from a nitrogen atom, a sulfur atom and an oxygen atom, or a monovalent group obtained by removing any one hydrogen atom from a 5- to 14-membered (preferably 5- to 10-membered) aromatic bridged-hetero ring containing, besides carbon atom, one or two kinds of 1 to 4 hetero atoms selected from a nitrogen atom, a sulfur atom and an oxygen atom is used. Specifically, for example, quinolyl (e.g., 2-quinolyl, 3-quinolyl, 4-quinolyl, 5-quinolyl, 8-quinolyl), isoquinolyl (e.g., 1-isoquinolyl, 3-isoquinolyl, 4-isoquinolyl, 5-isoquinolyl), indolyl (e.g., 1-indolyl, 2-indolyl, 3-indolyl), 2-benzothiazolyl, benzo[b]thienyl (e.g., 2-benzo[b]thienyl, 3-benzo[b]thienyl), benzo[b]furanyl (e.g., 2-benzo[b]furanyl, 3-benzo[b]furanyl) and the like are used.

As the "nonaromatic cyclic hydrocarbon group having a carbon number of not more than 7", for example, $C_{3-7}$ cycloalkyl such as cyclopropyl, cyclobutyl, cyclopentyl, cyclohexyl etc., and the like are used.

As the "nonaromatic heterocyclic group having a carbon number of not more than 7", a 5- to 10-membered nonaromatic heterocyclic group containing, besides 1 to 7 carbon atoms, one or two kinds of 1 to 4 hetero atoms selected from a nitrogen atom, a sulfur atom and an oxygen atom, such as pyrrolidinyl (e.g., 1-pyrrolidinyl, 2-pyrrolidinyl, 3-pyrrolidinyl), oxazolidinyl (e.g., 2-oxazolidinyl), imidazolinyl (e.g., 1-imidazolinyl, 2-imidazolinyl, 4-imidazolinyl), piperidinyl (e.g., 1-piperidinyl, 2-piperidinyl, 3-piperidinyl, 4-piperidinyl), piperazinyl (e.g., 1-piperazinyl, 2-piperazinyl), morpholino, thiomorpholino etc., and the like are used.

Examples of the substituents of the "$C_{6-12}$ aromatic hydrocarbon group", "5- to 14-membered aromatic heterocyclic group consisting of 1 to 7 carbon atoms and a hetero atom selected from the group consisting of a nitrogen atom, an oxygen atom and a sulfur atom", "$C_{8-14}$ aromatic fused ring group", "5- to 14-membered aromatic fused heterocyclic group consisting of 3 to 11 carbon atoms and a hetero atom selected from the group consisting of a nitrogen atom, an oxygen atom and a sulfur atom", "nonaromatic cyclic hydrocarbon group having a carbon number of not more than 7" and "nonaromatic heterocyclic group having a carbon number of not more than 7" include those similar to the aforementioned substituent group A. While the number of the substituents is not particularly limited, 1 to 5, preferably 1 to 3, substituents may be present at substitutable positions. When the number of the substituents is two or more, the substituents may be the same or different.

$R_3$ is preferably, for example,
(1) "$C_{1-4}$ alkyl having an optionally substituted $C_{6-12}$ aromatic hydrocarbon group" such as benzyl, 2-fluorobenzyl, 3-fluorobenzyl, 4-fluorobenzyl, 4-chlorobenzyl, 3,4-difluorobenzyl, 3,4-dichlorobenzyl, pentafluorobenzyl, 4-hydroxybenzyl, 4-methoxybenzyl, 3-trifluoromethylbenzyl, 4-aminobenzyl, 4-nitrobenzyl, 4-cyanobenzyl, phenethyl and the like,
(2) "$C_{1-4}$ alkyl having an optionally substituted 5- to 14-membered aromatic heterocyclic group consisting of 1 to 7 carbon atoms and a hetero atom selected from the group consisting of a nitrogen atom, an oxygen atom and a sulfur atom" such as 2-pyridylmethyl, 3-pyridylmethyl, 4-pyridylmethyl, 2-thienylmethyl, 3-thienylmethyl, 4-thiazolylmethyl and the like,
(3) "$C_{1-4}$ alkyl having an optionally substituted $C_{8-14}$ aromatic fused ring group" such as 1-naphthylmethyl, 2-naphthylmethyl, inden-2-ylmethyl and the like,
(4) "$C_{1-4}$ alkyl having an optionally substituted 5- to 14-membered aromatic fused heterocyclic group consisting of 3 to 11 carbon atoms and a hetero atom selected from the group consisting of a nitrogen atom, an oxygen atom and a sulfur atom" such as 1-indolemethyl, 2-indolemethyl, 3-indolemethyl, 1-formylindol-3-ylmethyl, 3-benzo[b]thienylmethyl, 2-quinolylmethyl and the like,
(5) "$C_{1-4}$ alkyl having an optionally substituted nonaromatic cyclic hydrocarbon group having a carbon number of not more than 7" such as cyclohexylmethyl, cyclopentylmethyl, indan-2-ylmethyl and the like,
(6) "$C_{1-4}$ alkyl having an optionally substituted nonaromatic heterocyclic group having a carbon number of not more than 7" such as 4-piperidinylmethyl, tetrahydrofurfuryl, tetrahydrofuran-2-yl, tetrahydropyran-3-yl, indolin-3-yl and the like, and the like are used. Of these, benzyl, 2-fluorobenzyl, 3-fluorobenzyl, 4-fluorobenzyl, 4-hydroxybenzyl, 4-aminobenzyl, 4-nitrobenzyl, 4-chlorobenzyl, 4-methoxybenzyl, 4-cyanobenzyl, 3-trifluoromethylbenzyl, 3,4-dichlorobenzyl, 3,4-difluorobenzyl, pentafluorobenzyl, 3-pyridylmethyl, 4-pyridylmethyl, 3-indolemethyl, 1-formylindol-3-ylmethyl, 3-benzo[b]thienylmethyl, 2-quinolylmethyl, 1-naphthylmethyl, 2-naphthylmethyl, cyclohexylmethyl, phenethyl and the like are preferable, and benzyl, 2-fluorobenzyl, 3-fluorobenzyl, 4-fluorobenzyl, 4-hydroxybenzyl, 4-aminobenzyl, 4-nitrobenzyl, 4-chlorobenzyl, 4-methoxybenzyl, 4-cyanobenzyl, 3-trifluoromethylbenzyl, 3,4-dichlorobenzyl, 3,4-difluorobenzyl, pentafluorobenzyl, 3-pyridylmethyl, 4-pyridylmethyl, 3-indolemethyl, 3-benzo[b]thienylmethyl, 1-naphthylmethyl, 2-naphthylmethyl, cyclohexylmethyl and the like are particularly preferable.

As for P
P is
(1) a hydrogen atom,
(2) any amino acid residues bound to each other contiguously or non-contiguously from the C-terminal side of the 1st-49th amino acid sequence of the amino acid sequence shown by SEQ ID NO: 67 (54 amino acid residues of human metastin),
(3) a group represented by the formula

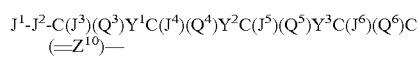

wherein each symbol is as defined above,
(4) a group represented by the formula

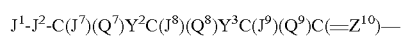

wherein each symbol is as defined above,
(5) a group represented by the formula

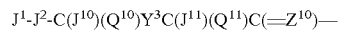

wherein each symbol is as defined above,
(6) a group represented by the formula $J^1$-$J_2$-C($J^{12}$)($Q^{12}$)C($=Z^{10}$)—
wherein each symbol is as defined above, or
(7) a group represented by the formula $J^1$- ($J^1$ is as defined above).

As the "any amino acid residues bound to each other contiguously or non-contiguously from the C-terminal side of the 1st-49th amino acid sequence of the amino acid sequence shown by SEQ ID NO: 67", specifically, (1) Ser-, (2) Asn Ser-, (3) Trp Asn Ser-, (SEQ ID NO: 1)
(4) Asn Trp Asn Ser-, (SEQ ID NO: 2)
(5) Tyr Asn Trp Asn Ser-, (SEQ ID NO: 3)
(6) Asn Tyr Asn Trp Asn Ser-, (SEQ ID NO: 4)
(7) Pro Asn Tyr Asn Trp Asn Ser-, (SEQ ID NO: 5)
(8) Leu Pro Asn Tyr Asn Trp Asn Ser-, (SEQ ID NO: 6)
(9) Asp Leu Pro Asn Tyr Asn Trp Asn Ser-, (SEQ ID NO: 7)
(10) Lys Asp Leu Pro Asn Tyr Asn Trp Asn Ser-, (SEQ ID NO: 8)
(11) Glu Lys Asp Leu Pro Asn Tyr Asn Trp Asn Ser-, (SEQ ID NO: 9)
(12) Arg Glu Lys Asp Leu Pro Asn Tyr Asn Trp Asn Ser-, (SEQ ID NO: 10)
(13) Gln Arg Glu Lys Asp Leu Pro Asn Tyr Asn Trp Asn Ser-, (SEQ ID NO: 11)
(14) Val Gln Arg Glu Lys Asp Leu Pro Asn Tyr Asn Trp Asn Ser-, (SEQ ID NO: 12)
(15) Leu Val Gln Arg Glu Lys Asp Leu Pro Asn Tyr Asn Trp Asn Ser-, (SEQ ID NO: 13)
(16) Val Leu Val Gln Arg Glu Lys Asp Leu Pro Asn Tyr Asn Trp Asn Ser-, (SEQ ID NO: 14)
(17) Ala Val Leu Val Gln Arg Glu Lys Asp Leu Pro Asn Tyr Asn Trp Asn Ser-, (SEQ ID NO: 15)
(18) Gly Ala Val Leu Val Gln Arg Glu Lys Asp Leu Pro Asn Tyr Asn Trp Asn Ser-, (SEQ ID NO: 16)
(19) Gln Gly Ala Val Leu Val Gln Arg Glu Lys Asp Leu Pro Asn Tyr Asn Trp Asn Ser-, (SEQ ID NO: 17)
(20) Pro Gln Gly Ala Val Leu Val Gln Arg Glu Lys Asp Leu Pro Asn Tyr Asn Trp Asn Ser-, (SEQ ID NO: 18)
(21) Ala Pro Gln Gly Ala Val Leu Val Gln Arg Glu Lys Asp Leu Pro Asn Tyr Asn Trp Asn Ser-, (SEQ ID NO: 19)
(22) Pro Ala Pro Gln Gly Ala Val Leu Val Gln Arg Glu Lys Asp Leu Pro Asn Tyr Asn Trp Asn Ser-, (SEQ ID NO: 20)
(23) Ile Pro Ala Pro Gln Gly Ala Val Leu Val Gln Arg Glu Lys Asp Leu Pro Asn Tyr Asn Trp Asn Ser-, (SEQ ID NO: 21)
(24) Gln Ile Pro Ala Pro Gln Gly Ala Val Leu Val Gln Arg Glu Lys Asp Leu Pro Asn Tyr Asn Trp Asn Ser-, (SEQ ID NO: 22)
(25) Arg Gln Ile Pro Ala Pro Gln Gly Ala Val Leu Val Gln Arg Glu Lys Asp Leu Pro Asn Tyr Asn Trp Asn Ser-, (SEQ ID NO: 23)
(26) Ser Arg Gln Ile Pro Ala Pro Gln Gly Ala Val Leu Val Gln Arg Glu Lys Asp Leu Pro Asn Tyr Asn Trp Asn Ser-, (SEQ ID NO: 24)
(27) His Ser Arg Gln Ile Pro Ala Pro Gln Gly Ala Val Leu Val Gln Arg Glu Lys Asp Leu Pro Asn Tyr Asn Trp Asn Ser-, (SEQ ID NO: 25)
(28) Pro His Ser Arg Gln Ile Pro Ala Pro Gln Gly Ala Val Leu Val Gln Arg Glu Lys Asp Leu Pro Asn Tyr Asn Trp Asn Ser-, (SEQ ID NO: 26)
(29) Ala Pro His Ser Arg Gln Ile Pro Ala Pro Gln Gly Ala Val Leu Val Gln Arg Glu Lys Asp Leu Pro Asn Tyr Asn Trp Asn Ser-, (SEQ ID NO: 27)
(30) Ser Ala Pro His Ser Arg Gln Ile Pro Ala Pro Gln Gly Ala Val Leu Val Gln Arg Glu Lys Asp Leu Pro Asn Tyr Asn Trp Asn Ser-, (SEQ ID NO: 28)
(31) Leu Ser Ala Pro His Ser Arg Gln Ile Pro Ala Pro Gln Gly Ala Val Leu Val Gln Arg Glu Lys Asp Leu Pro Asn Tyr Asn Trp Asn Ser-, (SEQ ID NO: 29)
(32) Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn Ser-, (SEQ ID NO: 30)
(33) Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn Ser-, (SEQ ID NO: 31)
(34) Gln Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn Ser-, (SEQ ID NO: 32)
(35) Gln Gln Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn Ser-, (SEQ ID NO: 33)
(36) Arg Gln Gln Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn Ser-, (SEQ ID NO: 34)
(37) Ser Arg Gln Gln Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn Ser-, (SEQ ID NO: 35)
(38) Gly Ser Arg Gln Gln Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn Ser-, (SEQ ID NO: 36)
(39) Ser Gly Ser Arg Gln Gln Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn Ser-, (SEQ ID NO: 37)
(40) Ser Ser Gly Ser Arg Gln Gln Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn Ser-, (SEQ ID NO: 38)
(41) Glu Ser Ser Gly Ser Arg Gln Gln Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn Ser-, (SEQ ID NO: 39)
(42) Pro Glu Ser Ser Gly Ser Arg Gln Gln Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn Ser-, (SEQ ID NO: 40)
(43) Pro Pro Glu Ser Ser Gly Ser Arg Gln Gln Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn Ser-, (SEQ ID NO: 41)
(44) Pro Pro Pro Glu Ser Ser Gly Ser Arg Gln Gln Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn Ser-, (SEQ ID NO: 42)
(45) Ser Pro Pro Pro Glu Ser Ser Gly Ser Arg Gln Gln Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn Ser-, (SEQ ID NO: 43)
(46) Leu Ser Pro Pro Pro Glu Ser Ser Gly Ser Arg Gln Gln Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn Ser-, (SEQ ID NO: 44)
(47) Ser Leu Ser Pro Pro Pro Glu Ser Ser Gly Ser Arg Gln Gln Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn Ser-, (SEQ ID NO: 45)
(48) Thr Ser Leu Ser Pro Pro Pro Glu Ser Ser Gly Ser Arg Gln Gln Pro Gly Leu Ser Ala Pro His Ser Arg Gln Ile Pro Ala Pro Gln Gly Ala Val Leu Val Gln Arg Glu Lys Asp Leu Pro Asn Tyr Asn Trp Asn Ser-, (SEQ ID NO: 46)
(49) Gly Thr Ser Leu Ser Pro Pro Pro Glu Ser Ser Gly Ser Arg Gln Gln Pro Gly Leu Ser Ala Pro His Ser Arg Gln Ile Pro Ala Pro Gln Gly Ala Val Leu -continued Val Gln Arg Glu Lys Asp Leu Pro Asn Tyr Asn Trp
Asn Serand the like are used.

$J^1$ is (a) a hydrogen atom or (b) (i) $C_{1-15}$ acyl, (ii) $C_{1-15}$ alkyl, (iii) $C_{6-14}$ aryl, (iv) carbamoyl, (v) carboxyl, (vi) sulfino, (vii) amidino or (viii) glyoxyloyl, each of which is optionally substituted by substituent(s) containing a ring group optionally having substituent(s).

As the "ring group", for example, "optionally substituted aromatic hydrocarbon group", "optionally substituted aromatic heterocyclic group", "optionally substituted aromatic fused ring group", "optionally substituted aromatic fused heterocyclic group", "optionally substituted nonaromatic cyclic hydrocarbon group", "optionally substituted nonaromatic heterocyclic group" and the like are used, and as the "aromatic hydrocarbon group", "aromatic heterocyclic group", "aromatic fused ring group", and "aromatic fused heterocyclic group", those similar to the aforementioned ones are used.

As the "nonaromatic cyclic hydrocarbon group", $C_{3-8}$ cycloalkyl such as cyclopropyl, cyclobutyl, cyclopentyl, cyclohexyl etc., and the like are used.

As the "nonaromatic heterocyclic group", a 5- to 10-membered nonaromatic heterocyclic group containing, besides 1 to 7 carbon atoms, one or two kinds of 1 to 4 hetero atoms selected from a nitrogen atom, a sulfur atom and an oxygen atom, such as pyrrolidinyl (e.g., 1-pyrrolidinyl, 2-pyrrolidinyl, 3-pyrrolidinyl), oxazolidinyl (e.g., 2-oxazolidinyl), imidazolinyl (e.g., 1-imidazolinyl, 2-imidazolinyl, 4-imidazolinyl), piperidinyl (e.g., 1-piperidinyl, 2-piperidinyl, 3-piperidinyl, 4-piperidinyl), piperazinyl (e.g., 1-piperazinyl, 2-piperazinyl), morpholino, thiomorpholino etc., and the like are used.

As the substituent that the "ring group" may have, those similar to the substituents in the aforementioned substituent group A are used.

As the "$C_{1-15}$ acyl", for example, formyl, $C_{1-14}$ alkyl-carbonyl (e.g., $C_{1-6}$ alkyl-carbonyl such as acetyl, propionyl, pivaloyl etc.) and the like are used.

As the "$C_{1-15}$ alkyl", for example, methyl, ethyl, propyl, isopropyl, butyl, isobutyl, sec-butyl, tert-butyl, pentyl, isopentyl, neopentyl, hexyl, heptyl, octyl, nonanyl, decanyl and the like are used.

As the "$C_{6-14}$ aryl", for example, phenyl, 1-naphthyl, 2-naphthyl, biphenyl and the like are used.

As (1) $C_{1-15}$ acyl optionally substituted by substituent(s) containing a ring group, (i) formyl, (ii) $C_{1-14}$ alkyl-carbonyl (e.g., $C_{1-6}$ alkyl-carbonyl such as acetyl, propionyl, pivaloyl etc.), (iii) $C_{3-8}$ cycloalkyl-carbonyl (e.g., cyclopropylcarbonyl, cyclopentylcarbonyl, cyclohexylcarbonyl, 1-methylcyclohexylcarbonyl etc.), (iv) $C_{3-8}$ cycloalkyl-$C_{1-6}$ alkyl-carbonyl (e.g., cyclopropylacetyl, cyclopentylacetyl, cyclohexylacetyl etc.) (v) $C_{6-14}$ aryl-carbonyl (e.g., benzoyl, 1-naphthoyl, 2-naphthoyl etc.), $C_{6-14}$ aralkyl-carbonyl (e.g., phenylacetyl, 3-phenylpropionyl etc.), (vi) 5- to 7-membered monocyclic heterocyclylcarbonyl containing, besides carbon atom, one or two kinds of 1 to 4 hetero atoms selected from a nitrogen atom, a sulfur atom and an oxygen atom (e.g., nicotinoyl, isonicotinoyl, thenoyl, furoyl, morpholinocarbonyl, thiomorpholinocarbonyl, piperazin-1-ylcarbonyl, pyrrolidin-1-ylcarbonyl etc.), (vii) 5- to 7-membered monocyclic heterocyclyl-$C_{1-6}$ alkylcarbonyl containing, besides carbon atom, one or two kinds of 1 to 4 hetero atoms selected from a nitrogen atom, a sulfur atom and an oxygen atom (e.g., 3-pyridylacetyl, 4-pyridylacetyl, 2-thienylacetyl, 2-furylacetyl, morpholinoacetyl, thiomorpholinoacetyl, piperidine-2-acetyl, pyrrolidin-2-ylacetyl etc.), (viii) 5- to 14-membered (preferably 5- to 10-membered) bicyclic or tricyclic aromatic heterocyclylcarbonyl containing, besides 3 to 11 carbon atoms, one or two kinds of 1 to 4 hetero atoms selected from a nitrogen atom, a sulfur atom and an oxygen atom (e.g., 2-indolecarbonyl, 3-indolecarbonyl, 2-quinolylcarbonyl, 1-isoquinolylcarbonyl, 2-benzo[b]thienylcarbonyl, 2-benzo[b]furanylcarbonyl etc.), (ix) 5- to 14-membered (preferably 5- to 10-membered) bicyclic or tricyclic aromatic heterocyclyl-$C_{1-6}$ alkylcarbonyl containing, besides 3 to 11 carbon atoms, one or two kinds of 1 to 4 hetero atoms selected from a nitrogen atom, a sulfur atom and an oxygen atom (e.g., 2-indoleacetyl, 3-indoleacetyl, 2-quinolylacetyl, 1-isoquinolylacetyl, 2-benzo[b]thienylacetyl, 2-benzo[b]furanylacetyl etc.) and the like are used. Of these, acetyl, 2-indolecarbonyl, 3-indolecarbonyl, 3-indoleacetyl, 3-indolepropionyl, 2-indolinecarbonyl, 3-phenylpropionyl, diphenylacetyl, 2-pyridinecarbonyl, 3-pyridinecarbonyl, 4-pyridinecarbonyl, 1-pyridinioacetyl, 2-pyridineacetyl, 3-pyridineacetyl, 4-pyridineacetyl, 3-(1-pyridinio)propionyl, 3-(pyridin-2-yl)propionyl, 3-(pyridin-3-yl)propionyl, 3-(pyridin-4-yl)propionyl, 4-imidazoleacetyl, cyclohexanecarbonyl, 1-piperidineacetyl, 1-methyl-1-piperidinioacetyl, 4-piperidinecarbonyl, 2-pyrimidinecarbonyl, 4-pyrimidinecarbonyl, 5-pyrimidinecarbonyl, 2-pyrimidineacetyl, 4-pyrimidineacetyl, 5-pyrimidineacetyl, 3-(pyrimidin-2-yl)propionyl, 3-(pyrimidin-4-yl)propionyl, 3-(pyrimidin-5-yl)propionyl, butanoyl, hexanoyl, octanoyl, D-glucuronyl, amino-(4-hydroxyphenyl)acetyl) and the like are preferably used.

As (2) $C_{1-15}$ alkyl optionally substituted by substituent(s) containing a ring group, for example, (i) mono- or di-$C_{1-15}$ alkyl (e.g., methyl, ethyl, propyl, isopropyl, butyl, isobutyl, sec-butyl, tert-butyl, pentyl, isopentyl, neopentyl, hexyl, heptyl, octyl, nonanyl, decanyl), (ii) mono- or di-$C_{3-8}$ cycloalkyl (e.g., cyclopropyl, cyclopentyl etc.), (iii) mono- or di-$C_{3-8}$ cycloalkyl-$C_{1-7}$ alkyl (e.g., cyclopropylmethyl, cyclopentylmethyl, cyclohexylethyl etc.), (iv) mono- or di-$C_{7-15}$ aralkyl (e.g., benzyl, phenethyl etc.), (v) mono- or di-5- to 7-membered monocyclic heterocyclyl-$C_{1-6}$ alkyl containing, besides carbon atom, one or two kinds of 1 to 4 hetero atoms selected from a nitrogen atom, a sulfur atom and an oxygen atom (e.g., 3-pyridylmethyl, 4-pyridylmethyl, 2-thienylmethyl, furfuryl etc.), (vi) mono- or di-5- to 14-membered (preferably 5- to 10-membered) bicyclic or tricyclic aromatic heterocyclyl-$C_{1-6}$ alkyl containing, besides 3 to 11 carbon atoms, one or two kinds of 1 to 4 hetero atoms selected from a nitrogen atom, a sulfur atom and an oxygen atom (e.g., 2-indolemethyl, 3-indolemethyl, 3-(indol-3-yl)propyl, 2-quinolylmethyl, 1-isoquinolylmethyl, 2-benzo[b]thienylmethyl, 2-benzo[b]furanylmethyl etc.) and the like are used. Of these, methyl, ethyl, benzyl, 3-(indol-3-yl)propyl and the like are preferably used.

As (3) $C_{6-14}$ aryl optionally substituted by substituent(s) containing a ring group, for example, $C_{6-14}$ aryl (e.g., phenyl, naphthyl, biphenyl) optionally substituted by (i) a $C_{6-14}$ carbon ring group (e.g., cycloalkyl, phenyl, 1-naphthyl, 2-naphthyl etc.), (ii) a 5- to 7-membered monocyclic heterocyclic group containing, besides carbon atom, one or two kinds of 1 to 4 hetero atoms selected from a nitrogen atom, a sulfur atom and an oxygen atom (e.g., 3-pyridyl, 2-thienyl etc.), (iii) a 5- to 14-membered (preferably 5- to 10-membered) bicyclic or tricyclic aromatic heterocyclic group containing, besides 3 to 11 carbon atoms, one or two kinds of 1 to 4 hetero atoms selected from a nitrogen atom, a sulfur atom and an oxygen atom (e.g., 2-indolyl, 3-indolyl, 2-quinolyl, 1-isoquinolyl, 2-benzo[b]thienyl, 2-benzo[b]furanyl etc.) etc.), and the like are used.

As (4) carbamoyl optionally substituted by substituent(s) containing a ring group, (i) carbamoyl, (ii) mono- or di-$C_{1-15}$ alkylcarbamoyl (e.g., methylcarbamoyl, ethylcarbamoyl), (iii) mono- or di-$C_{3-8}$ cycloalkyl-carbamoyl (e.g., cyclopropylcarbamoyl, cyclopentylcarbamoyl, cyclohexylcarbamoyl etc.), (iv) mono- or di-$C_{3-8}$ cycloalkyl-$C_{1-6}$ alkyl-carbamoyl (e.g., cyclopropylmethylcarbamoyl, cyclopentylmethylcarbamoyl, 2-cyclohexylethylcarbamoyl etc.), (v) mono- or di-$C_{6-14}$ aryl-carbamoyl (e.g., phenylcarbamoyl etc.), mono- or di-$C_{6-14}$ aralkyl-carbamoyl (e.g., benzylcarbamoyl, phenethylcarbamoyl etc.), (vi) mono- or di-5- to 7-membered monocyclic heterocyclic carbamoyl containing, besides carbon atom, one or two kinds of 1 to 4 hetero atoms selected from a nitrogen atom, a sulfur atom and an oxygen atom (e.g., 3-pyridinecarbamoyl, 2-thiophenecarbamoyl, piperidin-3-ylcarbamoyl etc.), (vii) mono- or di-5- to 7-membered monocyclic heterocyclyl-$C_{1-6}$ alkylcarbamoyl containing, besides carbon atom, one or two kinds of 1 to 4 hetero atoms selected from a nitrogen atom, a sulfur atom and an oxygen atom (e.g., 3-pyridylmethylcarbamoyl, 2-(pyridin-2-yl)ethylcarbamoyl, 2-(piperidin-1-yl)ethylcarbamoyl etc.), (viii) mono- or di-5- to 14-membered (preferably 5- to 10-membered) bicyclic or tricyclic aromatic heterocyclic carbamoyl containing, besides 3 to 11 carbon atoms, one or two kinds of 1 to 4 hetero atoms selected from a nitrogen atom, a sulfur atom and an oxygen atom (e.g., 4-indolecarbamoyl, 5-indolecarbamoyl, 3-quinolylcarbamoyl, 5-quinolylcarbamoyl etc.), (ix) mono- or di-5- to 14-membered (preferably 5- to 10-membered) bicyclic or tricyclic aromatic heterocyclyl-$C_{1-6}$ alkylcarbonyl containing, besides 3 to 11 carbon atoms, one or two kinds of 1 to 4 hetero atoms selected from a nitrogen atom, a sulfur atom and an oxygen atom (e.g., benzimidazol-2-ylmethylcarbamoyl, 2-(indol-3-yl)ethylcarbamoyl etc.), (x) 5- to 7-membered cyclic carbamoyl (e.g., 1-pyrrolidinylcarbonyl, 1-piperidinylcarbonyl, hexamethyleneiminocarbonyl etc.), (xi) $C_{1-15}$ acylcarbamoyl (wherein $C_{1-15}$ acyl is as defined for "$C_{1-15}$ acyl" of the "$C_{1-15}$ acyl optionally substituted by substituent(s) containing a ring group"), (xii) $C_{1-15}$ alkylaminocarbamoyl (wherein $C_{1-15}$ alkyl is as defined for "$C_{1-15}$ alkyl" of the "$C_{1-15}$ alkyl optionally substituted by substituent(s) containing a ring group"), (xiii) $C_{6-14}$ arylaminocarbamoyl (wherein $C_{6-14}$ aryl is as defined for "$C_{6-14}$ aryl" of the "$C_{6-14}$ aryl optionally substituted by substituent(s) containing a ring group") and the like are used. Of these, 2-(indol-3-yl)ethylcarbamoyl and the like are preferably used.

As (5) carboxyl optionally substituted by substituent(s) containing a ring group, (i) $C_{1-15}$ alkyloxycarbonyl (wherein $C_{1-15}$ alkyl is as defined for "$C_{1-15}$ alkyl" of the "$C_{1-15}$ alkyl optionally substituted by substituent(s) containing a ring group" (e.g., tert-butyloxycarbonyl, benzyloxycarbonyl, 9-fluorenylmethoxycarbonyl)), (ii) $C_{6-14}$ aryloxycarbonyl (wherein $C_{6-14}$ aryl is as defined for "$C_{6-14}$ aryl" of the "$C_{6-14}$ aryl optionally substituted by substituent(s) containing a ring group" (e.g., phenoxycarbonyl)), and the like are used.

As (6) sulfino optionally substituted by substituent(s) containing a ring group, (i) $C_{1-15}$ alkylsulfonyl (wherein $C_{1-15}$ alkyl is as defined for "$C_{1-15}$ alkyl" of the "$C_{1-15}$ alkyl optionally substituted by substituent(s) containing a ring group" (e.g., benzylsulfonyl)), (ii) $C_{6-14}$ arylsulfonyl (wherein $C_{6-14}$ aryl is as defined for "$C_{6-14}$ aryl" of the "$C_{6-14}$ aryl optionally substituted by substituent(s) containing a ring group" (e.g., tosyl)) and the like are used.

As (7) amidino optionally substituted by substituent group (s) containing a ring, (i) amidino, (ii) $C_{1-15}$ alkylamidino (wherein $C_{1-15}$ alkyl is as defined for "$C_{1-15}$ alkyl" of the "$C_{1-15}$ alkyl optionally substituted by substituent(s) containing a ring group" (e.g., N-methylamidino)), (iii) $C_{1-15}$ acylamidino (wherein $C_{1-15}$ acyl is as defined for "$C_{1-15}$ acyl" of the "$C_{1-15}$ acyl optionally substituted by substituent(s) containing a ring group" (e.g., N-acetylamidino)) and the like are used.

As (8) glyoxyloyl optionally substituted by substituent(s) containing a ring group, (i) $C_{1-15}$ alkyloxalyl (wherein $C_{1-15}$ alkyl is as defined for "$C_{1-15}$ alkyl" of the "$C_{1-15}$ alkyl optionally substituted by substituent(s) containing a ring group" (e.g., ethyloxalyl), (ii) $C_{6-14}$ aryloxalyl (wherein $C_{6-14}$ aryl is as defined for "$C_{6-14}$ aryl" of the "$C_{6-14}$ aryl optionally substituted by substituent(s) containing a ring group" (e.g., phenyloxalyl) and the like are used.

Among those mentioned above, as $J^1$, a hydrogen atom, acetyl, 4-fluorobenzoyl, 3-indolecarbonyl, 3-(indol-3-yl)propionyl, 3-phenylpropionyl, diphenylacetyl, 3-(pyridin-3-yl)propionyl, 4-imidazoleacetyl, cyclohexanecarbonyl, 1-piperidineacetyl, 1-methyl-1-piperidinioacetyl, 4-piperidinecarbonyl, hexanoyl, amino-(4-hydroxyphenyl)acetyl, D-glucuronyl, 2-(indol-3-yl)ethylcarbamoyl, tert-butyloxycarbonyl, 9-fluorenylmethoxycarbonyl, amidino, fluorobenzoyl, 4-(aminomethyl)benzoyl and the like are preferably used. Of these, a hydrogen atom, acetyl, 4-fluorobenzoyl, 3-indolecarbonyl, 3-(indol-3-yl)propionyl, 3-phenylpropionyl, 3-(pyridin-3-yl)propionyl, 4-imidazoleacetyl, cyclohexanecarbonyl, hexanoyl, amino-(4-hydroxyphenyl)acetyl, 2-(indol-3-yl)ethylcarbamoyl, 9-fluorenylmethoxycarbonyl, amidino and the like are preferable.

$J^2$ is (1) NH optionally substituted by $C_{1-6}$ alkyl, (2) $CH_2$ optionally substituted by $C_{1-6}$ alkyl, (3) O or (4) S.

As the "$C_{1-6}$ alkyl", methyl, ethyl, propyl, isopropyl, butyl, isobutyl, sec-butyl, tert-butyl, pentyl, isopentyl, neopentyl, hexyl and the like are used.

As $J^2$, NH is preferable.

$J^3$-$J^{12}$ are each a hydrogen atom or $C_{1-3}$ alkyl.

As the "$C_{1-3}$ alkyl", methyl, ethyl, propyl and isopropyl are used.

As $J^3$, a hydrogen atom is preferable.
As $J^4$, a hydrogen atom is preferable.
As $J^5$, a hydrogen atom is preferable.
As $J^6$, a hydrogen atom is preferable.
As $J^7$, a hydrogen atom is preferable.
As $J^8$, a hydrogen atom is preferable.
As $J^9$, a hydrogen atom is preferable.
As $J^{10}$, a hydrogen atom is preferable.
As $J^{11}$, a hydrogen atom is preferable.
As $J^{12}$, a hydrogen atom is preferable.

$Q^3$-$Q^{12}$ are each $C_{1-4}$ alkyl optionally having substituent(s) selected from the group consisting of
(1) an optionally substituted $C_{6-12}$ aromatic hydrocarbon group,
(2) an optionally substituted 5- to 14-membered aromatic heterocyclic group consisting of 1 to 7 carbon atoms and a hetero atom selected from the group consisting of a nitrogen atom, an oxygen atom and a sulfur atom,
(3) an optionally substituted $C_{8-14}$ aromatic fused ring group,
(4) an optionally substituted 5- to 14-membered aromatic fused heterocyclic group consisting of 3 to 11 carbon atoms and a hetero atom selected from the group consisting of a nitrogen atom, an oxygen atom and a sulfur atom,
(5) an optionally substituted nonaromatic cyclic hydrocarbon group having a carbon number of not more than 7,
(6) an optionally substituted nonaromatic heterocyclic group having a carbon number of not more than 7, (7) optionally substituted amino,
(8) optionally substituted guanidino,
(9) optionally substituted hydroxy,
(10) optionally substituted carboxyl,
(11) optionally substituted carbamoyl, and
(12) optionally substituted sulfhydryl.

Particularly, as $Q^3$-$Q^6$, $C_{1-4}$ alkyl having substituent(s) selected from the group consisting of
(1) an optionally substituted $C_{6-12}$ aromatic hydrocarbon group,
(2) an optionally substituted 5- to 14-membered aromatic heterocyclic group consisting of 1 to 7 carbon atoms and a hetero atom selected from the group consisting of a nitrogen atom, an oxygen atom and a sulfur atom,
(3) an optionally substituted $C_{8-14}$ aromatic fused ring group,
(4) an optionally substituted 5- to 14-membered aromatic fused heterocyclic group consisting of 3 to 11 carbon atoms, and a hetero atom selected from the group consisting of a nitrogen atom, an oxygen atom and a sulfur atom,
(5) an optionally substituted nonaromatic cyclic hydrocarbon group having a carbon number of not more than 7,
(6) an optionally substituted nonaromatic heterocyclic group having a carbon number of not more than 7,
(7) optionally substituted amino,
(8) optionally substituted guanidino,
(9) optionally substituted hydroxy,
(10) optionally substituted carboxyl,
(11) optionally substituted carbamoyl, and
(12) optionally substituted sulfhydryl
or a hydrogen atom is preferable.

As the "optionally substituted $C_{6-12}$ aromatic hydrocarbon group", "optionally substituted 5- to 14-membered aromatic heterocyclic group consisting of 1 to 7 carbon atoms and a hetero atom selected from the group consisting of a nitrogen atom, an oxygen atom and a sulfur atom", "optionally substituted $C_{8-14}$ aromatic fused ring group", "optionally substituted 5- to 14-membered aromatic fused heterocyclic group consisting of 3 to 11 carbon atoms and a hetero atom selected from the group consisting of a nitrogen atom, an oxygen atom and a sulfur atom", "optionally substituted nonaromatic cyclic hydrocarbon group having a carbon number of not more than 7" and "optionally substituted nonaromatic heterocyclic group having a carbon number of not more than 7", those similar to the aforementioned groups are used.

(1) As $C_{1-4}$ alkyl having an optionally substituted $C_{6-12}$ aromatic hydrocarbon group, for example, benzyl, 4-hydroxybenzyl, 2-chlorobenzyl, 3-chlorobenzyl, 4-chlorobenzyl, 4-aminobenzyl and the like are used.

(2) As $C_{1-4}$ alkyl having an optionally substituted 5- to 14-membered aromatic heterocyclic group consisting of 1 to 7% carbon atoms and a hetero atom selected from the group consisting of a nitrogen atom, an oxygen atom and a sulfur atom, for example, 2-pyridylmethyl, 3-pyridylmethyl, 4-pyridylmethyl, 4-imidazolemethyl and the like are used.

(3) As $C_{1-4}$ alkyl having an optionally substituted $C_{8-14}$ aromatic fused ring group, for example, 1-naphthylmethyl, 2-naphthylmethyl and the like are used.

(4) As $C_{1-4}$ alkyl having an optionally substituted 5- to 14-membered aromatic fused heterocyclic group consisting of 3 to 11 carbon atoms and a hetero atom selected from the group consisting of a nitrogen atom, an oxygen atom and a sulfur atom, for example, 3-indolemethyl, 1-formylindol-3-ylmethyl, 2-quinolylmethyl and the like are used.

(5) As $C_{1-4}$ alkyl having an optionally substituted nonaromatic cyclic hydrocarbon group having a carbon number of not more than 7, for example, cyclohexylmethyl and the like are used.

(6) As $C_{1-4}$ alkyl having an optionally substituted nonaromatic heterocyclic group having a carbon number of not more than 7, for example, piperidin-1-ylmethyl and the like are used.

(7) As $C_{1-4}$ alkyl having optionally substituted amino, for example, 2-aminoethyl, 3-aminopropyl, 4-aminobutyl, 4-acetamidobutyl and the like are used.

(8) As $C_{1-4}$ alkyl having optionally substituted guanidino, for example, 3-guanidinopropyl, 3-(N-tosyl)guanidinopropyl and the like are used.

(9) As $C_{1-4}$ alkyl having optionally substituted hydroxy, for example, hydroxymethyl, 1-hydroxyethyl, benzyloxymethyl and the like are used.

(10) As $C_{1-4}$ alkyl having optionally substituted carboxyl, for example, carboxylmethyl, 2-carboxylethyl, benzyloxycarbonylmethyl and the like are used.

(11) As $C_{1-4}$ alkyl having optionally substituted carbamoyl, for example, carbamoylmethyl, 2-carbamoylethyl, xanthylcarbamoyl and the like are used.

(12) As $C_{1-4}$ alkyl having optionally substituted sulfhydryl, for example, sulfhydrylmethyl, 2-(methylsulfhydryl)ethyl and the like are used.

(13) As unsubstituted $C_{1-4}$ alkyl, for example, methyl, ethyl, propyl, isopropyl, butyl, isobutyl, sec-butyl, tert-butyl and the like are used.

As $Q^3$, 4-hydroxybenzyl, 3-pyridylmethyl, 4-pyridylmethyl, methyl, isobutyl, hydroxymethyl, carboxymethyl, 4-aminobutyl and the like are preferably used, and particularly, 4-hydroxybenzyl, 3-pyridylmethyl, 4-pyridylmethyl and the like are preferably used.

As $Q^4$, carbamoylmethyl, 2-carbamoylethyl, 4-hydroxybenzyl, 4-imidazolemethyl, isobutyl, hydroxymethyl, 1-hydroxyethyl, carboxymethyl, 4-aminobutyl and the like are preferably used, and particularly, carbamoylmethyl, 2-carbamoylethyl, 4-hydroxybenzyl and the like are preferably used.

As $Q^5$, benzyl, 2-chlorobenzyl, 3-chlorobenzyl, 4-chlorobenzyl, 4-aminobenzyl, 2-pyridylmethyl, 3-pyridylmethyl, 4-pyridylmethyl, 1-naphthylmethyl, 2-naphthylmethyl, 3-indolemethyl, 1-formylindol-3-ylmethyl, 2-quinolylmethyl, cyclohexylmethyl, hydroxymethyl, 1-hydroxyethyl, methyl, isopropyl, isobutyl, sec-butyl, carboxymethyl, 4-aminobutyl and the like are preferably used, and benzyl, 2-chlorobenzyl, 3-chlorobenzyl, 4-chlorobenzyl, 4-aminobenzyl, 2-pyridylmethyl, 3-pyridylmethyl, 4-pyridylmethyl, 1-naphthylmethyl, 2-naphthylmethyl, 3-indolemethyl, 2-quinolylmethyl, cyclohexylmethyl, 1-hydroxyethyl, isopropyl, isobutyl, sec-butyl and the like are particularly preferably used.

As $Q^6$, methyl, hydroxymethyl, 1-hydroxyethyl, carbamoylmethyl, 2-carbamoylethyl and the like are preferably used, and carbamoylmethyl and the like are particularly preferably used.

As $Q^7$, 4-hydroxybenzyl, carbamoylmethyl, 3-pyridylmethyl and the like are preferably used, and 4-hydroxybenzyl and the like are particularly preferably used.

As $Q^8$, benzyl, 4-pyridylmethyl, 2-naphthylmethyl, 3-indolemethyl, hydroxymethyl, cyclohexylmethyl, sec-butyl, 1-hydroxyethyl and the like are preferably used, and 4-pyridylmethyl, 3-indolemethyl, sec-butyl and the like are particularly preferably used.

As $Q^9$, carbamoylmethyl and the like are preferably used.

As $Q^{10}$, 4-hydroxybenzyl, 3-indolemethyl, methyl, 1-hydroxyethyl, 3-guanidinopropyl and the like are preferably used, and 3-indolemethyl and the like are particularly preferably used.

As $Q^{11}$, carbamoylmethyl and the like are preferably used.

As $Q^{12}$, carbamoylmethyl and the like are preferably used.

$Y^1$-$Y^3$ are each a group represented by the formula —CON($J^{13}$)—, —CSN($J^{13}$)—, —C($J^{14}$)N($J^{13}$)- or —N($J^{13}$)CO— wherein $J^{13}$ and $J^{14}$ are each a hydrogen atom or $C_{1-3}$ alkyl.

As the $C_{1-3}$ alkyl for $J^{13}$ and $J^{14}$, methyl, ethyl, propyl and isopropyl are used.

As $J^{13}$, a hydrogen atom is preferable.
As $J^{14}$, a hydrogen atom is preferable.
As $Y^1$, a group represented by the formula —CONH— or —CH$_2$NH— and the like are preferable.
As $Y^2$, a group represented by the formula —CONH— or —CH$_2$NH— and the like are preferable.
As $Y^3$, a group represented by the formula —CONH— and the like are preferable.

$J^3$ and $Q^3$, $J^4$ and $Q^4$, $J^5$ and $Q^5$, $J^6$ and $Q^6$, $J^7$ and $Q^7$, $J^8$ and $Q^8$, $J^9$ and $Q^9$, $J^{10}$ and $Q^{10}$, $J^{11}$ and $Q^{11}$, or $J^{12}$ and $Q^{12}$ may be bonded to form a ring. In this case, $C(J^3)(Q^3)$, $C(J^4)(Q^4)$, $C(J^5)(Q^5)$, $C(J^6)(Q^6)$, $C(J^7)(Q^7)$, $C(J^8)(Q^8)$, $C(J^9)(Q^9)$, $C(J^{10})(Q^{10})$, $C(J^{11})(Q^{11})$ or $C(J^{12})(Q^{12})$ forms, for example, cyclopentane, cyclohexane, piperidine and the like.

$J^2$ and $Q^3$, $Y^1$ and $Q^4$, $Y^2$ and $Q^5$, $Y^3$ and $Q^6$, $J^2$ and $Q^7$, $Y^2$ and $Q^8$, $Y^3$ and $Q^9$, $J^2$ and $Q^{10}$, $Y^3$ and $Q^{11}$, or $J^2$ and $Q^{12}$ may be bonded to form a ring.

When $J^2$ and $Q^3$, $J^2$ and $Q^7$, $J^2$ and $Q^{10}$, or $J^2$ and $Q^{12}$ is bonded to form a ring, $J^2$-$C(J^3)(Q^3)$, $J^2$-$C(J^7)(Q^7)$, $J^2$-$C(J^{10})(Q^{10})$, or $J^2$-$C(J^{12})(Q^{12})$ forms, for example, pyrrolidine, piperidine or thiazolidine.

When $Y^1$ and $Q^4$, $Y^2$ and $Q^5$, $Y^3$ and $Q^6$, $Y^2$ and $Q^8$, $Y^3$ and $Q^9$, or $Y^3$ and $Q^{11}$ is bonded to form a ring, $Y^1C(J^4)(Q^4)$, $Y^2C(J^5)(Q^5)$, $Y^3C(J^6)(Q^6)$, $Y^2C(J^8)(Q^8)$, $Y^3C(J^9)(Q^9)$ or $Y^3C(J^{11})(Q^{11})$ forms, for example, pyrrolidine-2-carbonyl, piperidine-2-carbonyl or thiazolidine-4-carbonyl.

As the group represented by the formula $$J^1\text{-}J^2\text{-}C(J^3)(Q^3)Y^1C(J^4)(Q^4)Y^2C(J^5)(Q^5)Y^3C(J^6)(Q^6)C(=Z^{10})—,$$

Tyr Asn Trp Asn Ser- (SEQ ID NO: 47),
Tyr Asn Trp D-Asn Ser-,
Tyr Asn D-Trp Asn Ser-,
Tyr D-Asn Trp Asn Ser-,
D-Tyr Asn Trp Asn Ser-,
Tyr Lys Trp Asn Ser- (SEQ ID NO: 48),
Tyr Asp Trp Asn Ser- (SEQ ID NO: 49),
Tyr Tyr Trp Asn Ser- (SEQ ID NO: 50),
Tyr Leu Trp Asn Ser- (SEQ ID NO: 51),
Tyr Asn Ala Asn Ser- (SEQ ID NO: 52),
Tyr Asn Leu Asn Ser- (SEQ ID NO: 53),
Tyr Asn Ser Asn Ser- (SEQ ID NO: 54),
Tyr Asn Asp Asn Ser- (SEQ ID NO: 55),
Tyr Asn Lys Asn Ser- (SEQ ID NO: 56),
Ala Asn Trp Asn Ser- (SEQ ID NO: 57),
Leu Asn Trp Asn Ser- (SEQ ID NO: 58),
Ser Asn Trp Asn Ser- (SEQ ID NO: 59),
Asp Asn Trp Asn Ser- (SEQ ID NO: 60),
Lys Asn Trp Asn Ser- (SEQ ID NO: 61),
Tyr Asn Trp(For) Asn Ser- (SEQ ID NO: 62),
D-Tyr Asn D-Trp Asn Ser-,
D-Tyr Asn Ala Asn Ser-,
D-Tyr Asn Ser Asn Ser-,
D-Tyr Asn Cha Asn Ser-,
D-Tyr Asn Thr Asn Ser-,
D-Tyr Asn Ile Asn Ser-,
D-Tyr Gln Trp Asn Ser-,
D-Tyr Thr Trp Asn Ser-,
D-Tyr Asn Val Asn Ser-,
D-Tyr D-Asn Trp Asn Ser-,
D-Tyr D-Asn D-Trp Asn Ser-,
D-Tyr Asn Phe Asn Ser-,
D-Tyr Asn Nal(1) Asn Ser-,
D-Tyr Asn Nal(2) Asn Ser-,
D-Tyr Asn Phe(2Cl) Asn Ser-,
D-Tyr Asn Phe(3Cl) Asn Ser-,
D-Tyr Asn Phe(4Cl) Asn Ser-,
D-Tyr Asn Phe(4NH$_2$) Asn Ser-,
D-Tyr Asn Pya(3) Asn Ser-,
D-Tyr D-Asn Phe Asn Ser-,
D-Tyr D-Asn Cha Asn Ser-,
D-Tyr D-Asn Thr Asn Ser-,
D-Tyr Asn Pya(2) Asn Ser-,
D-Tyr Asn Pya(4) Asn Ser-,
D-Tyr D-Ser Trp Asn Ser-,
D-Tyr D-His Trp Asn Ser-,
D-Pya(3) D-Asn Cha Asn Ser-,
D-Pya(3) D-Tyr Cha Asn Ser-,
TyrΨ(CH$_2$NH)Asn Trp Asn Ser- (SEQ ID NO: 63),
D-Tyr AsnΨ(CH$_2$NH)Trp Asn Ser-,
TyrΨ(CH$_2$NH)Asn D-Trp Asn Ser-,
D-Tyr Asn Ala(2-Qui) Asn Ser-,
D-Tyr Asn D-Pya(4) Asn Ser-,
D-Tyr D-Asn Pya(4) Asn Ser-,
Tyr D-Asn Cha Asn Ser-,
D-Tyr D-Asn Thr Asn Ser-,
D-Tyr D-Asn Pya(4) Asn Ser- and the like are preferable.

As the group represented by the formula

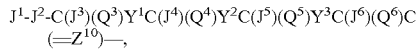

Fmoc Asn Trp Asn Ser- (SEQ ID NO: 64),
D-Asn Trp Asn Ser-,
D-Tyr Trp Asn Ser-,
D-Tyr D-Trp Asn Ser-,
D-Tyr Ser Asn Ser-,
D-Tyr Thr Asn Ser-,
D-Tyr Ile Asn Ser-,
D-Tyr Phe Asn Ser-,
D-Tyr Nal(2) Asn Ser-,
D-Pya(3) Phe Asn Ser-,
D-Pya(3) Trp Asn Ser-,
D-Tyr D-Pya(4) Asn Ser-,
D-Asn Cha Asn Ser- and the like are preferable.

As the group represented by the formula $$J^1\text{-}J^2\text{-}C(J^{10})(Q^{10})Y^3C(J^{11})(Q^{11})C(=Z^{10})—,$$

Fmoc Trp Asn Ser-,
Boc Tyr Asn Ser-,
Tyr Asn Ser-,
D-Trp Asn Ser-,
Ac Trp Asn Ser-,
Amidino Trp Asn Ser-,
Ac Ala Asn Ser-,
Ac Arg Asn Ser-,
Ac Thr Asn Ser- and the like are preferable.

As the group represented by the formula $$J^1\text{-}J^2\text{-}C(J^{12})(Q^{12})C(=Z^{10})—,$$

Fmoc Asn Ser-,
3-(Indol-3-yl)propionyl Asn Ser-,
3-Indolecarbonyl Asn Ser-,
3-Indoleacetyl Asn Ser-,
4-(Indol-3-yl)butyryl Asn Ser-,
Diphenylacetyl Asn Ser-,
Hexanoyl Asn Ser-,
Cyclohexanecabonyl Asn Ser-,
2-(Indol-3-yl)ethylcabamoyl Asn Ser-,
3-Pyridylpropionyl Asn Ser-,
4-Imidzoleacetyl Asn Ser-, Piperidinecarbonyl Asn Ser-,
1-Piperidineacetyl Asn Ser-,
1-Methyl-1-piperidinioacetyl Asn Ser-,
1-Pyridinioacetyl Asn Ser-,
D-Glucronyl Asn Ser- and the like are preferable.

P is preferably a group represented by $J^1$- and, for example, a substituent (e.g., benzoyl) containing a ring group optionally having a substituent (e.g., halogen etc.) and the like are preferable.

The compound having GPR54 agonist activity of the present invention may be amide($-CONH_2$), carboxyl($-COOH$), carboxylate($-COO^-$), alkylamide($-CONHR$) or ester ($-COOR$), and amide($-CONH_2$) is particularly preferable. Examples of R of ester or alkylamide include $C_{1-6}$ alkyl such as methyl, ethyl, n-propyl, isopropyl, n-butyl and the like, $C_{3-8}$ cycloalkyl such as cyclopentyl, cyclohexyl and the like, $C_{6-12}$ aryl such as phenyl, α-naphthyl and the like, phenyl-$C_{1-2}$ alkyl such as benzyl, phenethyl, benzhydryl and the like, or $C_{7-14}$ aralkyl such as α-naphthyl-$C_{1-2}$ alkyl (e.g., α-naphthylmethyl etc.), and the like, pivaloyloxymethyl widely used as oral ester and the like.

As for X

In the present invention, the X moiety does not include an amide bond. The X moiety basically requires a main chain for mimicking full-length dipeptide and an alkyl side chain corresponding to an isobutyl group of Leu. The main chain has an atom number of 5-7.

X is specifically represented by the following formula (II):

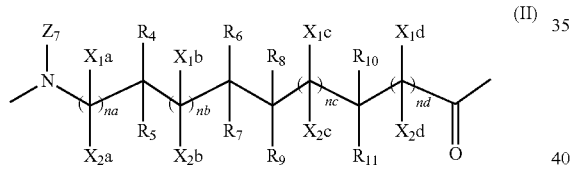

(II)

wherein,
na-nd are the same or different and each is an integer of 0-2 wherein the total of na, nb, nc and nd is 0-2, $X_1a$-$X_1d$ and $X_2a$-$X_2d$ are the same or different and each is a hydrogen atom, hydroxy, a halogen atom or an optionally substituted lower alkyl group, $Z_7$ is a hydrogen atom or an optionally substituted hydrocarbon group. The optionally substituted hydrocarbon group is the above-mentioned optionally substituted $C_{1-6}$ alkyl, the above-mentioned optionally substituted $C_{2-6}$ alkenyl, the above-mentioned optionally substituted $C_{2-6}$ alkynyl, the above-mentioned optionally substituted $C_{1-6}$ alkoxy, formyl, the above-mentioned optionally substituted $C_{1-6}$ alkyl-carbonyl, the above-mentioned optionally substituted $C_{3-8}$ cycloalkyl-carbonyl, the above-mentioned optionally substituted $C_{1-6}$ alkoxy-carbonyl or the above-mentioned optionally substituted $C_{1-6}$ alkylsulfonyl. $R_4$-$R_{11}$ are the same or different and each is a hydrogen atom, hydroxy, a halogen atom or optionally substituted lower alkyl. The optionally substituted lower alkyl is specifically methyl, halomethyl, ethyl, n-propyl, n-butyl, n-pentyl, n-hexyl or branched alkyl thereof. Further specifically, isopropyl, isobutyl or sec-butyl is preferable. In addition, $R_7$ and $R_8$ may form a bond in combination, and $R_9$ and $R_{10}$ may form a bond in combination. Preferably, X is a moiety represented by the following structural formula (III):

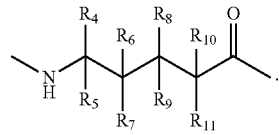

(III)

wherein $R_4$-$R_{11}$ are the same or different and each is a hydrogen atom, hydroxy, a halogen atom or optionally substituted lower alkyl. In addition, $R_7$ and $R_8$ may form a bond in combination, and $R_9$ and $R_{10}$ may form a bond in combination.

Of these, X is preferably a moiety selected from the following structural formula group (IV):

(IV)

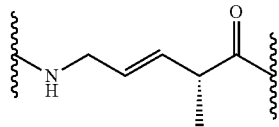

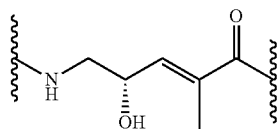

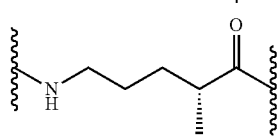

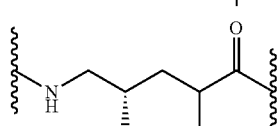

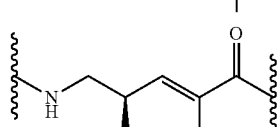

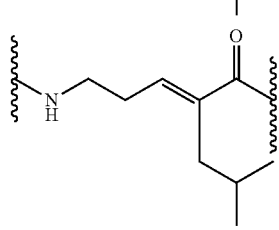

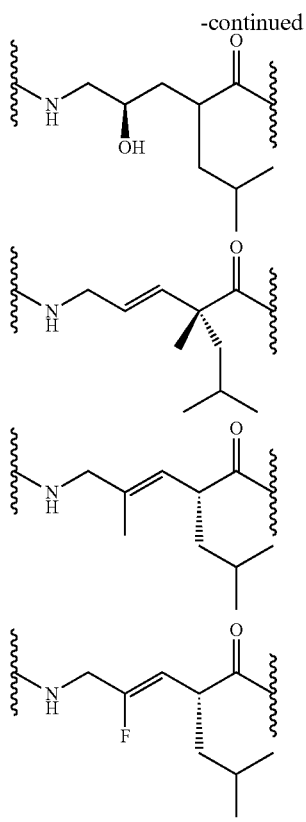

Examples of the preferable compound capable of exhibiting a superior GPR54 agonist activity in the present invention include a compound of the following formula (V):

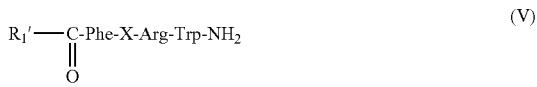

wherein $R_1'$ is 2-pyrrolyl, 4-methoxyphenyl, 4-chlorophenyl or 4-fluorophenyl, and X is as defined above.

The compound of the present invention obtained as mentioned above has a GPR54 agonist activity. The agonist activity in the present invention includes both activities of full agonist and partial agonist.

In addition, the compound of the present invention represented by the above-mentioned formula (I) also encompasses isomers such as geometric isomer, stereoisomer, optical isomer and the like.

2. Pharmaceutical Composition

The present invention also provides a pharmaceutical composition containing a compound and/or a pharmaceutically acceptable salt thereof obtained by the above-mentioned method as an active ingredient, and a pharmaceutically acceptable excipient, diluent or carrier.

A salt of metastin derivative (I) of the present invention includes, for example, a metal salt, an ammonium salt, a salt with an organic base, a salt with an inorganic acid, a salt with an organic acid, a salt with basic or acidic amino acid, etc. Suitable examples of the metal salt include an alkali metal salt such as a sodium salt, a potassium salt, etc.; an alkaline earth metal salt such as a calcium salt, a magnesium salt, a barium salt, etc.; an aluminum salt, etc. Suitable examples of the salts with an organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine, etc. Suitable examples of the salts with an inorganic acid include salts with hydrochloric acid, hydrobromic acid, nitric acid, sulfuric acid, phosphoric acid, etc. Suitable examples of the salts with an organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, etc. Suitable examples of the salts with basic amino acid include salts with arginine, lysine, ornithine, etc. Suitable examples of the salts with acidic amino acid include salts with aspartic acid, glutamic acid, etc.

Among these, pharmaceutically acceptable salts are preferred. For example, when the compound has acidic functional group, preferred are inorganic salts such as an alkali metal salt (e.g., sodium salt, potassium salt, etc.), an alkaline earth metal salt (e.g., calcium salt, magnesium salt, barium salt, etc.), an ammonium salt, etc. When the compound has a basic functional group, preferred are salts with an inorganic acid such as hydrochloric acid, hydrobromic acid, nitric acid, sulfuric acid, phosphoric acid, etc., or salts with an organic acid such as acetic acid, phthalic acid, fumaric acid, oxalic acid, tartaric acid, maleic acid, citric acid, succinic acid, methanesulfonic acid, p-toluenesulfonic acid, etc.

The metastin derivative (I) of the present invention can be produced according to a synthesis method of peptide known per se. The synthesis method of peptide may be any of a solid phase synthesis process and a liquid phase synthesis process. That is, a desired peptide can be produced by condensing a partial peptide or amino acid capable of constituting the peptide of the present invention with the remaining portion, and removing any protecting group the resultant product may have. As known condensation methods and protecting group removal method, for example, the methods indicated in 1) to 5) below can be mentioned:

1) M. Bodanszky and M. A. Ondetti: Peptide Synthesis, Interscience Publishers, New York (1966)
2) Schroeder and Luebke: The Peptide, Academic Press, New York (1965)
3) Nobuo Izumiya, et al.: Peptide Gosei-no-Kiso to Jikken (Basics and experiments of peptide synthesis), published by Maruzen Co. (1975)
4) Haruaki Yajima and Shunpei Sakakibara: Seikagaku Jikken Koza (Biochemical Experiment) 1, Tanpakushitsu no Kagaku (Chemistry of Proteins) IV, 205 (1977)
5) Haruaki Yajima, ed.: Zoku Iyakuhin no Kaihatsu (A sequel to Development of Pharmaceuticals), Vol. 14, Peptide Synthesis, published by Hirokawa Shoten.

After the reaction, moreover, the peptide of the present invention can be purified and isolated by a general purification method, for example, solvent extraction.distillation.column chromatography.liquid chromatography.recrystallization and the like in combination. When the peptide is obtained as a free compound by the above-mentioned method, it can be converted into a desired salt by a known method; conversely, when it is obtained as a salt, it can be converted into a free form by a known method.

For the condensation of protected amino acids or peptides, various activation reagents usable for peptide synthesis can be used, with particular preference given to trisphosphonium salts, tetramethyluronium salts, carbodiimides and the like. Examples of the trisphosphonium salts include benzotriazol-1-yloxytris(pyrrolidino)phosphonium hexafluorophosphate (PyBOP), bromotris(pyrrolidino)phosphonium hexafluorophosphate (PyBroP), 7-azabenzotriazol-1-yloxytris(pyrrolidino)phosphonium hexafluorophosphate (PyAOP), and examples of the tetramethyluronium salts include 2-(1H-benzotriazol-1-yl)-1,1,3,3-hexafluorophosphate (HBTU), 2-(7-azabenzotriazol-1-yl)-1,1,3,3-hexafluorophosphate (HATU), 2-(1H-benzotriazol-1-yl)-1,1,3,3-tetramethyluroniumtetrafluoroborate (TBTU), 2-(5-norbornene-2,3-dicarboxylmide)-1,1,3,3-tetramethyluroniumtetrafluoroborate (TNTU), O—(N-succinimidyl)-1,1,3,3-tetramethyluroniumtetrafluoroborate (TSTU), and examples of the carbodiimides include DCC, N,N'-diisopropylcarbodiimide(DIPCDI), N-ethyl-N'-(3-dimethylaminopropyl)carbodiimide hydrochloride (EDCI.HCl) and the like. For condensation by these, addition of racemization suppressant (e.g., HONB, HOBt, HOAt, HOOBt etc.) is preferable. As the solvents to be used in the condensation can be selected as appropriate from among the solvents known to be usable for peptide condensation reactions. For example, acid amides such as anhydrous or water-containing N,N-dimethylformamide, N,N-dimethylacetamide, and N-methylpyrrolidone; halogenated hydrocarbons such as methylene chloride and chloroform; alcohols such as trifluoroethanol and phenol; sulfoxides such as dimethyl sulfoxide; tertiary amines such as pyridine; ethers such as dioxane and tetrahydrofuran; nitriles such as acetonitrile and propionitrile; esters such as methyl acetate and ethyl acetate; appropriate mixtures of these solvents, and the like can be used. Reaction temperature is selected as appropriate from the range known to be useful for peptide bond formation reactions, and is normally selected as appropriate from the range of about −20° C. to about 50° C. The activated amino acid derivative is normally used in an excess of 1.5 to 6 times. For solid phase synthesis, when a test using the ninhydrin reaction reveals insufficient condensation, the condensation can be completed by repeating the condensation reaction without splitting off the protecting groups. When the condensation is yet insufficient even after repeating the reaction, unreacted amino acids can be acylated with acetic anhydride, acetylimidazole etc. so that an influence on the subsequent reactions can be avoided.

Examples of the protecting groups for the amino groups of the starting amino acid include Z, Boc, tert-pentyloxycarbonyl, isobornyloxycarbonyl, 4-methoxybenzyloxycarbonyl, Cl—Z, Br—Z, adamantyloxycarbonyl, trifluoroacetyl, phthaloyl, formyl, 2-nitrophenylsulphenyl, diphenylphosphinothioyl, Fmoc and the like. As carboxyl-protecting group, for example, $C_{1-6}$ alkyl group, $C_{3-8}$ cycloalkyl group and $C_{7-14}$ aralkyl group, recited above for R, as well as allyl, 2-adamantyl, 4-nitrobenzyl, 4-methoxybenzyl, 4-chlorobenzyl, phenacyl group and benzyloxycarbonyl hydrazide, tert-butoxycarbonyl hydrazide, trityl hydrazide and the like can be mentioned.

The hydroxyl group of serine or threonine can be protected by, for example, esterification or etherification. Examples of groups suitable for this esterification include groups derived from organic acid such as lower ($C_{2-4}$) alkanoyl groups such as acetyl group, aroyl groups such as benzoyl group, etc. As examples of groups suitable for the etherification, for example, benzyl, tetrahydropyranyl, tert-butyl, trityl (Trt) and the like can be mentioned.

Examples of the protecting group of the phenolic hydroxyl group of tyrosine include Bzl, 2,6-dichlorobenzyl, 2-nitrobenzyl, Br—Z, tert-butyl and the like.

Examples of the protecting group of the imidazole of histidine include Tos, 4-methoxy-2,3,6-trimethylbenzenesulfonyl (Mtr), DNP, Bom, Bum, Boc, Trt, Fmoc and the like.

Examples of the protecting group of the guanidino group of arginine include Tos, Z, 4-methoxy-2,3,6-trimethylbenzenesulfonyl (Mtr), p-methoxybenzenesulfonyl (MBS), 2,2,5,7, 8-pentamethylchromane-6-sulfonyl (Pmc), mesitylene-2-sulfonyl (Mts), 2,2,4,6,7-pentamethyldihydrobenzofuran-5-sulfonyl (Pbf), Boc, Z, $NO_2$ and the like.

Examples of the protecting group of the side chain amino group of lysine include Z, Cl—Z, trifluoroacetyl, Boc, Fmoc, Trt, Mtr, 4,4-dimethyl-2,6-dioxocyclohexylidene)ethyl (Dde) and the like.

Examples of the indolyl-protecting group of tryptophan include formyl (For), Z, Boc, Mts, Mtr and the like.

Examples of the protecting group of asparagine and glutamine include Trt, xanthyl (Xan), 4,4'-dimethoxybenzhydryl (Mbh), 2,4,6-trimethoxybenzyl (Tmob) and the like.

Examples of the activated carboxyl group in the starting material include corresponding acid anhydrides, azides and activated esters (esters with alcohols (e.g., pentachlorophenol, 2,4,5-trichlorophenol, 2,4-dinitrophenol, cyanomethyl alcohol, para-nitrophenol, HONB, N-hydroxysuccimide, 1-hydroxybenzotriazole (HOBt), 1-hydroxy-7-azabenzotriazole (HOAt))]. Examples of the activated amino group in the starting material include corresponding phosphorous amides.

As examples of the method used to remove (split off) the protecting group, catalytic reduction in a hydrogen gas stream in the presence of a catalyst such as Pd-black or Pd-carbon; acid treatment with anhydrous hydrogen fluoride, methanesulfonic acid, trifluoromethanesulfonic acid, trifluoroacetic acid, trimethylsilane bromide (TMSBr), trimethylsilyltrifluoromethanesulfonate, tetrafluoroboric acid, tris(trifluoro) boron, tribromide boron, or a mixed solution thereof; treatment with a base such as diisopropylethylamine, triethylamine, piperidine or piperazine; reduction with sodium in liquid ammonia, and the like can be mentioned. The reaction of splitting off of the protecting group by the above-described acid treatment is normally performed at a temperature of about −20° C. to 40° C. In the acid treatment, addition of a cation scavenger such as anisole, phenol, thioanisole, meta-cresol, para-cresol etc., dimethylsulfide, 1,4-butanedithiol, 1,2-ethanedithiol etc. is effective. The 2,4-dinitrophenyl group used as the protecting group of the imidazole moiety of histidine is removed by thiophenol treatment; the formyl group used as the protecting group of the indole moiety of tryptophan is removed by alkali treatment with dilute sodium hydroxide solution, dilute ammonia or the like, as well as by the above-described acid treatment in the presence of 1,2-ethanedithiol, 1,4-butanedithiol or the like.

A protecting method and a protecting group of a functional group that should not be involved in the reaction of raw materials, a method of removing the protecting group, a method of activating a functional group involved in the reaction, and the like can be appropriately selected from among publicly known protecting groups or publicly known means.

In a method of obtaining an amide of peptide, for example, solid phase synthesis is performed by using a resin for amide synthesis, or the α-carboxyl group of the C terminal amino acid is first amidated, and a peptide chain is elongated from amino group side to a desired chain length, thereafter a peptide in which only the protecting group of the N terminal α-amino group of the peptide chain has been removed and a peptide (or amino acid) in which only the protecting group of the C terminal carboxyl group has been removed are prepared, and the two peptides are condensed in a mixed solvent described above. For details about the condensation reaction, the same as above applies. After the protected peptide obtained by the condensation is purified, all protecting groups can be removed by the above-described method to yield a desired crude polypeptide. By purifying this crude peptide using various publicly known means of purification, and freeze-drying the main fraction, a desired amide of the peptide can be prepared.

When the metastin derivative (I) of the present invention is present as a configurational isomer (stereoisomer), diastereomer, conformer or the like, each can be isolated by the above separation and purification methods on demand. In addition, when the compound of the present invention is in the form of racemates, they can be separated into S- and R-forms by any conventional optical resolution.

When the metastin derivative (I) of the present invention includes stereoisomers, both the isomers alone and mixtures of each isomers are included in the scope of the present invention.

In addition, the metastin derivative (I) of the present invention may be a hydrate or non-hydrate.

The metastin derivative (I) of the present invention may be labeled with an isotope (e.g., $^3$H, $^{14}$C, $^{35}$S and the like) or the like.

The prodrug of the metastin derivative (I) or a salt thereof of the present invention (hereinafter to be abbreviated as metastin derivative (I) of the present invention) means a metastin derivative which is converted to metastin derivative (I) of the present invention under the physiological condition in the living body by a reaction with an enzyme, a gastric acid, or the like, that is, a metastin derivative which is converted to metastin derivative of the present invention by enzymatic oxidation, reduction, hydrolysis, etc.; a metastin derivative which is converted to metastin derivative (I) of the present invention by hydrolysis with gastric acid, etc.

The prodrug of the metastin derivative (I) of the present invention includes a metastin derivative wherein an amino group of the metastin derivative (I) is modified with acyl, alkyl or phosphoryl (e.g., a metastin derivative wherein an amino group of metastin derivative (I) of the present invention is modified with eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl or tert-butyl, etc.); a metastin derivative wherein a hydroxyl group of the metastin derivative (I) of the present invention is modified with acyl, alkyl, phosphoric acid or boric acid (e.g., a metastin derivative wherein a hydroxyl group of the metastin derivative (I) is modified with acetyl, palmitoyl, propanoyl, pivaloyl, succinyl, fumaryl, alanyl or dimethylaminomethylcarbonyl, etc.); a metastin derivative wherein a carboxy group of the metastin derivative (I) of the present invention is modified to ester or amide (e.g., a metastin derivative wherein a carboxy group of the metastin derivative (I) of the present invention is modified to ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester or methylamide, etc.); and the like. These metastin derivatives can be produced from the metastin derivative (I) of the present invention by a method known per se.

In addition, the prodrug of the metastin derivative (I) of the present invention may be a derivative, which is converted into the metastin derivative (I) of the present invention under physiological conditions, as described in "Pharmaceutical Research and Development", Vol. 7 (Drug Design), pp. 163-198 (1990), published by Hirokawa Publishing Co.

Since the metastin derivative (I) or a salt thereof or a prodrug thereof of the present invention (hereinafter sometimes to be abbreviated as the compound of the present invention) has a cancer metastasis suppressing activity or cancer growth suppressing activity, it is useful as a cancer metastasis suppressant or cancer growth suppressant, for example, a pharmaceutical composition such as an agent for the prophylaxis or treatment of various cancers (e.g., lung cancer, gastric cancer, liver cancer, pancreatic cancer, bowel cancer, rectal cancer, colon cancer, prostate cancer, ovarian cancer, cervical cancer, breast cancer etc.) and the like.

In addition, since the compound of the present invention has a pancreatic function regulating action, it is useful as a pancreatic function regulator such as an agent for the prophylaxis or treatment of various pancreas diseases (e.g., acute or chronic pancreatitis, pancreatic cancer etc.).

Moreover, since the compound of the present invention has a placental function regulating action, it is useful as a placental function regulator, for example, a pharmaceutical composition such as an agent for the prophylaxis or treatment of villous cancer, hydatidiform mole, invasive mole, abortion, underdevelopment of fetus, glucose metabolism disorder, abnormal lipid metabolism or induction of childbirth, and the like.

Furthermore, since the compound of the present invention has a blood glucose increasing action, pancreatic glucagon secretagogue action and urine production promoting action, it is useful as a hyperglycemic drug, pancreatic glucagon secretagogue or agent for promoting urine production, for example, a pharmaceutical composition such as an agent for the prophylaxis or treatment of obesity, hyperlipidemia, type 2 diabetes, hypoglycemia, hypertension, diabetes neuropathy, diabetes nephropathy, diabetes retinopathy, edema, dysuria, insulin resistance, unstable diabetes, fatty atrophy, insulin allergy, insulinoma, arteriosclerosis, thrombotic disease or lipotoxicity, and the like.

Moreover, since the compound of the present invention has a gonadotropic hormone (e.g., FSH, LH etc.) secretagogue action, sex hormone [e.g., androgen (e.g., testosterone, androstenedione etc.), estrogen (e.g., estradiol, estrone etc.), progesterone etc.] secretagogue action, gonadal function improving effect, inducing or stimulating ovulation, sexual maturation effect and the like, it can be used, for example, as a gonadal function improver, agent for inducing or stimulating ovulation, gonadotropic hormone secretagogue, sex hormone secretagogue, or an agent for the prophylaxis or treatment of hormone-dependent cancer [e.g., prostate cancer, breast cancer etc.], infertility [e.g., irregular menstruation, dysmenorrhea, amenorrhea, weight-loss-related amenorrhea, secondary amenorrhea, anovulation, ovary hypofunction, gonadal hypofunction, spermatozoon formation disorder, sexual dysfunction (e.g., impotence etc.), genital atrophy, testis atrophy, testis dysfunction, azoospermia, hypoandrogenemia etc.], endometriosis, hysteromyoma and the like.

Furthermore, the compound of the present invention is useful as an agent for the prophylaxis or treatment of Alzheimer's disease, mild cognitive impairment, etc. and the like.

Moreover, the compound of the present invention shows superior blood stability as compared to native type metastin, for example, metastin 54 (1-54) and metastin 10 (45-54).

A pharmaceutical composition comprising the compound of the present invention can be produced according to the method described in JP-A-2004-217651, and those of ordinary skill in the art can also determine the dose, administration route and the like appropriately from the description of JP-A-2004-217651.

Moreover, the compound of the present invention can be used in combination with drugs other than the compound of the present invention.

As the drugs that can be used in combination with the compound of the present invention (hereinafter sometimes to be abbreviated as a concomitant drug), for example, chemotherapeutic agent for cancer treatment, hormonal therapeutic agent, immunotherapeutic agent, and the like can be mentioned.

As examples of said "chemotherapeutic agents", there may be mentioned alkylating agents, antimetabolites, anticancer antibiotics, plant-derived anticancer agents, and the like.

As examples of "alkylating agents", there may be mentioned nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, sodium estramustine phosphate, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, carboquone, adozelesin, cystemustine, bizelesin, and the like.

As examples of "antimetabolites", there may be mentioned mercaptopurine, 6-mercaptopurine riboside, thioinosine, methotrexate, enocitabine, cytarabine, cytarabine ocfosfate, ancitabine hydrochloride, 5-FU drugs (e.g., fluorouracil, tegafur, UFT, doxifluridine, carmofur, gallocitabine, emmitefur, and the like), aminopterin, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, thiazophrine, ambamustine, and the like.

As examples of "anticancer antibiotics", there may be mentioned actinomycin-D, actinomycin-C, mitomycin-C, chromomycin-A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride, and the like.

As examples of "plant-derived anticancer agents", there may be mentioned etoposide, etoposide phosphate, vinblastine sulfate, vincristine sulfate, vindesine sulfate, teniposide, paclitaxel, docetaxel, vinorelbine, and the like.

As examples of said "hormonal therapeutic agents," there may be mentioned fosfestrol, diethylstylbestrol, chlorotrianiserin, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogens (e.g., tamoxifen citrate, toremifene citrate, and the like), pill preparations, mepitiostane, testrolactone, aminoglutethimide, LH-RH agonists (e.g., goserelin acetate, buserelin, leuprorelin, and the like), droloxifene, epitiostanol, ethinylestradiol sulfonate, aromatase inhibitors (e.g., fadrozole hydrochloride, anastrozole, retrozole, exemestane, vorozole, formestane, and the like), anti-androgens (e.g., flutamide, bicartamide, nilutamide, and the like), 5α-reductase inhibitors (e.g., finasteride, episteride, and the like), adrenocorticohormone drugs (e.g., dexamethasone, prednisolone, betamethasone, triamcinolone, and the like), androgen synthesis inhibitors (e.g., abiraterone, and the like), retinoid and drugs that retard retinoid metabolism (e.g., liarozole, and the like), etc. and LH-RH agonists (e.g., goserelin acetate, buserelin, leuprorelin) are preferable.

As examples of said "immunotherapeutic agents (BRM)", there may be mentioned picibanil, krestin, sizofuran, lentinan, ubenimex, interferons, interleukins, macrophage colony-stimulating factor, granulocyte colony-stimulating factor, erythropoietin, lymphotoxin, BCG vaccine, *Corynebacterium parvum*, levamisole, polysaccharide K, procodazole, and the like.

Combination of the compound of the present invention with a concomitant drug can afford the following excellent effects:

(1) a dose can be reduced as compared with single administration of the compound of the present invention or a concomitant drug, (2) according to symptoms of patient (mild symptoms, severe symptoms, etc.), a drug to be combined with the compound of the present invention can be selected;

(3) by selecting a concomitant drug which has different mechanism of action from that of the compound of the present invention, the therapeutic period can be designed longer;

(4) by selecting a concomitant drug which has different mechanism of action from that of the compound of the present invention, continuation of therapeutic effects can be obtained; and (5) by combining the compound of the present invention and a concomitant drug, excellent effects such as synergic effects can be obtained.

In the following, a combined use of the compound of the present invention with a concomitant drug is referred to as "the combination agent of the present invention".

When using the combination agent of the present invention, the administration time of the compound of the present invention and the concomitant drug is not restricted, and the compound of the present invention or a pharmaceutical composition thereof and the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the concomitant drug is not particularly limited, and the compound of the present invention and the concomitant drug only need to be combined on administration. Examples of such administration mode include the following:

(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The concomitant drug of the present invention can be produced as described in JP-A-2004-217651, and those of ordinary skill in the art can also appropriately determine the administration route, administration method, administration mode, dose and the like from the description of JP-A-2004-217651.

3. Application

The compound of the present invention specifically binds to GPR54, which is a 7-transmembrane G protein-coupled receptor, to activate the receptor, and can enhance the action of metastin (aka: kisspeptin), which is an endogenous ligand. Accordingly, the compound of the present invention can be preferably used for diseases for which activation of GPR54 and enhancement of the metastin action associated therewith are effective for the prophylaxis or treatment thereof (including treatments aiming at improvement, mitigation or cure of symptom). Specifically, the following diseases can be mentioned.

Metastin is an endogenous ligand relating to cancer metastasis, sexual function control and the like.

Metastin has been reported to significantly inhibit metastasis of lung transitional GPR54-expression melanoma cells, to be able to suppress migration of pancreatic cancer cells, and the like. Therefore, a pharmaceutical composition containing the compound of the present invention can be used as an agent for suppressing metastasis of cancers such as melanoma, pancreatic cancer and the like.

Furthermore, since the compound of the present invention has suppressive action on decreased sexual function, it can also improve control of abnormal secretion of sex hormone or gonadotropic hormone. In addition, not intending to limit the interpretation of the present invention, for example, the compound of the present invention is expected to show an effect as a therapeutic agent for fertility by acting as a GPR54 agonist, which suppresses migration of cells and promotes nidation of fertilized egg.

Moreover, Jean-Marc Navenot et al., Cancer Res. 2004; 65:22. Nov. 15, 2005 has clarified that kisspeptin-10 (kp-10) derived from KiSS-1 gene product activates GPR54 and suppresses the function of CXCR4. CXCR4 is a human receptor protein encoded by CXCR4 gene as one of the G protein-coupled receptor proteins, and is known to be involved in various diseases such as metastasis or growth of cancer, chronic articular rheumatism, lung fibrosis, B cell chronic lymphocytic leukemia, HIV infection and the like.

Therefore, a pharmaceutical composition containing the compound of the present invention is expected to suppressively act on diseases involving CXCR4. Examples of the disease involving CXCR4 include AIDS, B cell chronic lymphocytic leukemia, types of cancer expressing CXCR4, for example, mouth cavity cancer, pharyngeal cancer, lip cancer, cancer of the tongue, gingiva cancer, nasopharynx cancer, esophagus cancer, gastric cancer, small intestinal cancer, bowel cancer including colon cancer, liver cancer, gallbladder cancer, pancreatic cancer, nasal cavity cancer, lung cancer, osteosarcoma, soft tissue cancer, skin cancer, melanoma, breast cancer, uterine cancer, ovarian cancer, prostate cancer, testis cancer, penile cancer, urinary bladder cancer, kidney cancer, brain tumor, thyroid cancer, lymphoma, leukemia, chronic articular rheumatism and the like. In addition, since involvement of CXCR4 is also suggested in trauma such as burn and the like, it is considered that a pharmaceutical composition containing the compound of the present invention can be applied with the aim of curing burn and the like.

Therefore, the metastin derivative (I) of the present invention or a salt thereof or a prodrug thereof is useful, for example, as a hyperglycemic drug, pancreatic glucagon secretagogue or agent for promoting urine production. Furthermore, a metastin receptor agonist is useful as an agent for the prophylaxis or treatment of, for example, obesity, hyperlipidemia, type 2 diabetes, hypoglycemia, hypertension, diabetic neuropathy, diabetic nephropathy, diabetic retinopathy, edema, dysuria, insulin resistance, unstable diabetes, fatty atrophy, insulin allergy, insulinoma, arteriosclerosis, thrombotic disease or lipotoxicity.

The metastin derivative (I) of the present invention or a salt thereof or a prodrug thereof is also useful as a hypoglycemic agent, agent for suppressing pancreatic glucagon secretion or agent for suppressing urine production. Furthermore, a metastin receptor antagonist can be used as an agent for the prophylaxis or treatment of, for example, diabetes, impaired glucose tolerance, ketosis, acidosis, diabetic neuropathy, diabetic nephropathy, diabetic retinopathy, frequent urination, enuresis, hyperlipidemia, genital disorder, skin disease, arthropathy, osteopenia, arteriosclerosis, thrombotic disease, dyspepsia, memory or learning disorder.

The metastin derivative (I) of the present invention or a salt thereof or a prodrug thereof may form a salt and, for example, a salt with a physiologically acceptable acid (e.g., inorganic acid, organic acid etc.), a base (e.g., alkali metal etc.) or the like is used, and a physiologically acceptable acid addition salt is particularly preferable. As such salt, salts with inorganic acid (e.g., hydrochloric acid, phosphoric acid, hydrobromic acid, sulfuric acid etc.), salts with organic acid (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid etc.) and the like are used.

When the metastin derivative (I) of the present invention or a salt thereof or a prodrug thereof is used as the aforementioned agent for the prophylaxis or treatment, it can be practiced according to a conventional means. For example, it can be prepared into tablet, capsule, elixir, microcapsule, sterile solution, suspension and the like in the same manner as in the aforementioned pharmaceutical composition containing metastin.

The thus-obtained preparation is safe and low toxic, and can be administered to, for example, human or warm-blooded animal (e.g., mouse, rat, rabbit, sheep, swine, bovine, horse, chicken, cat, dog, monkey, chimpanzee etc.).

The dose of the substance varies depending on the action, target disease, administration subject, administration route and the like. For example, for oral administration of a metastin receptor agonist, the compound is generally administered in about 0.1-100 mg, preferably about 1-50 mg, more preferably about 1-20 mg, to an adult (per body weight 60 kg) per day. For parenteral administration, the dose of the substance varies depending on the administration subject, target disease and the like. For example, when a metastin receptor agonist is generally administered to an adult (per body weight 60 kg) in the form of an injection, the compound is preferably administered in about 0.01-30 mg, preferably about 0.1-20 mg, more preferably about 0.1-10 mg, by intravenous injection. In the case of other animals, an amount corresponding to the amount per body weight 60 kg can be administered.

The present invention is explained in detail in the following by referring to Examples, Formulation Examples and Experimental Examples. However, the examples are mere exemplifications and do not limit the present invention. The present invention may be modified without departing from the scope of the invention.

In the following Examples, the "room temperature" means generally about 10° C. to about 35° C. As for "%", the yield is in mol/mol %, the solvent used for chromatography is in % by volume and other "%" is in % by weight. OH proton, NH proton etc. that could not be confirmed due to broad peak by proton NMR spectrum are not included in the data. The "pseudopentapeptide" means a pentapeptide containing a structure wherein the amino acid sequence represented by Phe-Gly-Leu-Arg-Trp (SEQ ID NO: 65) is altered at the amide bond between Gly-Leu.

Other abbreviations used in the specification mean the following.
Abbreviated Names and Japanese Names
Ac: acetyl
Boc: tert-butoxycarbonyl
Cha: cyclohexylalanine
Fmoc: 9-fluorenylmethoxycarbonyl
HONB: N-hydroxy-5-norbornene-2,3-dicarboxylmide
Nal(1): 1-naphthylalanine
Nal(2): 2-naphthylalanine
Phe(2Cl): 2-chlorophenylalanine
Phe(3Cl): 3-chlorophenylalanine
Phe(4Cl): 4-chlorophenylalanine
Phe(4NH$_2$): 4-aminophenylalanine
Pya(2): 2-pyridylalanine
Pya(3): 3-pyridylalanine
Pya(4): 4-pyridylalanine
Trp (For): N$^{in}$-formyltryptophan
TyrΨ(CH$_2$NH)Asn: means that —CONH-bond between Tyr and Asn is substituted by —CH$_2$NH-bond.
Me: methyl group
Mts: mesitylenesulfonyl group
t-Bu: tert-butyl group
Ph: phenyl group
THF: tetrahydrofuran
DBU: diazabicycloundecene
Et: ethyl group
i-Bu: isobutyl group
DMF: dimethylformamide
TMS: trimethylsilyl group
TFA: trifluoroacetic acid
Fmoc-OSu: N-(9-fluorenylmethyloxycarbonyloxy)succinimide
TES: triethylsilyl group
m-CPBA: metachloroperbenzoic acid
DIC: diisopropylcarbodiimide Abbreviations for bases, amino acids and the like used in the present specification and drawings are based on abbreviations specified by the IUPAC-IUB Commission on Biochemical Nomenclature or abbreviations in common use in relevant fields. Some examples are given below. When an enantiomer may be present in amino acid, it is of the L-configuration, unless otherwise stated.
Gly: Glycine
Ala: Alanine
Val: Valine
Leu: Leucine
Ile: Isoleucine
Ser: Serine
Thr: Threonine
Glu: Glutamic acid
Asp: Aspartic acid
Lys: Lysine
Arg: Arginine
His: Histidine
Phe: Phenylalanine
Tyr: Tyrosine
Trp: Tryptophan
Pro: Proline
Asn: Asparagine
Gln: Glutamine

EXAMPLES

The production methods of the compounds described in Examples are shown below.

Step 1: Synthesis of Dipeptide Structure (1)

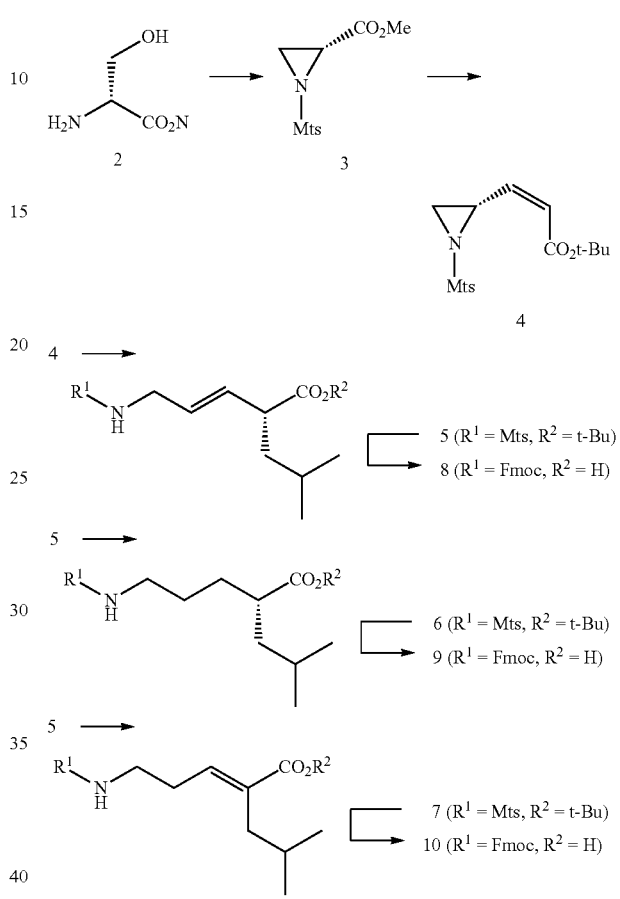

Production Example 1

Production of Compound 4 tert-butyl (4S,2Z)-4,5-[N-(2,4,6-trimethylphenylsulfonyl)epimino]-2-propenoate

Using compound 2, compound 3 was synthesized by the method described in Tetrahedron 2007, 63, 9243-9254. To a stirred solution of CH$_2$Cl$_2$ (28 mL) containing compound 3 (605 mg, 2.13 mmol) was added dropwise diisobutylaluminum hydride (0.99 M toluene solution (4.5 mL, 4.55 mmol) at −78° C. under argon. After 30 min, 0.5 N aqueous Rochelle salt solution was added with stirring at −78° C., and the mixture was extracted with Et$_2$O. The extract was washed with brine and dried over MgSO$_4$. An oily aldehyde resulting from concentration under reduced pressure was directly used for the next step without purification. To a stirred solution of THF (15 mL) containing (o-MePhO)$_2$P(O)CH$_2$CO$_2$t-Bu (882 mg, 2.34 mmol) were added NaI (383 mg, 2.56 mmol) and DBU (350 μl, 2.34 mmol) at 4° C. under argon. After stirring for 10 min, a solution of the above-mentioned aldehyde in THF (6 mL) was added dropwise to the mixture at −78° C., and the mixture was stirred at −78° C. for 1 hr. The mixture was warmed to −40° C., and stirred for 11 hr at said temperature. Water was added to quench the reaction, and the mixture was extracted with EtOAc. The extract was washed with saturated NH$_4$Cl and brine, and dried over MgSO$_4$. The residue was concentrated under reduced pressure and subjected to flash chromatography using silica gel and n-hexane-EtOAc (14:1) as an eluent to give compound 4 (600 mg, yield 80%) as a colorless oil.

$[\alpha]^{22}{}_D$−114.3 (c 1.85, CHCl$_3$); $^1$H NMR (400 MHz, CDCl$_3$) δ 1.49 (s, 9H), 2.20 (d, J=4.1 Hz, 1H), 2.29 (s, 3H), 2.69 (s, 6H), 2.93 (d, J=7.3 Hz, 1H), 4.52 (ddd, J=8.0, 7.3, 4.1 Hz, 1H), 5.58 (dd, J=11.7, 8.0 Hz, 1H), 5.83 (d, J=11.7 Hz, 1H), 6.95 (s, 2H); $^{13}$C NMR (100 MHz, CDCl$_3$) δ20.9, 22.9, 28.0, 33.3, 36.0, 81.1, 126.2, 131.7, 132.4, 140.1, 141.9, 143.0, 164.6. HRMS (FAB), m/z calcd for C$_{18}$H$_{26}$NO$_4$S (MH$^+$) 352.1583. found: 352.1585

Production Example 2

Production of Compound 5 tert-butyl (2R,3E)-2-isobutyl-5-[N-(2,4,6-trimethylphenylsulfonyl)amino]-3-pentenoate To a stirred solution of dry THF (2.4 mL) containing CuCN (108 mg, 1.20 mmol) and LiCl (102 mg, 2.40 mmol) at −78° C. was added THF (600 μL) containing i-BuMgCl (2.0 M) with a syringe. The mixture was heated to 4° C. and stirred for 30 min at 4° C. A dry THF (3 mL) solution containing compound 4 (105 mg, 0.300 mmol) was added dropwise to the above-mentioned reagent with stirring, and the mixture was stirred for 30 min. A mixture (1:1, 6 mL) of saturated NH$_4$Cl solution and 28% NH$_4$OH solution was added to quench the reaction at −78° C. After concentration of the solution, the residue was extracted with Et$_2$O and the extract was washed with brine and dried over MgSO$_4$. The solvent was evaporated under reduced pressure and the residue was purified by flash chromatography using silica gel and n-hexane-EtOAc (5:1) as an eluent to give compound 5 (110 mg, yield 90%) as a colorless solid.

mp 51-53° C.; $[\alpha]^{23}{}_D$ −22.0 (c 1.00, CHCl$_3$); $^1$H NMR (400 MHz, CDCl$_3$) δ 0.84 (d, J=6.3 Hz, 3H), 0.87 (d, J=6.3 Hz, 3H), 1.17-1.26 (m, 1H), 1.42 (s, 9H), 1.45-1.54 (m, 2H), 2.30 (s, 3H), 2.63 (s, 6H), 2.88 (ddd, J=8.5, 7.3, 7.3 Hz, 1H), 3.51 (dd, J=6.1, 6.1 Hz, 2H), 4.43 (t, J=6.1 Hz, 1H), 5.41 (dt, J=15.4, 6.1 Hz, 1H), 5.55 (dd, J=15.4, 8.5 Hz, 1H), 6.96 (s, 2H); $^{13}$C NMR (100 MHz, CDCl$_3$) δ20.9, 22.3, 22.4, 23.0, 25.6, 28.0, 41.4, 44.5, 47.7, 80.6, 126.7, 132.0, 132.7, 133.6, 139.0, 142.2, 173.3. Anal. Calcd for C$_{22}$H$_{35}$NO$_4$S: H, 8.61; C, 64.51; N, 3.42. Found: H, 8.33; C, 64.39; N, 3.48.

Production Example 3

Production of Compound 6 tert-butyl (S)-2-isobutyl-5-[N-(2,4,6-trimethylphenylsulfonyl)amino]pentanoate

To a stirred solution of MeOH (50 mL) containing compound 5 (2.05 g, 5.00 mmol) was added 5% Pd/C (50 mg) and the mixture was stirred for 14 hr under a hydrogen atmosphere at room temperature. The mixture was filtered through celite, and the filtrate was concentrated under reduced pressure. Recrystallization using n-hexane gave compound 6 (2.06 g, yield 100%) as a colorless solid.

mp 54-56° C.; $[\alpha]^{24}{}_D$ +0.9 (c 1.31, CHCl$_3$); $^1$H NMR (400 MHz, CDCl$_3$) δ 0.85 (d, J=6.3 Hz, 3H), 0.86 (d, J=6.3 Hz, 3H), 1.02-1.13 (m, 1H), 1.28-1.57 (m, 15H), 2.15-2.25 (m, 1H), 2.30 (s, 3H), 2.64 (s, 6H), 2.89 (ddt, J=6.6, 6.3, 3.9 Hz, 2H), 4.59 (dd, J=6.3, 6.3 Hz, 1H), 6.96 (s, 2H); $^{13}$C NMR (100 MHz, CDCl$_3$) δ 20.9, 21.9, 22.9, 23.1, 26.0, 27.4, 28.0, 29.9, 41.9, 42.4, 43.9, 80.2, 131.9, 133.6, 139.0, 142.1, 175.5. Anal. Calcd for C$_{22}$H$_{37}$NO$_4$S: H, 9.06; C, 64.20; N, 3.40. Found: H, 9.32; C, 64.02; N, 3.37.

Production Example 4

Production of Compound 7 tert-butyl (E)-2-isobutyl-5-[N-(2,4,6-trimethylphenylsulfonyl)amino]-2-pentenoate To a solution of DMF (25 mL) containing compound 5 (1.02 g, 2.50 mmol) was added DBU (1.87 mL, 12.5 mmol) and the mixture was stirred for 20 hr at room temperature. After concentration of the solution, the residue was extracted with Et$_2$O. The extract was washed with 1N HCl and brine and dried over MgSO$_4$. The solvent was evaporated under reduced pressure and the residue was purified by flash chromatography using silica gel and n-hexane-EtOAc(6:1) as an eluent to give compound 7 (960 mg, yield 94%) as a colorless solid.

mp 53-54° C.; $^1$H NMR (400 MHz, CDCl$_3$) δ 0.82 (d, J=6.8 Hz, 6H), 1.47 (s, 9H), 1.61-1.72 (m, 1H), 2.06 (d, J=7.3 Hz, 2H), 2.30 (s, 3H), 2.31 (dt, J=7.3, 7.3 Hz, 6H), 2.63 (s, 6H), 3.02 (dt, J=7.3, 6.3 Hz, 2H), 4.61 (t, J=6.3 Hz, 1H), 6.46 (t, J=7.3 Hz, 1H), 6.96 (s, 2H); $^{13}$C NMR (125 MHz, CDCl$_3$) δ 20.9, 22.4, 22.9, 28.0, 28.4, 29.0, 35.7, 41.7, 80.3, 132.0, 133.6, 136.2, 136.2, 139.1, 142.3, 166.9. Anal. Calcd for C$_{22}$H$_{34}$NO$_4$S: H, 8.61; C, 64.51; N, 3.42. Found: H, 8.60; C, 64.47; N, 3.27.

Production Example 5

Production of Compound 8

(2R,3E)-2-isobutyl-5-[N-(9-fluorenylmethoxycarbonyl)amino]-3-pentenoic acid

Compound 5 (819 mg, 2.00 mmol) was dissolved in 1M thioanisole-1M TMSBr-TFA (40 mL) at room temperature and the mixture was stirred at room temperature for 1 day. After concentration under reduced pressure, an oil residue was obtained and poured into ice-cooled dry diethyl ether. The resultant pellet was collected by centrifugation, washed with ice-cooled dry diethyl ether, and dissolved in water (10 mL). CH$_3$CN (10 mL) containing triethylamine (1.65 mL, 12.0 mmol) and Fmoc-OSu (670 mg, 2.00 mmol) was added continuously into the above-mentioned solution at 4° C. After stirring for 3 hr at room temperature, the mixture was extracted with EtOAc. The reaction was quenched with 1M HCl at 4° C. After concentration under reduced pressure, the resultant residue was extracted with EtOAc. The extract was washed with 1M HCl and brine and dried over MgSO$_4$. The residue was concentrated under reduced pressure, and subjected to flash chromatography using silica gel and n-hexane-EtOAc (2:1) containing 1% acetic acid as an eluent. The eluate was washed with brine and dried over MgSO$_4$, and concentrated to give compound 8 (400 mg, yield 51% in 2 steps) as a colorless solid.

mp 146-148° C.; $[\alpha]^{24}{}_D$ −30.8 (c 1.01, CHCl$_3$); $^1$H NMR (400 MHz, CDCl$_3$) δ 0.88 (d, J=6.3 Hz, 3H), 0.91 (d, J=6.3 Hz, 3H), 1.35-1.47 (m, 1H), 1.52-1.70 (m, 2H), 3.04-3.17 (m, 1H), 3.67-3.88 (m, 2H), 4.21 (t, J=6.6 Hz, 1H), 4.41 (d, J=6.6

Hz, 2H), 4.79-4.91 (m, 1H), 5.48-5.68 (m, 2H), 7.30 (dd, J=7.6, 7.3 Hz, 2H), 7.39 (dd, J=7.3, 7.3 Hz, 2H), 7.58 (d, J=7.3 Hz, 2H), 7.75 (d, J=7.6 Hz, 2H); $^{13}$C NMR (100 MHz, CDCl$_3$) δ 22.1, 22.5, 25.5, 41.1, 42.6, 46.7, 47.2, 66.7, 120.0, 125.0, 127.0, 127.7, 129.2, 130.0, 141.3, 143.9, 156.2, 179.7

Production Example 6

Production of Compound 9

(S)-2-isobutyl-5-[N-(9-fluorenylmethoxycarbonyl)amino]pentanoic acid

According to the method described for the synthesis of compound 8, compound 9 (362 mg, yield in 2 steps 46%) was obtained as a colorless solid from compound 6 (823 mg, 2.0 mmol).

mp 136-137° C.; [α]$^{24}_D$ +1.6 (c 1.09, CHCl$_3$); $^1$H NMR (400 MHz, CDCl$_3$) δ 0.89 (d, J=6.6 Hz, 3H), 0.91 (d, J=6.6 Hz, 3H), 1.20-1.31 (m, 1H), 1.38-1.67 (m, 6H), 2.38-2.50 (m, 1H), 3.20 (dt, J=7.6, 5.6 Hz, 1H), 4.20 (t, J=6.8 Hz, 1H), 4.39 (d, J=6.8 Hz, 2H), 4.84 (t, J=5.6 Hz, 1H), 7.30 (dd, J=7.6, 7.3 Hz, 2H), 7.39 (dd, J=7.6, 7.3 Hz, 2H), 7.58 (d, J=7.6 Hz, 2H), 7.76 (d, J=7.6 Hz, 2H); $^{13}$C NMR (100 MHz, CDCl$_3$) δ 22.1, 23.0, 26.1, 27.8, 29.7, 40.9, 41.5, 43.1, 47.2, 66.6, 120.0, 125.0, 127.0, 127.7, 141.3, 143.9, 156.5, 181.7. HRMS (FAB), m/z calcd for C$_{24}$H$_{30}$NO$_4$ (MH$^+$) 396.2169. found: 396.2180

Production Example 7

Production of Compound 10

(E)-2-isobutyl-5-[N-(9-fluorenylmethoxycarbonyl)amino]-2-pentenoic acid

According to the method described for the synthesis of compound 8, compound 10 (428 mg, yield in 2 steps 57%) was obtained as a colorless solid from compound 7 (778 mg, 1.90 mmol).

mp 162-163° C.; $^1$H NMR (500 MHz, DMSO-d6) δ0.81 (d, J=6.6 Hz, 6H), 1.60-1.75 (m, 1H), 2.10 (d, J=7.1 Hz, 2H), 2.30 (dt, J=7.3, 6.6 Hz, 2H), 3.07 (dt, J=6.6, 6.1 Hz, 2H), 4.19 (t, J=6.8 Hz, 1H), 4.28 (d, J=6.8 Hz, 2H), 6.67 (t, J=7.3 Hz, 1H), 7.31 (dd, J=7.6, 7.3 Hz, 2H), 7.37-7.43 (m, 3H), 7.66 (d, J=7.6 Hz, 2H), 7.87 (d, J=7.6 Hz, 2H), 12.10 (s, 1H); $^{13}$C NMR (125 MHz, DMSO-d6) δ22.2, 27.7, 28.8, 35.1, 39.4, 46.7, 65.2, 120.1, 125.1, 127.0, 127.5, 133.0, 139.2, 140.7, 143.9, 156.0, 168.7. HRMS (FAB), m/z calcd for C$_{24}$H$_{28}$NO$_4$ (MH$^+$) 394.2013. found: 394.2015

Step 2: Synthesis of Dipeptide Structure (2)

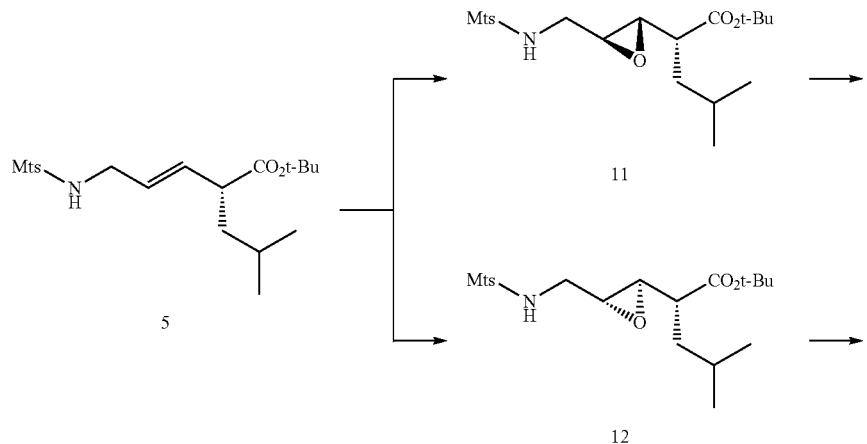

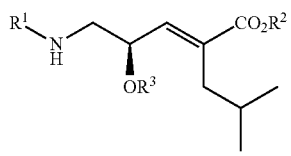

13 (R$^1$ = Mts, R$^2$ = t-Bu, R$^3$ = H)
15 (R$^1$ = Fmoc, R$^2$ = H, R$^3$ = H)
17 (R$^1$ = Fmoc, R$^2$ = H, R$^3$ = TES)

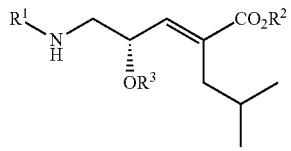

14 (R$^1$ = Mts, R$^2$ = t-Bu, R$^3$ = H)
16 (R$^1$ = Fmoc, R$^2$ = H, R$^3$ = H)
18 (R$^1$ = Fmoc, R$^2$ = H, R$^3$ = TES)

Production Example 8

Production of Compounds 11, 12 tert-butyl (2R,3S,4S)-3,4-epoxy-2-isobutyl-5-[N-(2,4,6-trimethylphenylsulfonyl)amino]pentanoate (compound 11)

tert-butyl (2R,3R,4R)-3,4-epoxy-2-isobutyl-5-[N-(2,4,6-trimethylphenylsulfonyl)amino]pentanoate (compound 12)

To a stirred solution of $CH_2Cl_2$ (1 mL) containing compound 5 (81.9 mg, 0.200 mmol) was added m-CPBA (51.8 mg, 0.300 mmol) at room temperature and the mixture was stirred for 20 hr at room temperature. The reaction was quenched with saturated sodium thiosulfate. After concentration under reduced pressure, the resultant residue was extracted with EtOAc. The extract was washed with water, 1M HCl aqueous solution, brine, 5% $NaHCO_3$ and brine and dried over $MgSO_4$. The residue was concentrated under reduced pressure, and subjected to flash chromatography using silica gel and n-hexane-EtOAc (8:1) as an eluent to give compound 11 (55.1 mg, yield 65%) and compound 12 (18.3 mg, yield 22%).

Compound 11: colorless solid; mp 109-111° C.; $[\alpha]^{24}_D$ -26.7 (c 1.23, $CHCl_3$); $^1H$ NMR (400 MHz, $CDCl_3$) δ 0.88 (d, J=6.3 Hz, 3H), 0.88 (d, J=6.3 Hz, 3H), 1.19-1.28 (m, 1H), 1.45 (s, 9H), 1.49-1.59 (m, 2H), 2.14 (ddd, J=8.3, 8.3, 6.6 Hz, 1H), 2.30 (s, 3H), 2.63 (s, 6H), 2.85-2.89 (m, 1H), 2.83-3.02 (m, 2H), 3.26 (ddd, J=13.9, 6.6, 3.4 Hz, 1H), 4.67 (dd, J=6.6, 6.6 Hz, 1H), 6.96 (s, 2H); $^{13}C$ NMR (100 MHz, $CDCl_3$) δ 20.9, 22.1, 22.8, 22.9, 25.9, 28.0, 38.0, 43.4, 46.8, 55.6, 57.6, 81.2, 132.1, 133.5, 139.0, 142.4, 172.5. Anal. Calcd for $C_{22}H_{35}NO_5S$: C, 62.09; H, 8.29; N, 3.29. Found: C, 62.07; H, 8.11; N, 3.28.

Compound 12: colorless solid; mp 78-80° C.; $[\alpha]^{24}_D$ +13.4 (c 1.00, $CHCl_3$); $^1H$ NMR (400 MHz, $CDCl_3$) δ 0.89 (d, J=6.1 Hz, 6H), 1.40-1.46 (m, 10H), 1.58-1.71 (m, 2H), 2.17 (ddd, J=7.8, 7.8, 6.1 Hz, 1H), 2.30 (s, 3H), 2.63 (s, 6H), 2.85 (dd, J=7.8, 1.5 Hz, 1H), 2.92-3.01 (m, 2H), 3.16-3.25 (m, 1H), 4.77-4.85 (m, 1H), 6.96 (s, 2H); $^{13}C$ NMR (100 MHz, $CDCl_3$) δ 20.9, 22.1, 22.7, 22.9, 25.9, 28.0, 39.0, 43.5, 46.7, 55.0, 57.6, 81.2, 132.0, 133.3, 139.0, 142.3, 171.9. Anal. Calcd for $C_{22}H_{35}NO_5S$: C, 62.09; H, 8.29; N, 3.29. Found: C, 61.90; H, 8.04; N, 3.26.

Production Example 9

Production of Compound 13 tert-butyl (4R,2E)-4-hydroxy-2-isobutyl-5-[N-(2,4,6-trimethylphenylsulfonyl)amino]-2-pentenoate To NaH (60%, 752 mg, 18.8 mmol) was added dry THF solution (47 mL) containing compound 11 (2.00 g, 4.70 mmol) at 4° C. The mixture was warmed to room temperature and stirred for 2 hr at room temperature. The reaction was quenched with saturated $NH_4Cl$ at 4° C. After concentration under reduced pressure, the residue was extracted with EtOA. The extract was washed with brine and dried over $MgSO_4$, concentrated under reduced pressure and subjected to flash chromatography using silica gel and n-hexane-EtOAc (2:1) as an eluent to give compound 13 (1.95 g, yield 98%) as a colorless solid.

mp 74-76° C.; $[\alpha]^{25}_D$ -35.8 (c 1.02, $CHCl_3$); $^1H$ NMR (400 MHz, $CDCl_3$) δ 0.81 (d, J=6.6 Hz, 3H), 0.83 (d, J=6.6 Hz, 3H), 1.46 (s, 9H), 1.60-1.71 (m, 1H), 2.02 (dd, J=13.4, 7.6 Hz, 1H), 2.12 (dd, J=13.4, 6.9 Hz, 1H), 2.28-2.35 (m, 4H), 2.65 (s, 6H), 2.86 (ddd, J=13.4, 9.0, 4.4 Hz, 1H), 3.03 (ddd, J=13.4, 8.3, 3.2 Hz, 1H), 4.42 (dddd, J=9.0, 9.0, 3.7, 3.2 Hz, 1H), 5.19 (dd, J=8.3, 4.4 Hz, 1H), 6.38 (d, J=9.0 Hz, 1H), 6.97 (s, 2H); $^{13}C$ NMR (100 MHz, $CDCl_3$) δ 20.9, 22.0, 22.5, 22.8, 27.9, 28.2, 35.9, 47.3, 67.2, 81.0, 132.1, 133.4, 136.6, 137.4, 139.0, 142.4, 166.7. Anal. Calcd for $C_{22}H_{35}NO_5S$: C, 62.09; H, 8.29; N, 3.29. Found: C, 61.90; H, 8.04; N, 3.34.

Production Example 10

Production of Compound 14 tert-butyl (4S,2E)-4-hydroxy-2-isobutyl-5-[N-(2,4,6-trimethylphenylsulfonyl)amino]-2-pentenoate To a stirred solution of $CH_3OH$ (23 mL) containing compound 12 (979 mg, 2.30 mmol) was added $K_2CO_3$ (1.27 g, 9.20 mmol) at room temperature. The mixture was heated to 50° C., and stirred for 5.5 hr at said temperature. After concentration under reduced pressure, the residue was extracted with EtOAc. The extract was washed with 1N HCl and brine and dried over $MgSO_4$. After concentration under reduced pressure, the residue was subjected to flash chromatography using silica gel and n-hexane-EtOAc (2:1) as an eluent to give compound 14 (733 mg, yield 75%) as a colorless solid.

mp 72-73° C.; $[\alpha]^{20}_D$ +39.1 (c 1.31, $CHCl_3$); $^1H$ NMR (400 MHz, $CDCl_3$) δ 0.81 (d, J=5.6 Hz, 3H), 0.83 (d, J=5.6 Hz, 3H), 1.46 (s, 9H), 1.60-1.73 (m, 1H), 2.03 (dd, J=13.2, 7.6 Hz, 1H), 2.12 (dd, J=13.2, 6.8 Hz, 1H), 2.28 (d, J=3.9 Hz, 1H), 2.30 (s, 3H), 2.65 (s, 6H), 2.87 (ddd, J=13.4, 9.0, 4.4 Hz, 1H), 3.03 (ddd, J=13.4, 8.3, 3.4 Hz, 1H), 4.43 (dddd, J=9.0, 9.0, 3.9, 3.4 Hz, 1H), 5.17 (dd, J=8.3, 4.4 Hz, 1H), 6.38 (d, J=9.0 Hz, 1H), 6.97 (s, 2H); $^{13}C$ NMR (125 MHz, $CDCl_3$) δ 20.9, 22.1, 22.5, 22.8, 28.0, 28.2, 36.0, 47.4, 67.3, 81.0, 132.1, 133.6, 136.7, 137.4, 139.1, 142.4, 166.7. Anal. Calcd for $C_{22}H_{35}NO_5S$: C, 62.09; H, 8.29; N, 3.29. Found: C, 61.97; H, 8.13; N, 3.16.

Production Example 11

Production of Compound 15

(4R,2E)-5-[N-(9-fluorenylmethoxycarbonyl)amino]-4-hydroxy-2-isobutyl-2-pentenoic acid According to the method described for the synthesis of compound 8, compound 15 (1.02 mg, yield in 2 steps 91%) was obtained as a colorless semisolid from compound 13 (1.16 mg, 2.73 mmol).

$[\alpha]^{20}_D$ -1.25 (c 1.03, $CHCl_3$); $^1H$ NMR (400 MHz, $CDCl_3$) δ 0.91 (d, J=6.6 Hz, 6H), 1.75-1.87 (m, 1H), 2.20-2.29 (m, 2H), 3.15-3.26 (m, 1H), 3.36-3.46 (m, 1H), 4.21 (t, J=6.83 Hz, 1H), 4.44 (d, J=6.8 Hz, 2H), 4.54-4.62 (m, 1H), 5.26 (dd, J=5.9, 5.9 Hz, 1H), 6.76 (d, J=9.0 Hz, 1H), 7.31 (dd, J=7.6, 7.3 Hz, 2H), 7.40 (dd, J=7.3, 7.3 Hz, 2H), 7.59 (d, J=7.3 Hz, 2H), 7.76 (d, J=7.6 Hz, 2H); $^{13}C$ NMR (100 MHz, $CDCl_3$) δ 22.2, 22.5, 28.1, 35.8, 46.2, 47.2, 67.0, 68.0, 120.0, 125.0, 127.1, 127.7, 133.9, 141.3, 141.6, 143.8, 157.2, 172.2. HRMS (FAB), m/z calcd for $C_{24}H_{28}NO_5$ ($MH^+$) 410.1962. found: 410.1964

Production Example 12

Production of Compound 16

(4S,2E)-5-[N-(9-fluorenylmethoxycarbonyl)amino]-4-hydroxy-2-isobutyl-2-pentenoic acid According to the method described for the synthesis of compound 8, compound 16 (1.40 mg, yield 88% in 2 steps) was obtained as a colorless semisolid from compound 14 (1.70 mg, 4.00 mmol).

$[\alpha]^{21}_D$+1.5 (c 1.27, CHCl$_3$); $^1$H NMR (400 MHz, CDCl$_3$) δ 0.91 (d, J=6.6 Hz, 6H), 1.75-1.87 (m, 1H), 2.20-2.29 (m, 2H), 3.15-3.26 (m, 1H), 3.36-3.46 (m, 1H), 4.21 (t, J=6.83 Hz, 1H), 4.44 (d, J=6.8 Hz, 2H), 4.54-4.62 (m, 1H), 5.26 (dd, J=5.9, 5.9 Hz, 1H), 6.76 (d, J=9.0 Hz, 1H), 7.31 (dd, J=7.6, 7.3 Hz, 2H), 7.40 (dd, J=7.3, 7.3 Hz, 2H), 7.59 (d, J=7.3 Hz, 2H), 7.76 (d, J=7.6 Hz, 2H); $^{13}$C NMR (100 MHz, CDCl$_3$) δ 22.2, 22.5, 28.1, 35.8, 46.2, 47.2, 67.0, 68.0, 120.0, 125.0, 127.1, 127.7, 133.9, 141.3, 141.6, 143.8, 157.2, 172.2. HRMS (FAB), m/z calcd for C$_{24}$H$_{28}$NO$_5$ (MH$^+$) 410.1962. found: 410.1972

Production Example 13

Production of Compound 17

(4R,2E)-5-[N-(9-fluorenylmethoxycarbonyl)amino]-2-isobutyl-4-triethylsiloxy-2-pentenoic acid To a stirred solution of CH$_2$Cl$_2$ (400 µL) containing compound 15 (81.9 mg, 0.200 mmol) and imidazole (68.1 mg, 1.00 mmol) was added chlorotriethylsilane (67.0 µL, 0.400 mmol) at 4° C. The mixture was stirred for 4 hr at 4° C. After concentration under reduced pressure, the residue was extracted with Et$_2$O. The extract was washed with 1N HCl and brine and dried over MgSO$_4$. After concentration under reduced pressure, the extract was subjected to flash chromatography using silica gel and n-hexane-EtOAc (4:1) containing 1% AcOH as an eluent to give compound 17 (57.1 mg, yield 55%) as a colorless oil.

$[\alpha]^{23}_D$-3.5 (c 2.86, CHCl$_3$); $^1$H NMR (400 MHz, CDCl$_3$) δ 0.57 (q, J=7.8 Hz, 6H), 0.88-1.00 (m, 15H), 1.80-1.95 (m, 1H), 2.17 (dd, J=13.2, 7.0 Hz, 1H), 2.29 (dd, J=13.2, 7.0 Hz, 1H), 3.04-3.20 (m, 1H), 3.30-3.48 (m, 1H), 4.22 (t, J=6.8 Hz, 1H), 4.39 (dd, J=6.8, 6.8 Hz, 2H), 4.53-4.64 (m, 1H), 5.08-5.22 (m, 1H), 6.75 (d, J=8.5 Hz, 1H), 7.30 (dd, J=7.6, 7.6 Hz, 2H), 7.39 (dd, J=7.6, 7.6 Hz, 2H), 7.55-7.63 (m, 2H), 7.75 (d, J=7.6 Hz, 2H); $^{13}$C NMR (100 MHz, CDCl$_3$) δ 4.8, 6.7, 22.5, 22.5, 28.0, 36.0, 46.4, 47.2, 66.9, 68.4, 119.9, 125.0, 125.1, 127.0, 127.7, 132.3, 141.3, 143.8, 156.4, 172.8. HRMS (FAB), m/z calcd for C$_{30}$H$_{42}$NO$_5$Si (MH$^+$) 524.2827. found: 524.2824

Production Example 14

Production of Compound 18

(4S,2E)-5-[N-(9-fluorenylmethoxycarbonyl)amino]-2-isobutyl-4-triethylsiloxy-2-pentenoic acid According to the method described for the synthesis of compound 17, compound 18 (1.70 mg, yield 95% in 2 steps) was obtained as a colorless semisolid from compound 16 (1.39 mg, 3.40 mmol).

$[\alpha]^{23}_D$+3.5 (c 1.20, CHCl$_3$); $^1$H NMR (400 MHz, CDCl$_3$) δ 0.59 (q, J=7.8 Hz, 6H), 0.86-0.98 (m, 15H), 1.79-1.94 (m, 1H), 2.19 (dd, J=13.4, 7.3 Hz, 1H), 2.29 (dd, J=13.4, 7.3 Hz, 1H), 3.07-3.25 (m, 1H), 3.29-3.46 (m, 1H), 4.22 (t, J=6.8 Hz, 1H), 4.39 (d, J=6.8 Hz, 2H), 4.53-4.64 (m, 1H), 4.98-5.20 (m, 1H), 6.74 (d, J=8.5 Hz, 1H), 7.29 (dd, J=7.6, 7.6 Hz, 2H), 7.38 (dd, J=7.6, 7.6 Hz, 2H), 7.58 (d, J=7.6 Hz, 1H), 7.77 (d, J=7.6 Hz, 2H); $^{13}$C NMR (100 MHz, CDCl$_3$) δ 4.8, 6.7, 22.5, 22.5, 28.0, 36.0, 46.5, 47.2, 66.9, 68.4, 119.9, 125.0, 125.1, 127.0, 127.7, 132.3, 141.3, 143.8, 156.4, 172.7. HRMS (FAB), m/z calcd for C$_{30}$H$_{42}$NO$_5$Si (MH$^+$) 524.2827. found: 524.2826

Step 3: General Synthesis Method of Pseudopentapeptide by Fmoc Solid Phase Synthesis Process A protected peptide chain was constructed on a Rink-amino resin (0.60 mmol/g, 170 mg, 0.1 mmol). Fmoc-protected α-amino acid (0.3 mmol) or 4-fluorobenzoic acid (42 mg, 0.3 mmol) was coupled using N,N'-diisopropylcarbodiimide (DIC; 46 µL, 0.3 mmol) and N-hydroxybenzotriazole monohydrate (HOBt.H$_2$O; 46 mg, 0.3 mmol) in DMF. A pseudopeptide partial structure was formed using DIC and N-hydroxy-7-azabenzotriazole monohydrate (HOAt; 41 mg, 0.3 mmol). The completion of each coupling reaction was confirmed using a Kaiser test. Fmoc protecting group was removed by treating the resin with a DMF/piperidine solution (80/20, v/v). The obtained resin was treated with 1M TMSBr-thioanisole/TFA, m-cresol and 1,2-ethanoldithiol. The resin was removed by filtration, and the filtrate was poured into ice-cooled dry diethyl ether. The resultant powder was collected by centrifugation, and washed 3 times with ice-cooled dry diethyl ether. The crude product was purified by preparative HPLC to give a desired pseudopeptide as a colorless powder. The purity of each compound was measured prior to a biological test by analytic RP-HPLC using two different solvent systems.

Production Example 15

Production of Compound 19

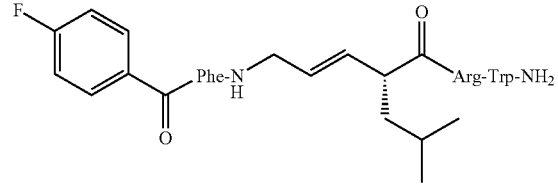

Compound 8 (120 mg, 0.3 mmol) was subjected to the solid phase synthesis process utilizing Fmoc in the above-mentioned step 3. Compound 19 was obtained as TFA salt (33 mg, yield 36% from Rink-amide resin).

$[\alpha]^{23}_D$-17.5 (c 0.22, CH$_3$OH); HRMS (FAB), m/z calcd for C$_{42}$H$_{53}$N$_9$O$_5$F (M+H$^+$) 782.4148. found: 782.4163

Production Example 16

Production of Compound 20

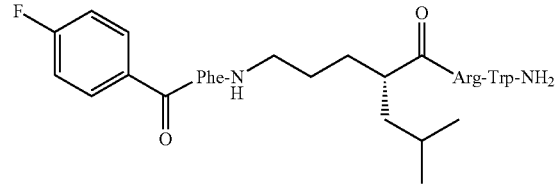

Compound 9 (120 mg, 0.3 mmol) was subjected to the solid phase synthesis process utilizing Fmoc in the above-mentioned step 3. Compound 20 was obtained as TFA salt (42 mg, yield 47% from Rink-amide resin).

$[\alpha]^{23}_D$ −14.3 (c 0.12, $CH_3OH$); HRMS (FAB), m/z calcd for $C_{42}H_{55}N_9O_5F$ ($M+H^+$) 782.4303. found: 784.4296

Production Example 17

Production of Compound 21

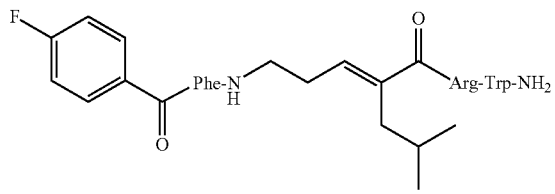

Compound 10 (120 mg, 0.3 mmol) was subjected to the solid phase synthesis process utilizing Fmoc in the above-mentioned step 3. Compound 21 was obtained as TFA salt (48 mg, yield 54% from Rink-amide resin).

$[\alpha]^{25}_D$ +5.0 (c 0.23, $CH_3OH$); HRMS (FAB), m/z calcd for $C_{42}H_{53}N_9O_5F$ ($M+H^+$) 782.4148. found: 782.4142

Production Example 18

Production of Compound 22

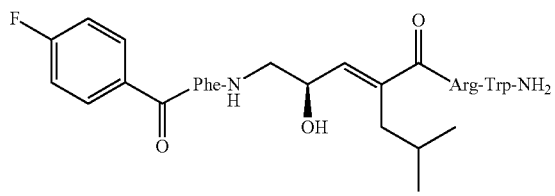

Compound 17 (160 mg, 0.3 mmol) was subjected to the solid phase synthesis process utilizing Fmoc in the above-mentioned step 3. Compound 22 was obtained as TFA salt (51 mg, yield 56% from Rink-amide resin).

$[\alpha]^{27}_D$ +1.9 (c 0.12, $CH_3OH$); HRMS (FAB), m/z calcd for $C_{42}H_{53}N_9O_5F$ ($M+H^+$) 798.4097. found: 798.4092

Production Example 19

Production of Compound 23

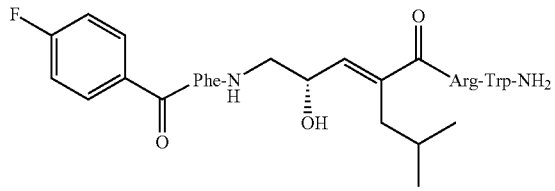

Compound 18 (160 mg, 0.3 mmol) was subjected to the solid phase synthesis process utilizing Fmoc in the above-mentioned step 3. Compound 23 was obtained as TFA salt (48 mg, yield 53% from Rink-amide resin).

$[\alpha]^{21}_D$ −22.3 (c 0.15, $CH_3OH$); HRMS (FAB), m/z calcd for $C_{42}H_{53}N_9O_6F$ ($M+H^+$) 798.4097. found: 798.4109

Step 4: Synthesis of Pentapeptide Containing Hydroxyethylene-Type Dipeptide

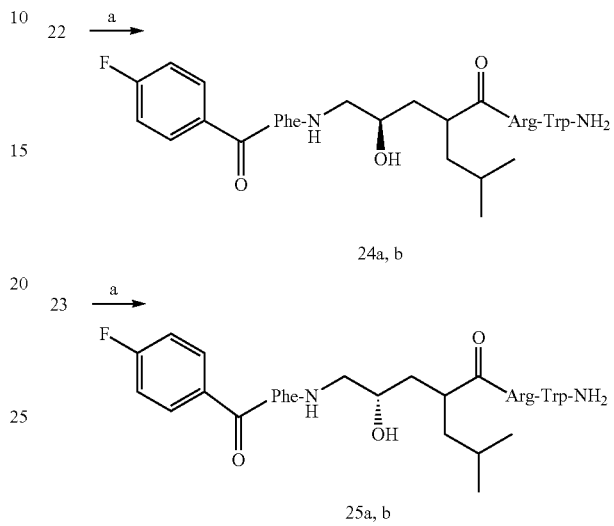

Synthesis Method of Pseudopentapeptide Containing Hydroxyethylene Dipeptide

To a solution of $CH_3OH$ (2 mL) containing compound 22 or 23 (18 mg, 0.020 mmol) was added $Pd(OAc)_2$ (4.5 mg, 0.020 mmol) and the mixture was stirred overnight under $H_2$ at room temperature. The mixture was filtered through celite, and the filtrate was concentrated under reduced pressure. The crude product was purified by preparative HPLC to give a desired pseudopeptide containing hydroxyethylene-type dipeptide as a colorless powder. The purity of each compound was measured prior to a biological test by analytic RP-HPLC using two different solvent systems.

Production Example 20

Production of Compounds 24a and 24b

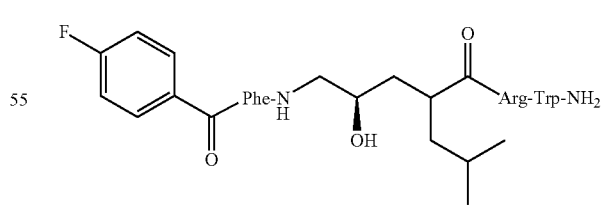

Pseudopentapeptide 22 containing allyl alcohol was converted to give reduced pseudopentapeptides 24a (5.2 mg, yield 29%) and 24b (7.8 mg, yield 43%) as TFA salts.

Compound 24a; $[\alpha]^{25}_D$ −7.2 (c 0.10, $CH_3OH$); HRMS (FAB), m/z calcd for $C_{42}H_{55}N_9O_6F$ ($M+H^+$) 800.4254. found: 800.4263.

Compound 24b; $[\alpha]^{25}_D$ −3.8 (c 0.11, CH$_3$OH); HRMS (FAB), m/z calcd for C$_{42}$H$_{55}$N$_9$O$_6$F (M+H$^+$) 800.4254. found: 800.4257

Production Example 21

Production of Compounds 25a and 25b

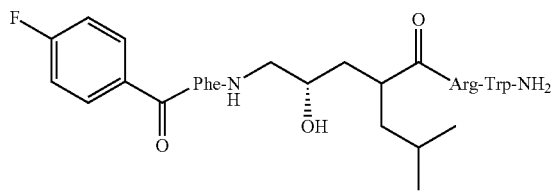

Compound 23 was converted to give compounds 25a (5.4 mg, yield 30%) and 25b (2.9 mg, yield 16%) as TFA salts.

compound 25a; $[\alpha]^{22}_D$ +3.6 (c 0.08, CH$_3$OH); HRMS (FAB), m/z calcd for C$_{42}$H$_{55}$N$_9$O$_6$F (M+H$^+$) 800.4254. found: 782.800.4271.

compound 25b; $[\alpha]^{23}_D$ +10.7 (c 0.11, CH$_3$OH); HRMS (FAB), m/z calcd for C$_{42}$H$_{55}$N$_9$O$_6$F (M+H$^+$) 800.4254. found: 800.4250

Reference Production Example 1

Production of Compound 1

SEQ ID NO: 66

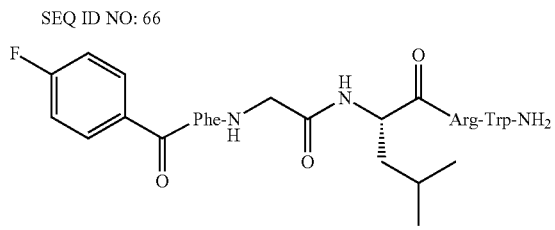

Compound 1 was produced according to the method of Production Example 20 of WO 2007/125619.

Reference Production Example 2

Production of Compound 26

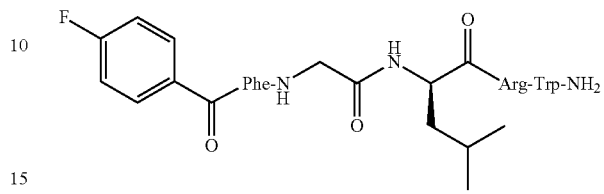

Instead of dipeptide, Fmoc-D-Leu-OH (110 mg, 0.3 mmol) and Fmoc-Gly-OH (89 mg, 0.3 mmol) were subjected to the solid phase synthesis process utilizing Fmoc. Compound 26 was obtained as a TFA salt (48 mg, yield 52% from Rink-amide resin).

$[\alpha]^{20}_D$ −4.5 (c 0.22, CH$_3$OH); HRMS (FAB), m/z calcd for C$_{41}$H$_{52}$N$_{10}$O$_6$F (M+H$^+$) 798.4052. found: 799.4067

The pseudopentapeptides (compounds 19-25b) synthesized in Production Examples 15-21 and the pentapeptides (compounds 1 and 26) synthesized in Reference Production Examples 1 and 2 were measured for the following 6 items.

The GPR54 agonist activity of the obtained compounds was evaluated by Flipr assay measuring increase in the intracellular Ca$^{2+}$ ion concentration caused by stimulation of receptor as a signal. The activity value was calculated as a signal value (% Activity) obtained upon addition of 10 nM compound, based on the signal upon addition of 1 μM kisspeptin-10 as 100%. Moreover, the concentration of a compound showing 50% agonist activity was taken as EC$_{50}$. As Q$_{EC}$, moreover, the EC$_{50}$ value of each compound was divided by the EC$_{50}$ value of kisspeptin-10.

A binding inhibitory test using membrane fraction of human GPR54-expressing cell and [$^{125}$I]-Metastin 40-54 was performed, and IC$_{50}$ value was calculated (see non-patent document 2). The IC$_{50}$ value was defined by the concentration of the compound necessary for suppressing the signal of the labeled ligand by 50%. As Q$_{ic}$, moreover, the IC$_{50}$ value of each compound was divided by the IC$_{50}$ value of kisspeptin-10.

In addition, the half-life (t$_{1/2}$) of the compound in the serum was measured.

TABLE 1-1

| Compound | X | % Activity | IC$_{50}$ (nM) | Q$_{IC}$ | EC$_{50}$ (nM) | Q$_{EC}$ | t$_{1/2}$ (h) |
|---|---|---|---|---|---|---|---|
| 1 | | 94.7 | 0.71 | 7.3 | 0.45 | 1.8 | 6.6 |
| 19 | | 97.6 | 0.12 | 1.0 | 0.30 | 1.2 | 38 |

TABLE 1-2

| # | Structure | | | | | | |
|---|---|---|---|---|---|---|---|
| 20 | (structure) | 70.3 | 1.2 | 10 | 2.5 | 10 | 45 |
| 21 | (structure) | 49.3 | 4.6 | 47 | 5.4 | 22 | 52 |
| 22 | (structure) | 18.7 | 32 | 270 | NT | — | 60 |
| 23 | (structure) | 0.7 | 460 | 4800 | NT | — | 1100 |
| 24a | (structure) | 0.6 | 380 | 3200 | NT | — | 470 |
| 24b | (structure) | 53.9 | 5.7 | 48 | 4.3 | 18 | 54 |
| 25a | (structure) | 13.8 | 32 | 330 | NT | — | 120 |
| 25b | (structure) | 95.6 | 0.24 | 2.5 | 0.36 | 1.5 | 35 |

TABLE 1-2-continued

| | | | | | | |
|---|---|---|---|---|---|---|
| 26 | [structure] | 240 | 3500 | NT | — | NT |
| Kisspeptin-10 | | 0.070-0.12 | 1 | 0.24 | 1 | NT |

Furthermore, the resistance of the present invention to the decomposition by matrix protease (MMP) was examined. For example, compounds 19 and 25b were treated with MMP2. They were retained even after 48 hr with scarce decomposition. However, only about 65% of kisspeptin-10 was retained. For example, compounds 19, 23, 25b and the like were treated with MMP9. As a result, they were retained even after 72 hr with scarce decomposition. However, only about 50% of compound 1 was retained.

Therefore, it has been clarified that the compound of the present invention has an activity comparable to that of compound 1 already known as a GPR54 agonist, has a longer blood half-life (resists decomposition in the serum) as compared to compound 1, and is not easily decomposed by MMP.

INDUSTRIAL APPLICABILITY

According to the present invention, a compound having a superior GPR54 agonist activity can be provided. The compound of the present invention specifically binds to and activate GPR54, which is a 7-transmembrane receptor, and enhances the action of metastin (aka kisspeptin), which is an endogenous ligand thereof. The compound of the present invention shows a strikingly enhanced GPR54 agonist activity as compared to native type metastin. In addition, since the compound of the present invention is modified to resist decomposition by peptidase in the body, it can efficiently act as a GPR54 agonist.

A pharmaceutical composition containing the compound of the present invention can be effectively used as a cancer metastasis suppressant, or an agent for the prophylaxis or treatment of infertility or abnormal control of secretion of sex hormone and gonadotropic hormone, based on the GPR54 receptor agonist action.

Since metastin has been clarified to act suppressively on CXCR4-chemokine receptor (CXCR4) closely related to cancer metastasis or growth, rheumatoid arthritis, lung fibrosis or HIV infection, the pharmaceutical composition of the present invention is also expected to be effective as an agent for the prophylaxis or treatment of these diseases. Moreover, the pharmaceutical composition of the present invention can also be utilized instead of CXCR4 antagonists and CXCR4 monoclonal antibodies feared to cause side effects.

This application is based on patent application No. 2008-119235 filed in Japan (filing date: Apr. 30, 2008), the contents of which are incorporated in full herein.

---

The invention claimed is:

1. A metastin derivative (I) represented by the formula (I)

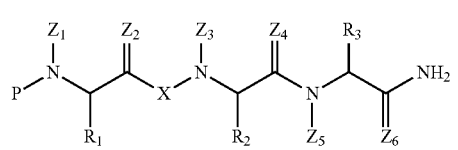

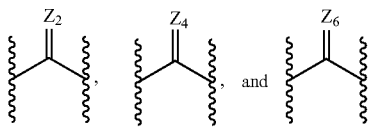

wherein $Z_1$, $Z_3$ and $Z_5$ are the same or different and each is a hydrogen atom or $C_{1-3}$ alkyl, are the same or different and each is —CH$_2$—, —CO— or —CS—, $R_1$ is $C_{1-4}$ alkyl optionally substituted by substituent(s) selected from the group consisting of (1) an optionally substituted $C_{6-12}$ aromatic hydrocarbon group, (2) an optionally substituted 5- to 14-membered aromatic heterocyclic group consisting of 1 to 7 carbon atoms and a hetero atom selected from the group consisting of a nitrogen atom, an oxygen atom and a sulfur atom, (3) an optionally substituted $C_{8-14}$ aromatic fused ring group, (4) an optionally substituted 5- to 14-membered aromatic fused heterocyclic group consisting of 3 to 11 carbon atoms and a hetero atom selected from the group consisting of a nitrogen atom, an oxygen atom and a sulfur atom, (5) an optionally substituted nonaromatic cyclic hydrocarbon group having a carbon number of not more than 7, and (6) an optionally substituted nonaromatic heterocyclic group having a carbon number of not more than 7, $R_2$ is (1) $C_{1-8}$ alkyl having an optionally substituted basic group, and optionally further having other substituent(s), (2) aralkyl having an optionally substituted basic group, and optionally further having other substituent(s), (3) $C_{1-4}$ alkyl having a nonaromatic cyclic hydrocarbon group having an optionally substituted basic group and a carbon number of not more than 7, and optionally further having other substituent(s), or (4) $C_{1-4}$ alkyl having a nonaromatic heterocyclic group having an optionally substituted basic group and a carbon number of not more than 7, and optionally further having other substituent(s), $R_3$ is $C_{1-4}$ alkyl optionally substituted by substituent(s) selected from the group consisting of (1) an optionally substituted $C_{6-12}$ aromatic hydrocarbon group, (2) an optionally substituted 5- to 14-membered aromatic heterocyclic group consisting of 1 to 7 carbon atoms and a hetero atom selected from the group consisting of a nitrogen atom, an oxygen atom and a sulfur atom, (3) an optionally substituted $C_{8-14}$ aromatic fused ring group, (4) an optionally substituted 5- to 14-membered aromatic fused heterocyclic group consisting of 3 to 11 carbon atoms and a hetero atom selected from the group consisting of a nitrogen atom, an oxygen atom and a sulfur atom, (5) an optionally substituted nonaromatic cyclic hydrocarbon group having a carbon number of not more than 7, and (6) an optionally substituted nonaromatic heterocyclic group having a carbon number of not more than 7, X is a group selected from the group consisting of (IV)

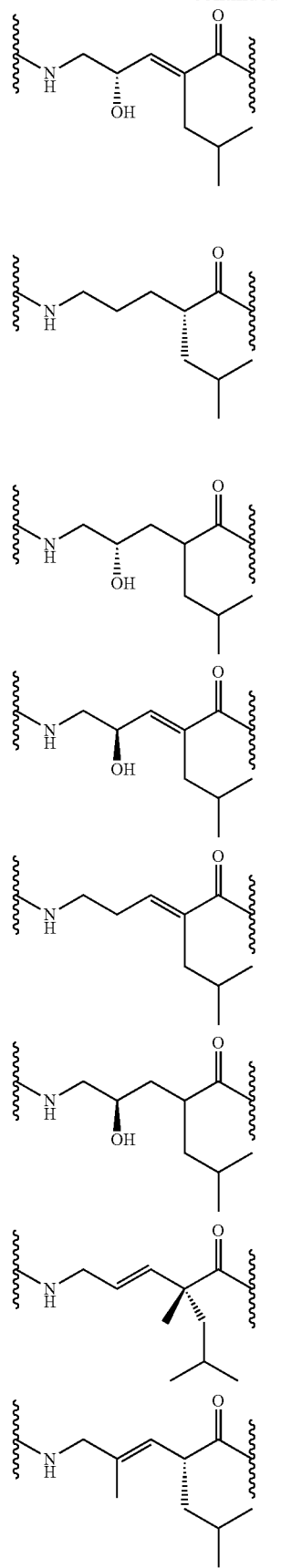

and

-continued (group (IV)),

P is (1) a hydrogen atom,
(2) any amino acid residues bound to each other contiguously or non-contiguously from the C-terminal side of the 1st-49th amino acid sequence of the amino acid sequence shown by SEQ ID NO: 67,
(3) a group represented by the formula $J^1\text{-}J^2\text{-}C(J^3)(Q^3)Y^1C(J^4)(Q^4)Y^2C(J^5)(Q^5)Y^3C(J^6)(Q^6)C(=Z^{10})-$ wherein $J^1$ is (a) a hydrogen atom or (b) (i) $C_{1-15}$ acyl, (ii) $C_{1-15}$ alkyl, (iii) $C_{6-14}$ aryl, (iv) carbamoyl, (v) carboxyl, (vi) sulfino, (vii) amidino or (viii) glyoxyloyl, each of which is optionally substituted by substituent(s) containing a ring group optionally having substituent(s),
$J^2$ is (i) NH optionally substituted by $C_{1-6}$ alkyl, (ii) $CH_2$ optionally substituted by $C_{1-6}$ alkyl, (iii) O or (iv) S,
$J^3$-$J^6$ are each a hydrogen atom or $C_{1-3}$ alkyl,
$Q^3$-$Q^6$ are each $C_{1-4}$ alkyl optionally having substituent(s) selected from the group consisting of
(i) an optionally substituted $C_{6-12}$ aromatic hydrocarbon group,
(ii) an optionally substituted 5- to 14-membered aromatic heterocyclic group consisting of 1 to 7 carbon atoms and a hetero atom selected from the group consisting of a nitrogen atom, an oxygen atom and a sulfur atom,
(iii) an optionally substituted $C_{8-14}$ aromatic fused ring group,
(iv) an optionally substituted 5- to 14-membered aromatic fused heterocyclic group consisting of 3 to 11 carbon atoms and a hetero atom selected from the group consisting of a nitrogen atom, an oxygen atom and a sulfur atom,
(v) an optionally substituted nonaromatic cyclic hydrocarbon group having a carbon number of not more than 7,
(vi) an optionally substituted nonaromatic heterocyclic group having a carbon number of not more than 7,
(vii) optionally substituted amino,
(viii) optionally substituted guanidino,
(ix) optionally substituted hydroxy,
(x) optionally substituted carboxyl,
(xi) optionally substituted carbamoyl, and
(xii) optionally substituted sulfhydryl
or a hydrogen atom,
$J^3$ and $Q^3$, $J^4$ and $Q^4$, $J^5$ and $Q^5$, or $J^6$ and $Q^6$ may be bonded, or $J^2$ and $Q^3$, $Y^1$ and $Q^4$, $Y^2$ and $Q^5$, or $Y^3$ and $Q^6$ may be bonded to form a ring,
$Y^1$-$Y^3$ are each a group represented by $-CON(J^{13})-$, $-CSN(J^{13})-$, $-C(J^{14})N(J^{13})-$ or $-N(J^{13})CO-$ ($J^{13}$ and $J^{14}$ are each a hydrogen atom or $C_{1-3}$ alkyl),
$Z^{10}$ is a hydrogen atom, O or S,
(4) a group represented by the formula $J^1\text{-}J^2\text{-}C(J^7)(Q^7)Y^2C(J^8)(Q^8)Y^3C(J^9)(Q^9)C(=Z^{10})-$ wherein $J^1$ and $J^2$ are each as defined above,
$J^7$-$J^9$ are as defined for $J^3$,
$Q^7$-$Q^9$ are as defined for $Q^3$,
$Y^2$ and $Y^3$ are as defined above,
$Z^{10}$ is as defined above,
$J^7$ and $Q^7$, $J^8$ and $Q^8$, or $J^9$ and $Q^9$ may be bonded, or $J^2$ and $Q^7$, $Y^2$ and $Q^8$, or $Y^3$ and $Q^9$ may be bonded to form a ring,
(5) a group represented by the formula $J^1\text{-}J^2\text{-}C(J^{10})(Q^{10})Y^3C(J^{11})(Q^{11})C(=Z^{10})-$ wherein $J^1$ and $J^2$ are as defined above,
$J^{10}$ and $J^{11}$ are as defined for $J^3$,
$Q^{10}$ and $Q^{11}$ are as defined for $Q^3$,
$Y^3$ is as defined above,
$Z^{10}$ is as defined above,
$J^{10}$ and $Q^{10}$, or $J^{11}$ and $Q^{11}$ may be bonded, or $J^2$ and $Q^{10}$, or $Y^3$ and $Q^{11}$ may be bonded to form a ring,
(6) a group represented by the formula $J^1\text{-}J^2\text{-}C(J^{12})(Q^{12})C(=Z^{10})-$
wherein $J^1$ and $J^2$ are as defined above,
$J^{12}$ is as defined for $J^3$,
$Q^{12}$ is as defined for $Q^3$,
$Z^{10}$ is as defined above,
$J^{12}$ and $Q^{12}$ may be bonded, or $J^2$ and $Q^{12}$ may be bonded to form a ring, or
(7) a group represented by the formula $J^1-$
wherein $J^1$ is as defined above,
or a salt or prodrug thereof.

2. The metastin derivative (I) according to claim 1, which is
(i) 4-fluorobenzoyl-Phe-X-Arg-Trp-NH$_2$ (SEQ ID NO: 68),
(ii) D-Tyr-Asn-Trp-Asn-Ser-Phe-X-Arg-Trp-NH$_2$,
(iii) 3-(3-indolyl)propionyl-Asn-Ser-Phe-X-Arg-Trp-NH$_2$ (SEQ ID NO: 69),
(iv) 3-phenylpropionyl-Asn-Ser-Phe-X-Arg-Trp-NH$_2$ (SEQ ID NO: 70),
(v) 2-(indol-3-yl)ethylcarbamoyl-Asn-Ser-Phe-X-Arg-Trp-NH$_2$ (SEQ ID NO: 71),
(vi) D-Tyr-Asn-Pya(4)-Asn-Ser-Phe-X-Arg-Trp-NH$_2$,
(vii) TyrΨ(CH$_2$NH)Asn-D-Trp-Asn-Ser-Phe-X-Arg-Trp-NH$_2$,
(viii) D-Tyr-D-Asn-Pya(4)-Asn-Ser-Phe-X-Arg-Trp-NH$_2$,
(ix) D-Tyr-D-Pya(4)-Asn-Ser-Phe-X-Arg-Trp-NH$_2$,
(x) 3-pyridylpropionyl-Asn-Ser-Phe-X-Arg-Trp-NH$_2$ (SEQ ID NO: 72),
(xi) 4-imidazoleacetyl-Asn-Ser-Phe-X-Arg-Trp-NH$_2$ (SEQ ID NO: 73),
(xii) 4-nitrobenzoyl-Phe-X-Arg-Trp-NH$_2$ (SEQ ID NO: 74),
(xiii) 4-(aminomethyl)benzoyl-Phe-X-Arg-Trp-NH$_2$ (SEQ ID NO: 75),
(xiv) pyridine-2-carbonyl-Phe-X-Arg-Trp-NH$_2$ (SEQ ID NO: 76),
(xv) benzoyl-Phe-X-Arg-Trp-NH$_2$ (SEQ ID NO: 77),
(xvi) 4-(bis-picolylaminomethyl)benzoyl-Phe-X-Arg-Trp-NH$_2$ (SEQ ID NO: 78), or
(xvii) 4-(guanidinomethyl)benzoyl-Phe-X-Arg-Trp-NH$_2$ (SEQ ID NO: 79), or a salt thereof.

3. A pharmaceutical composition comprising the metastin derivative (I) according to claim 1 or a salt thereof or a prodrug thereof.

4. The pharmaceutical composition according to claim 3, which is an agent for the treatment of cancer.

5. The pharmaceutical composition according to claim 3, which is a pancreatic function regulator, an agent for the treatment of acute or chronic pancreatitis or pancreatic cancer, a placental function regulator, an agent for the treatment of villous cancer, hydatidiform mole, invasive mole, miscarriage, fetus underdevelopment, glucose metabolism disorder, abnormal lipid metabolism or induction of childbirth, a gonadal function improver, an agent for the treatment of hormone dependency cancer, infertility, endometriosis or hysteromyoma, inducing or stimulating ovulation, gonadotropic hormone secretagogue or sex hormone secretagogue, and an agent for the treatment of Alzheimer's disease or mild cognitive impairment.

* * * * *